US006278890B1

(12) United States Patent
Chassaing et al.

(10) Patent No.: US 6,278,890 B1
(45) Date of Patent: Aug. 21, 2001

(54) NON-INVASIVE TURBULENT BLOOD FLOW IMAGING SYSTEM

(75) Inventors: Charles E. Chassaing, Raleigh; Scott Donaldson Stearns, Cary; Mark Harold Van Horn, Raleigh, all of NC (US); Carl Ashley Ryden, Boston, MA (US)

(73) Assignee: MedAcoustics, Inc., Raleigh, NC (US)

( * ) Notice: Subject to any disclaimer, the term of this patent is extended or adjusted under 35 U.S.C. 154(b) by 0 days.

(21) Appl. No.: 09/188,510

(22) Filed: Nov. 9, 1998

(51) Int. Cl.[7] ........................................................... A61B 5/05
(52) U.S. Cl. ........................... 600/407; 600/454; 600/481; 600/504
(58) Field of Search ........................... 600/407, 454–458, 600/481–485, 488, 500, 504

(56) References Cited

U.S. PATENT DOCUMENTS

| Re. 32,180 | 4/1861 | Chase . |
| 3,442,264 | 5/1969 | Levitt .................................. 128/2.06 |
| 3,573,394 | 4/1971 | Birnbaum ............................. 128/2.05 |

(List continued on next page.)

FOREIGN PATENT DOCUMENTS

| 3234584A1 | 3/1984 | (DE) . |
| 0194823 A2 | 3/1986 | (EP) . |
| 3531399A1 | 3/1986 | (DE) . |
| 0201421A1 | 11/1986 | (EP) . |
| WO A 0 201 421 | 11/1986 | (EP) . |
| 0325805A2 | 8/1989 | (EP) . |
| 0 528 279 | 2/1993 | (EP) . |
| 2507424 | 12/1982 | (FR) . |
| 2166871A | 5/1986 | (GB) . |
| 2188732 | 10/1987 | (GB) . |
| WO/90-08506 | 8/1990 | (WO) . |
| WO 93/22970 | 11/1993 | (WO) . |
| 94 05207 | 3/1994 | (WO) . |
| WO 95/06525 | 3/1995 | (WO) . |

OTHER PUBLICATIONS

Xu, Gang, et al., Reconstruction Techniques, *Epipolar Geometry in Stereo, Motion and Object Recognition—A Unified Approach*, Ch. 3.4.3, pp. 153–155 (1996).

Faugeras, Olivier, Ordering, *Three–Dimensional Computer Vision—A Geometric Viewpoint*, Ch. 6, pp. 178–181 (MIT Press, 1993).

Haralick, Robert M., et al., Structure from Stereo by Using Correspondence, *Computer and Robot Vision*, vol. II, Ch. 16.6 (Addison–Wesley 1993).

Longuet–Higgins, H.C., A computer algorithm for reconstructing a scene from two projections, *Nature*, vol. 293, pp. 133–135 (Sep. 10, 1981).

Horn, Berthold, Disparity between the Two Images, *Robot Vision*, Ch. 13.1, pp. 300–301, 320–322 (MIT Press 1986).

Horn, "Computing Depth," Robot Vision, Ch. 13.6, pp. 311–312 (MIT Press 1986).

Nilsson et al., "A Combined Microphone for Simultaneous Recording of Pulse, Phono and Reference ECG," Electromedica, vol. 2, No. 76, pp. 64–68 (1976).

(List continued on next page.)

*Primary Examiner*—Eric F. Winakur
*Assistant Examiner*—Ryan Carter
(74) *Attorney, Agent, or Firm*—Myers Bigel Sibley & Sajovec, P.A.

(57) ABSTRACT

A non-invasive methodology and instrumentation for the detection and localization of abnormal blood flow in a vessel of a patient is described. An array of sensors are positioned on an area of a patient's body above a volume in which blood flow may be abnormal. Signals detected by the sensor array are processed to display an image which may indicate the presence or absence of abnormal blood flow.

37 Claims, 41 Drawing Sheets

U.S. PATENT DOCUMENTS

| | | | |
|---|---|---|---|
| 3,799,147 | 3/1974 | Adolph et al. | 128/2.05 |
| 3,903,733 | 9/1975 | Murayama et al. | 73/71.4 |
| 4,008,408 | 2/1977 | Kodama | 310/9.1 |
| 4,054,808 | 10/1977 | Tanaka | 310/323 |
| 4,094,308 | 6/1978 | Cormier | 128/2.05 R |
| 4,146,955 | 4/1979 | Young, Jr. et al. | 29/594 |
| 4,226,248 | 10/1980 | Manoli | 128/773 |
| 4,234,813 | 11/1980 | Iguchi et al. | 310/366 |
| 4,255,791 | 3/1981 | Martin | 364/514 |
| 4,268,912 | 5/1981 | Congdon | 367/163 |
| 4,308,870 | 1/1982 | Arkans | 128/640 |
| 4,376,302 | 3/1983 | Miller | 367/157 |
| 4,385,255 | 5/1983 | Yamaguchi et al. | 310/335 |
| 4,387,378 | 6/1983 | Henderson | 343/854 |
| 4,406,967 | 9/1983 | Obara et al. | 310/366 |
| 4,413,630 | 11/1983 | Anderson et al. | 128/661 |
| 4,424,465 | 1/1984 | Ohigashi et al. | 310/335 |
| 4,428,380 | 1/1984 | Wong et al. | 128/715 |
| 4,458,693 | 7/1984 | Badzinski et al. | 128/715 |
| 4,491,051 | 1/1985 | Barcus | 84/1.16 |
| 4,509,527 | 4/1985 | Fraden | 128/671 |
| 4,546,777 | 10/1985 | Groch et al. | 128/715 |
| 4,549,551 | 10/1985 | Dyck et al. | 128/689 |
| 4,586,514 | 5/1986 | Schlager et al. | |
| 4,628,321 | 12/1986 | Martin | 342/379 |
| 4,630,203 | 12/1986 | Szirtes | 364/414 |
| 4,656,385 | 4/1987 | Tanaka | 310/348 |
| 4,697,597 | 10/1987 | Sanz et al. | 128/699 |
| 4,700,712 | 10/1987 | Schmid | 128/699 |
| 4,712,565 | 12/1987 | Katz et al. | 128/715 |
| 4,742,458 | 5/1988 | Nathans et al. | 364/417 |
| 4,777,961 | 10/1988 | Saltzman | 128/715 |
| 4,781,200 | 11/1988 | Baker | 128/670 |
| 4,784,154 | 11/1988 | Shirley et al. | 128/715 |
| 4,792,145 | 12/1988 | Eisenberger et al. | 128/715 |
| 4,803,986 | 2/1989 | Difresne et al. | 128/385 |
| 4,803,996 | 2/1989 | Peel et al. | 128/710 |
| 4,805,633 | 2/1989 | Kotani et al. | 128/715 |
| 4,812,976 | 3/1989 | Lundy | 364/413.06 |
| 4,821,584 | 4/1989 | Lembke | 73/862.68 |
| 4,840,183 | 6/1989 | Takahashi et al. | 128/715 |
| 4,842,411 | 6/1989 | Wood | 356/376 |
| 4,862,144 | 8/1989 | Tao | 340/573 |
| 4,862,361 | 8/1989 | Gordon et al. | 364/413.06 |
| 4,862,897 | 9/1989 | Eisenberg et al. | 128/715 |
| 4,905,706 | 3/1990 | Duff et al. | 128/701 |
| 4,924,875 | 5/1990 | Chamoun | 128/696 |
| 4,928,705 | 5/1990 | Sekhar et al. | 128/773 |
| 4,947,859 | 8/1990 | Brewer et al. | 128/715 |
| 4,957,369 | 9/1990 | Antonsson | 356/376 |
| 4,967,760 | 11/1990 | Bennett, Jr. et al. | 128/715 |
| 4,991,581 | 2/1991 | Andries | 128/715 |
| 5,002,058 | 3/1991 | Martinelli | 128/662 |
| 5,002,060 | 3/1991 | Nedivi | 128/671 |
| 5,003,605 | 3/1991 | Phillipps et al. | 381/67 |
| 5,010,889 | 4/1991 | Bredesen et al. | 128/715 |
| 5,012,815 | 5/1991 | Bennett, Jr. et al. | 128/715 |
| 5,025,809 | 6/1991 | Johnson et al. | 128/715 |
| 5,035,247 | 7/1991 | Heimann | 128/715 |
| 5,036,857 | 8/1991 | Semmlow et al. | 128/715 |
| 5,086,776 | 2/1992 | Fowler, Jr. et al. | 128/661.09 |
| 5,109,863 | 5/1992 | Semmlow et al. | 128/715 |
| 5,129,403 | 7/1992 | Henriquez et al. | 128/773 |
| 5,140,992 | 8/1992 | Zuckerwar et al. | 128/715 |
| 5,164,627 | 11/1992 | Popek | 310/313 B |
| 5,176,153 | 1/1993 | Eberhardt | 128/897 |
| 5,213,108 | 5/1993 | Bredesen et al. | 128/715 |
| 5,218,969 | 6/1993 | Bredesen et al. | 128/710 |
| 5,301,679 | 4/1994 | Taylor | 128/773 |
| 5,315,512 | 5/1994 | Roth | 364/413.25 |
| 5,337,752 | 8/1994 | Reeves | 128/700 |
| 5,363,401 | 11/1994 | Lucas et al. | 375/1 |
| 5,365,937 | 11/1994 | Reeves et al. | 128/715 |
| 5,381,804 | 1/1995 | Shambroom | 128/731 |
| 5,455,385 | 10/1995 | Newton et al. | 174/52.4 |
| 5,501,229 | 3/1996 | Selker et al. | 128/696 |
| 5,553,113 | 9/1996 | Weedon | 378/98.5 |
| 5,595,188 | 1/1997 | Kassal | 128/773 |
| 5,598,845 | 2/1997 | Chandraratna et al. | 128/662.03 |
| 5,618,869 | 4/1997 | Austin et al. | 128/691 |
| 5,638,823 | 6/1997 | Akay et al. | 128/691 |
| 5,673,702 | 10/1997 | Albrecht et al. | 128/712 |
| 5,680,513 | 10/1997 | Hyland et al. | 395/21 |
| 5,686,917 | 11/1997 | Odom et al. | 341/141 |
| 5,687,738 | 11/1997 | Shapiro et al. | 128/715 |
| 5,705,365 | 1/1998 | Albrecht et al. | 128/702 |
| 5,718,233 | 2/1998 | Selker et al. | 128/696 |
| 5,724,967 | 3/1998 | Venkatachalam | 128/633 |
| 5,724,968 | 3/1998 | Iliff | 128/630 |
| 5,724,983 | 3/1998 | Selker et al. | 128/696 |
| 5,796,920 | 8/1998 | Hyland | 395/22 |
| 5,807,268 | 9/1998 | Reeves et al. | 600/528 |
| 5,885,222 | 3/1999 | Kassal et al. | 600/528 |

OTHER PUBLICATIONS

Oestreicher, "Field and Impedance of an Oscillating Sphere in a Viscoelastic Medium with an Application to Biophysics," J. Acoust. Soc. Am., vol. 23, No. 6, pp. 707–714 (Nov. 1951).

Verburg, "Transmission of Vibrations of the Heart to the Chestwall," Adv. Cardiovasc. Phys., vol. 5, (Part III), pp. 84–103 (1983).

"Gabor Spectrogram," DSP Software Development, National Instruments, Austin, TX (believed to be prior art).

Akay et al., "Application of Adaptive FTF/FAEST Zero Tracking Filters to Noninvasive Characterization of the Sound Pattern Caused by Coronary Artery Stenosis Before and After Angioplasty", Annals of Biomedical Engineering, vol. 21, pp. 9–17 (1993).

Akay et al., "Application of Adaptive Filters to Noninvasive Acoustical Detection of Coronary Occlusions Before and After Angioplasty," IEEE Transactions on Biomedical Engineering, vol. 39, No. 2, pp. 176–183 (Feb. 1992).

Akay et al., "Noninvasive acoustical detection of coronary artery disease using the adaptive line enhancer method," Medical & Biological Engineering & Computing, vol. 30, pp. 147–154 (Mar. 1992).

Akay et al.,"Noninvasive Acoustical Detection of Coronary Artery Disease: A Comparative Study of Signal Processing Methods," IEEE Transactions on Biomedical Engineering, vol. 40, No. 6, pp. 571–5784 (Jun. 1993).

Donnerstein, "Continuous Spectral Analysis of Heart Murmurs for Evaluating Stenotic Cardiac Lesions," The Am. Journ. Card., vol. 64, pp. 625–630 (Sep. 15, 1989).

Durand et al., "Evaluation of FFT–Based and Modern Parametric Methods for the Spectral Analysis of Bioprosthetic Valve Sounds," IEEE Trans. on Biomedical Eng., vol. BME–33, No. 6, pp. 572–578 (Jun. 1986).

Foale et al., "Detection of aortic porcine valve dysfunction by maximum entropy spectral analysis," Circulation, vol. 68, No. 1, pp. 42–49 (Jul. 1983).

Fraden, "Application of Piezo/Pyroelectric Films in Medical Transducers," Jour. of Clinical Eng., vol. 13, No. 3, pp. 133–138 (Mar.–Apr. 1988).

Haralick, R. et al., Computer and Robot Vision, Addison–Wesley Publ. Co., NY, NY, pp. 31–40 (believed to be prior art).

Iwata et al., "Algorithm for Detecting the First and Second Heart Sounds by Spectral Tracking," Medical & Biological Engineers and Computing, pp. 19–26 (Jan. 1980).

Johnson et al., "Estimation of the Severity of Aortic Valve Stenosis by Frequency Analysis of the Murmur," J. Am. Coll. Cardiol., 1(5):1315–23 (1983).

Johnson et al., "Evaluation of Aortic Stenosis by Spectral Analysis of the Murmur," JACC, vol. 6, No. 1, pp. 55–65 (Jul. 1985).

Joo et al."Pole–Zero Modeling and Classification of Phonocardiograms," IEEE Trans. on Biomedical Eng., vol. BME–30, No. 2, pp. 110–118 (Feb. 1983).

Kagawa et al., "Real–time sound spectroanalysis for diagnosis of malfunctioning prosthetic valves," J. Thorac. Cardiovasc. Surg., vol. 79, pp. 671–679 (May 1980).

Lees et al., "Phonoangiography: A New Noninvasive Diagnostic Method for Studying Arterial Disease," Proceedings of the National Academy of Sciences, vol. 67, No. 2, pp. 935–942 (Oct. 1970).

Qian et al., "Orthogonal–Like Discrete Gabor Expansion," 26th Conf. on Infor. Sci an Systems, Princeton University (Mar. 18, 1992).

Semmlow et al., "Noninvasive Detection of Coronary Artery Disease Using Parametric Spectral Analysis Methods," *IEEE Engineering in Medicine and Biology Magazine*, pp. 33–36 (Mar. 1990).

Semmlow et al., "Coronary Atery Disease—Correlates Between Diastolic Auditory Characteristics and Coronary Artery Stenoses," *IEEE Transactions on Biomedical Engineering*, vol. BME–30, No. 2, pp. 136–139 (Feb. 1983).

Semmlow et al., "Non–Invasive Diagnosis of Coronary Artery Disease by Enhanced Coronary Phonocardiography," IEEE Frontiers of Eng. in Health Care, pp. 181–185 (1982).

Stein et al., "Frequency Spectra of the First Heart Sound and of the Aortic Component of the Second Heart Sound in Patients with Degenerated Porcine Bioprosthetic Valves," The Am. Journ. of Carad., vol. 53, pp. 557–581 (Feb. 1, 1984).

von Glerke, H. et al., "Physics of Vibrations in Living Tissues," J. App. Physiology, vol. 4, pp. 886–900 (Jun. 1952).

Wang et al., Modeling Sound Generation in Stenosed Coronary Arteries, IEEE Transactions on Biomedical Engineering, vol. 37, No. 11, pp. 1087–1094 (Nov. 1990).

Pre-Intervention

Post-Intervention

NON-INVASIVE TURBULENT BLOOD FLOW IMAGING SYSTEM

TABLE OF CONTENTS

FIELD OF THE INVENTION
BACKGROUND OF THE INVENTION
SUMMARY OF THE INVENTION
DEFINITIONS
DESCRIPTION OF THE FIGURES
DETAILED DESCRIPTION OF THE INVENTION
1. The Clinical Workstation
2. The Sensors and Sensor Arrays
3. The Acoustic Imaging System
4. Procedure for Use of The Clinical Workstation
5. Data Acquisition and Processing Beamformers
   (a) Near Field Conventional Beamformer
      1. Vector Formulation
      2. Matrix Formulation
      3. Summary Regarding Vector and Matrix Formulation
   (b) Adjustable Gain/Resolution Null Space Beamformer
6. Compression Energy Suppression Beamformers
   (a) Velocity Filtering
      (i) Linear Arrays—Uniform Sensor Spacing
      (ii) Non-Linear Arrays
   (b) Steering a Null at the Compression Wave
      (i) Option 1—See FIG. 24
      (ii) Option 2—See FIG. 25
   (c) Beamforming Methods When Wave Speed (c) as a Function of Frequency is Unknown
      (i) Optimal Gridding
      (ii) Non-Linear Unconstrained Optimization
      (iii) Display of Source Location
7. Non-invasive Detection of Change in Coronary Artery Stenosis
8. Signal to Noise Ratio Enhancement
EXEMPLIFICATION OF THE INVENTION
Claims
ABSTRACT

FIELD OF THE INVENTION

The present invention relates generally to non-invasive blood flow imaging systems and more particularly to systems which are suitable for detecting turbulent blood flow.

BACKGROUND OF THE INVENTION

It is known that vibration of the surrounding structures caused by turbulent blood flow in a partially occluded vessel may produce sounds which are significantly attenuated at body surfaces.

Turbulent blood flow is evidenced by non-uniform spatial distribution of blood flow sound phase coherence. Absent turbulence, blood flow sound phase coherence is generally uniform.

Various techniques for acoustic detection of turbulent blood flow are known. See, e.g., Lees, et al., (1970) *Proceedings of the National Academy of Sciences* 67(2):935–942; Semmlow, et al., (1982) "Non-Invasive Diagnosis of Coronary Artery Disease by Enhanced Coronary Phonocardiography", Abstract, IEEE Frontiers of Engineering in Health Care, pp. 181–185; Semmlow, et al., (1983) *IEEE Transactions on Biomedical Engineering, BME*-30(2):136–139; Wang, et al., (1990) *IEEE Transactions on Biomedical Engineering*, 37(11):1087–1094; Semmlow, et al., (1990) *IEEE Engineering in Medicine and Biology Magazine*, pp. 33–36; Akay, et al., (1992(1)) *IEEE Transactions on Biomedical Engineering*, 39(2):176–183; Akay, et al., (1992(2)) *Medical & Biological Engineering & Computing*, 30:147–154; Akay, et al., (1993(1)) *IEEE Transactions on Biomedical Engineering*, 40(6):571–578; Akay, et al., (1993(2)) *Annals of Biomedical Engineering*, 21:9–17; Verburg, J. (1983) *Adv. Cardiovasc. Phys.* 5(*Part III*):84–103.

SUMMARY OF THE INVENTION

This invention provides reliable, non-invasive methodology and instrumentation for the in vivo detection and localization of abnormal blood flow in a patient.

Generic embodiments of the invention entail detection and imaging of non-uniform spatial distribution of phase coherence of blood flow sounds in a volume of a patient's body below a sensor array.

The wave signals detected by the sensor array comprise a shear wave component and other components including a compression wave component. In the preferred practice of the invention, the shear wave component is isolated from the compression wave component. The isolated shear wave component is processed to provide a display of the spatial distribution of phase coherence of the blood flow sounds in the volume of the patient's body below the sensor array. An essentially uniform display indicates the absence of an abnormal blood flow. A non-uniform display may indicate the presence of an occlusion and the extent of the turbulent flow in the patient's vessel.

The invention may include sensor signal conditioning circuitry and software to implement one or more algorithms. The signal processing circuitry may be combined with a volumetric imager in a mobile clinical workstation operable by a medical technician or a doctor. The invention may include means for enhancement of the signal to noise ratio of the sensor signals.

An important aspect of the invention is a novel non-invasive method for detecting and tracking coronary artery stenosis change following percutaneous intervention.

DEFINITIONS

In this specification, the following words or expressions have the meanings set forth.

Field

An area or volume of space where certain physical laws govern. Typically, those laws are concerned with action at a distance. Examples: a gravitational field, an electromagnetic field or an acoustical field. In this specification, unless otherwise indicated, field refers to a volume of space where the laws governing wave propagation in a visco-elastic media are true.

Near Field

In an isotropic media when a wave front propagates out from a point source, the wave front is spherical in shape. In this specification, "Near Field" means a field near the source, where the wave front has high curvature. When an array of equally spaced sensors detects this curved wave front the delays, or phase shifts between the sensors will be different. If the wave velocity in the media is known, the location of the source in relation to the array can be determined. The location would have 3 dimensions either in Cartesian, Polar, or Spherical coordinates. If a volume a plane is considered then the location will have two dimensions.

Far Field

In this specification "Far Field" means a field far from the source, where the wave front has low curvature. A wave front very far from the source appears planar with no curvature. When an array of equally spaced sensors detects this plane wave front the delays, or phase shifts between the sensors may be different. By a coordinate transformation, directions can be found where the delay is constant per distance across the array and in the orthogonal direction the delay is zero per distance across the array. Determination of the direction of the source in relation to the array is possible of the wave velocity in the medium is known. The direction would have two angular dimensions in spherical coordinates. If a plane as exists with a linear array is considered, then the direction will have one dimension, an angle and the delay or phase shifts between sensors will be constant.

Advance and Sum Beamformer or Bartlett Beamformer or Conventional Beamformer

An algorithm which combines data acquired from a multichannel array of sensors by time shifting the time histories and then summing the signal. If the time histories are shifted negatively with respect to time (advanced) then the algorithm is typically called an advance and sum beamformer. If the time histories are shifted positively with respect to time (delayed) then the algorithm is typically called a delay and sum beamformer.

Path Model

A mathematical representation of the net transformation undergone by a signal as it propagates through a medium or through a circuit. A signal typically originates at a source and ends at a receiver.

Steering Vector

A vector derived from a path model used to steer the response lobe (beam) for an array of sensors.

Vessel

Any part of the human circulatory system through which blood flows. Includes arteries, veins, and the heart.

Abnormal Blood Flow

Any non-laminar, e.g., turbulent blood flow in a vessel.

Stenosis

Any artifact which reduces the effective cross-section of a vessel with consequent blood flow abnormality.

Abnormal Blood Flow Signal

A propagating wave generated by abnormal blood flow usually comprising a compression wave component and a shear wave component.

Sensor or Accelerometer

Any current or voltage mode device which generates an electric signal from displacement or a derivative thereof upon detection of a sound wave.

Sensor Array

The pattern or spaced arrangement of a plurality of sensors on or to be placed on the body surface of a patient. The array of sensors may be fixed in a device or pod positionable on the body surface of a patient.

Phonocardiography

The graphic representation of the sounds that originate in the heart and great vessels. As commonly used, the term phonocardiography also comprises carotid, apex and venous pulse sounds.

Great Vessels

The vessels that carry blood toward and away from the heart. The vessels carrying blood away from the heart include the aorta and pulmonary artery. The vessels carrying blood toward the heart include the superior and inferior vena cava.

Coherence

For a stochastic process x(t), the coherence function is defined as:

$$C(t_1,t_2)=E\{X(t_1)X^H(t_2)\}-E\{X(t_1)\}E\{X^H(t_2)\}$$

where $E\{\bullet\}$ denotes the statistical expectation operator, H is Hermetian or conjugate transpose, and $X(t_1)$ and $X(t_2)$ are random variables.

Phase Coherence

The coherence of the phase angle associated with a complex random process.

Algorithm

A series of steps or a method to achieve an information objective, e.g., the identification or location of an abnormal blood flow.

Compression Wave

A wave which compresses the medium through which it passes; the disturbance mechanism acts in the direction of the wave propagation.

Shear Wave

A wave whose propagated disturbance is a shear displacement in an elastic medium.

Beam

A concentrated, unidirectional receiver of sound.

Beamformer

An algorithm that defines or creates a beam.

Beamforming

The process of selectively controlling the response of a sensor array to increase sensitivity to a source location. Beamforming is a search through 3-D or 4-D data space to find the coordinates that yield maximum output at each of a plurality of frequencies.

Null

In the context of this invention, null means zero beamformer response at a specific location or angle. See FIG. 21.

Null Space

Null space is a vector subspace, if present, of a matrix.

Steering a Null

Controlling the location of a null in the response of a beamformer. See FIG. 22. For example, the goal may be to place the null at the location or angle where the interfering signal, e.g., a jammer, originates.

Velocity Filtering

Means for separating wave forms, including shear waves from compression waves as a function of the respective wave speeds in a medium, e.g., human tissue.

4-D Space or 4-Space or (x,y,z,c) Space

Four-dimension space in which the fourth dimension, "c", is the velocity of shear wave propagation.

Three Dimensional Regularly Spaced Grid

FIGS. 26A, B and C and FIG. 27 illustrate of a three dimensional regularly spaced grid.

Four Dimensional Optimal Grid

A 4D optimal grid A which maintains constant beamwidth resolution throughout the volume with a minimum number of points and therefore a minimum amount of computational effort. See FIGS. 28A, 28B, 28C and 29.

Each of these figures represents a projection of a four dimensional grid into a three dimensional space. The four dimension is wave speed. Each of the points which can be seen in the three dimensional space of the figures exists at several different speeds. These speeds are spaced according to the beamformer's beamwidth in c (speed) at that point in four space.

Photogrammetry

Analytic photogrammetry refers to the analytic mathematical techniques that permit the inference of geometric relations between points and lines in the two-dimensional perspective projection image space and the three-dimensional object space. Digital photogrammetry refers to the computer processing of perspective projection digital images with analytic photogrammetry techniques as well as other computer techniques for the automatic interpretation of scene or image content.

Feature

Prominent part or characteristic that distinguishes data, a signal or an image as a member of one class distinct from another.

Feature Vector

An assembled plurality of individual features.

Feature Extraction

The process or procedure or algorithm by which a feature or features are generated or computed from the data. Extraction includes the steps of assembling the features into a vector and assembling multiple observations of the feature vector into a feature matrix.

DESCRIPTION OF THE FIGURES

FIG. 3 is a reproduction of FIG. 1 of U.S. Pat. No. 5,365,937.

FIG. 4 is a reproduction of FIG. 2 of U.S. Pat. 5,365,937.

DETAILED DESCRIPTION OF THE INVENTION

The present invention now will be described more fully hereinafter with reference to the accompanying figures, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. Some embodiments of the present invention may be embodied as methods and systems of computer program products. As will be appreciated by those of skill in the art, the various embodiments of the present invention may take the form of an entirely hardware embodiment, an entirely software embodiment or a combination of hardware and software.

Figure 40:
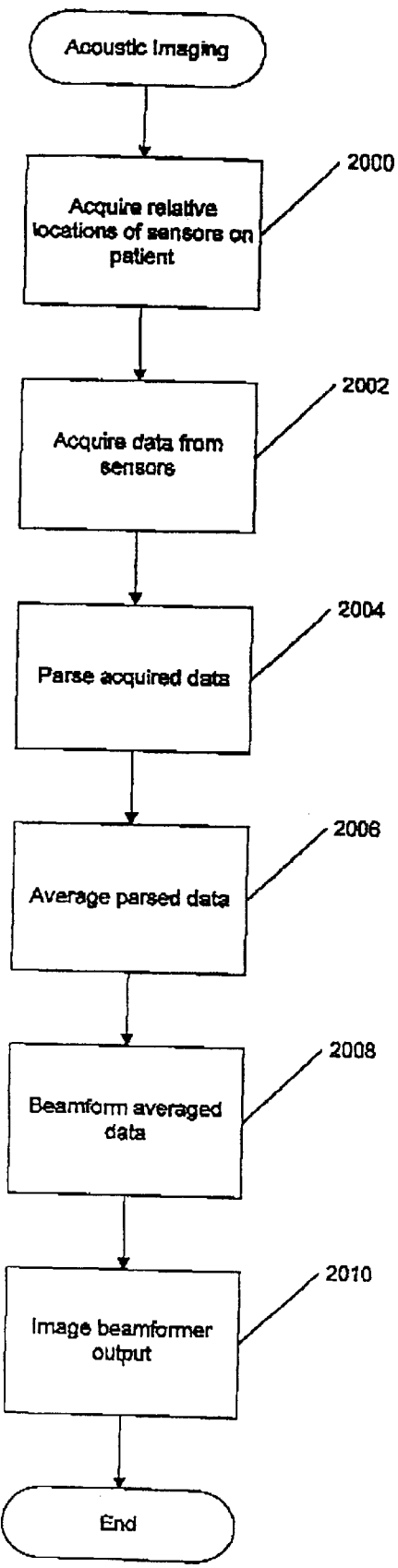
FIG. 40 is a flow chart that illustrates operations of one embodiment of the invention.
Figure 41:
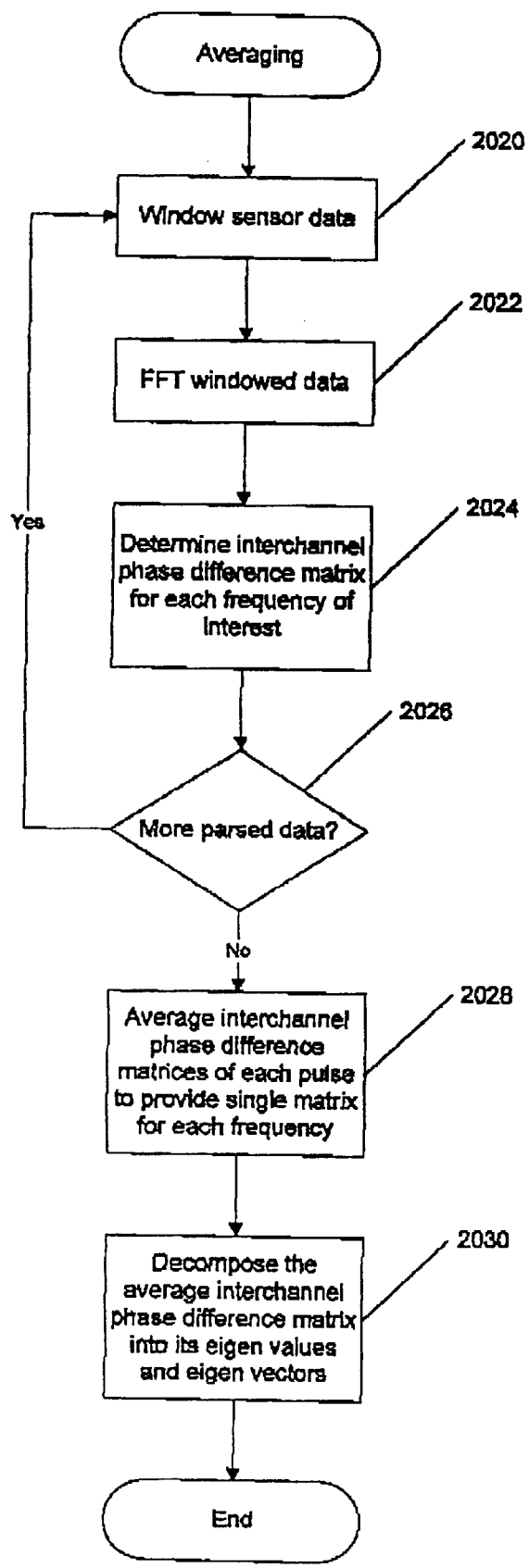
FIG. 41 is a flow chart or logic diagram that illustrates the parsed data averaging process of block 2006 of FIG. 40 according to one embodiment of the invention.
Figure 42:
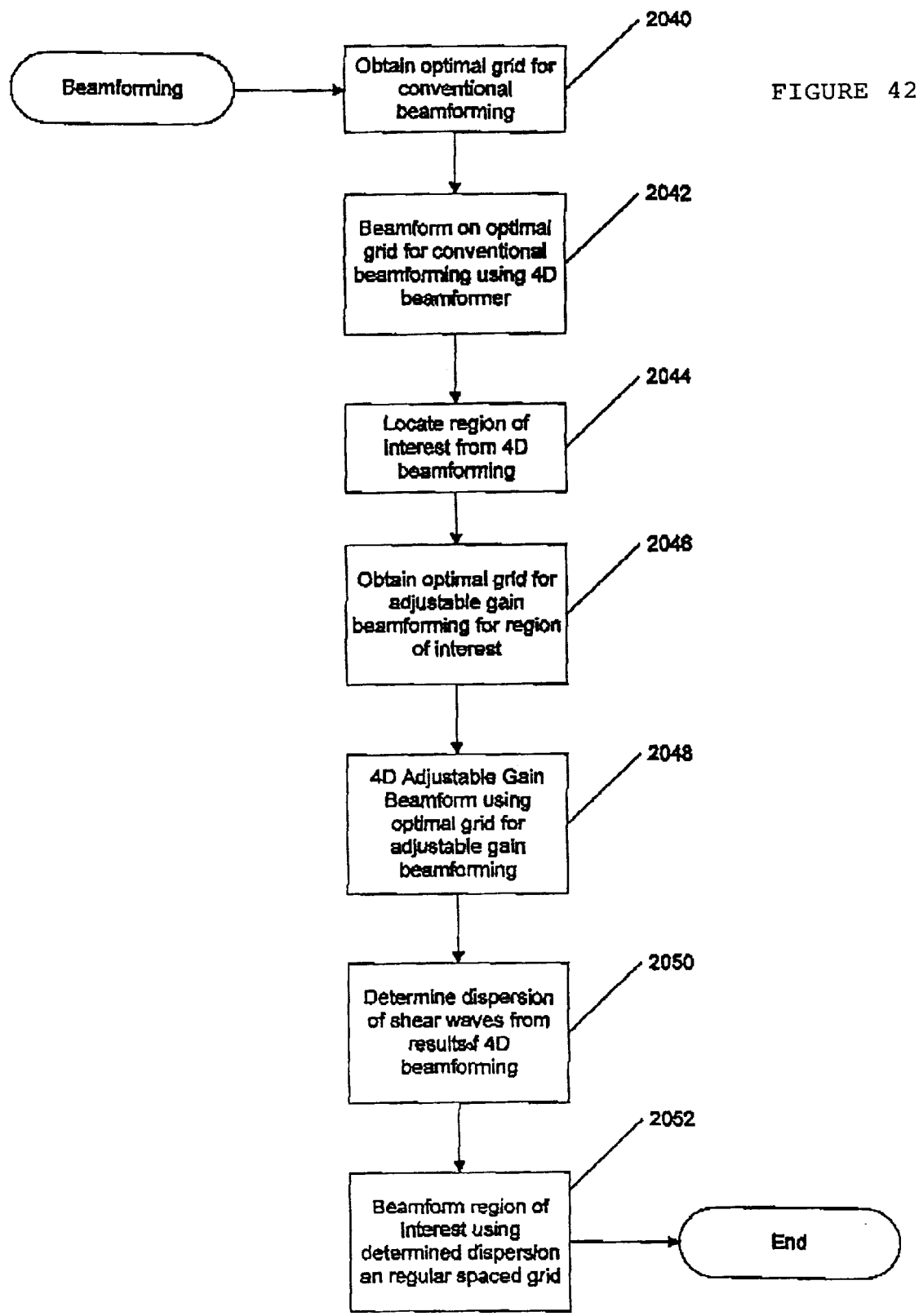
FIG. 42 is a flow chart which illustrates the beamforming operations of block 2008 of FIG. 40.

The operation of the present invention is described herein with reference to flowcharts and block diagrams, FIGS. 40, 41 and 42.

FIG. 40 illustrates operations of one embodiment of the present invention. As seen in FIG. 40, the relative positions of shear wave sensors are determined (block 2000). Such relative locations may be determined by any number of methods including photogrammetry. The acoustic sensors may be any form of sensor suitable for obtaining acoustic information, but are preferably sensors with high sensitivity to shear wave patterns in tissue.

In addition to acquiring location information, acoustic information, preferentially shear wave information, is acquired from the sensor array (block 2002). This acoustic information preferably includes information during the second quarter of the diastolic interval of a patient for which acoustic imaging is desired. Also acquired may be ECG information, ambient noise information, patient noise information breath gating information.

The acquired information regarding the sensors, the patient and the ambient conditions may then be used to parse and correct the sensor data (block 2004). The parsing of the data preferably includes isolating sensor data corresponding to the time period for the second quarter diastolic interval of the patient. Data may also be discarded if, for example, the presence of ambient noise or patient noise is detected which would adversely impact the sensor data. Thus, for example, if a loud noise is detected or if breathing sounds are detected, the data corresponding to those time periods may be discarded. Alternatively, the sensor data could be corrected for such extraneous noise. In either case, the result of the parsing operation is a series of sensor data synchronized to heartbeats of the patient.

The parsed data from multiple heartbeats is then averaged to provide a single set of averaged sensor data (block 2006). This averaging is preferably carried out so as to maintain phase information from the sensory array. The averaged data is then beamformed (block 2008) and the results of that beamforming are imaged (block 2010).

FIG. 41 illustrates the averaging process of block 2006 according to one embodiment of the present invention. In performing the averaging, the sensor data is first windowed (block 2020) and an FFT of the windowed data performed (block 2022). An interchannel phase difference matrix is then determined for each frequency of interest (block 2024). The interchannel phase difference matrix may be determined as described above.

When all of the interchannel phase difference matrices have been determined for each set of sensory data (block 2026), the interchannel phase difference matrices are averaged (block 2028). This averaging results in a single interchannel phase difference matrix for each frequency of interest. The average interchannel phase difference matrices are then decomposed into their eigen values and eigen vectors (block 2030) and utilized in beamforming as described elsewhere herein.

The beamforming operations of block 2008 are illustrated in FIG. 42. As seen in FIG. 42, an optimal grid 4D beamforming is first obtained (block 2040). This optimal grid provides search through a four dimensional volume utilizing the minimum beamformers as is described herein. The grid is determined based on the beamwidth in four dimensions of the beamformer to be used. The optimal grid may be computed for each session or may be precomputed.

The 4D grid is then used to beamform through the test volume (block 2042), however, the beamforming operation is not a conventional beamforming operation but utilizes a 4D beamformer in x,y,z and c space. This 4D beamforming is accomplished by expanding the optimal grid from 3D to 4D space such that beamforming may cover the desired range of c values with the minimum number of beamformers. Thus, the speed of propagation through the patient need not be known but may be obtained from the 4D beamformer output.

The results of the 4D beamforming are then utilized to narrow the field of search for an optional subsequent higher resolution beamforming operation. Thus, as seen in block 2044, a new region or regions of interest may be determined based on the results of the first beamforming operation. This new region of interest is preferably regions corresponding to maxima (potential sources) of the first beamforming operation. The region of interest is also preferably a region including one beamwidth from the estimated sources of the first beamforming operation.

After determining a narrower search region, a new optimal grid is obtained for a higher resolution beamformer, such as an adjustable gain beamformer (block 2046). As with the previous grid, the adjustable gain grid may be precomputed or computed for each use. Furthermore, the adjustable gain grid is also preferably a 4D grid.

Using the optimal grid, a 4D adjustable gain beamforming operation, as described above, is carried out for the new search region (block 2048). From this higher resolution beamforming operation a dispersion characteristic is determined (block 2050). This dispersion characteristic may be obtained from the beamformer results because the beamformer is a 4D beamformer and, therefore, has available sufficient information to determine speed versus frequency for the region of interest.

Utilizing the dispersion characteristics obtained from the 4D beamforming, a subsequent 3D beamforming operation is carried out in the region of interest utilizing a regularly spaced grid (block 2052). This subsequent beamforming operation is carried out so as to make imaging easier.

It will be understood that each block of the flowchart illustrations, and combinations of blocks in the flowchart illustrations, can be implemented by computer program instructions. These program instructions may be provided to a processor to produce a machine, such that the instructions which execute on the processor create means for implementing the functions specified in the flowchart block or blocks. The computer program instructions may be executed by a processor to cause a series of operational steps to be performed by the processor to produce a computer implemented process such that the instructions which execute on the processor provide steps for implementing the functions specified in the flowchart block or blocks.

Accordingly, blocks of the flowchart illustration support combinations of means for performing the specified functions, combinations of steps for performing the specified functions and program instruction means for performing the specified functions. It will also be understood that each block of the flowchart illustrations and combinations of blocks in the flowchart illustrations, can be implemented by special purpose hardware-based systems which perform the specified functions or steps, or combinations of special purpose hardware and computer instructions.

A specific aspect of the invention provides instrumentation and methodologies for detecting coronary artery stenosis change following successful percutaneous intervention. This aspect of the invention permits serial noninvasive post intervention assessments of a stenotic lesion.

1. The Clinical Workstation

Figure 1:
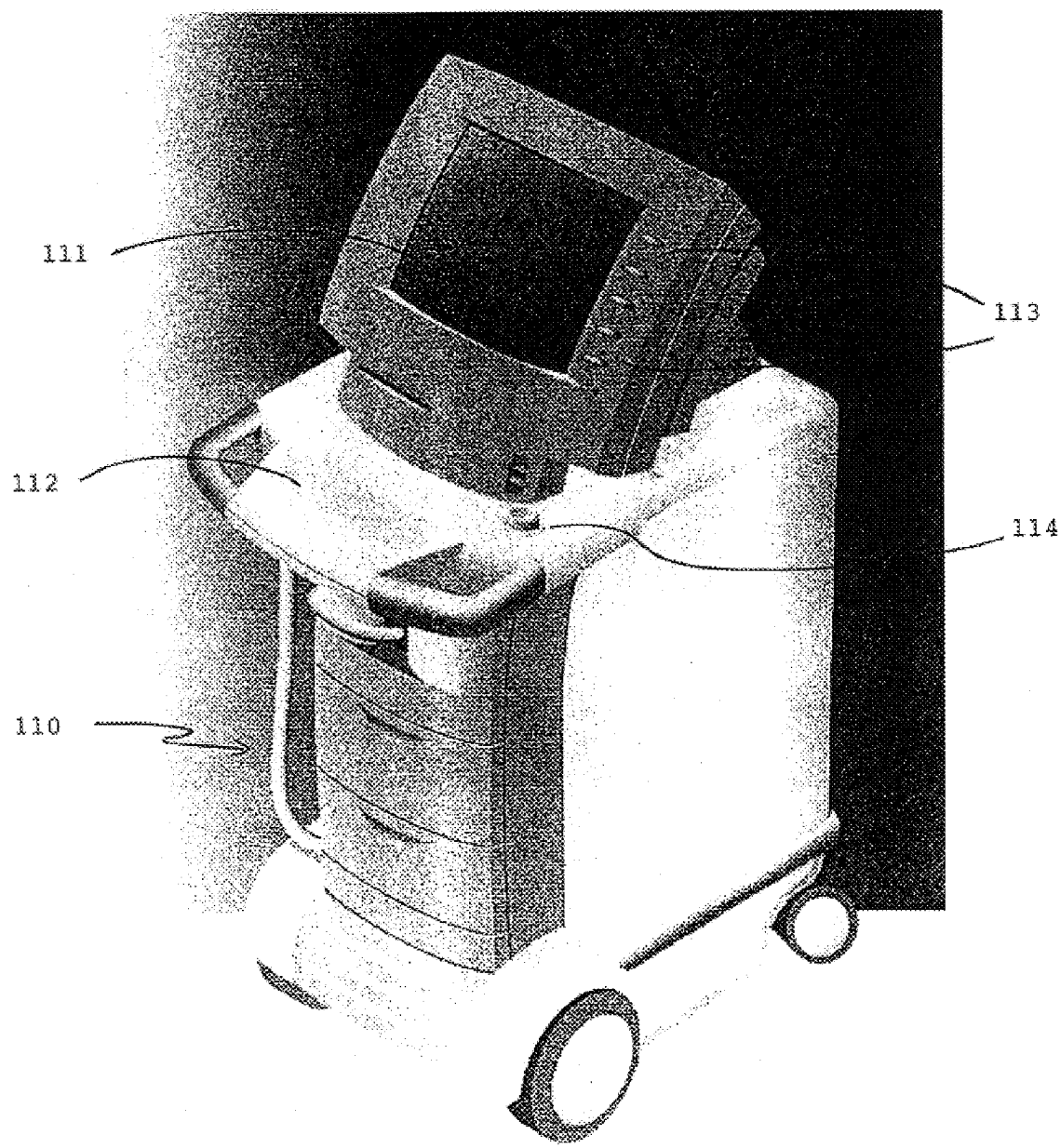
FIG. 1 is a front and side view of one form of a clinical workstation including an acoustic imaging system of the invention.

FIG. 1 illustrates a preferred clinical workstation configuration 110 which may include a computer monitor 111, a keyboard 112, five soft switches 113 and one rotary push dial 114 to permit an operator to enter patient information, control the system operations and select and review the data displayed.

The rotating push dial 114, as shown, has no physical stop points. It will transmit LEFT, RIGHT and PUSHED, RELEASED status information. Each of the soft switches 113, as shown, is a two-state (ON-OFF) device. The software interface to the soft switch panel occurs through low-level drivers (not shown) that communicate directly with the workstation 110. The data may be stored on a removable storage device (not shown) and printed on a graphics printer (not shown). The preferred operating system is a 32-bit Microsoft NT workstation version 4.0 or higher.

Figure 2B:
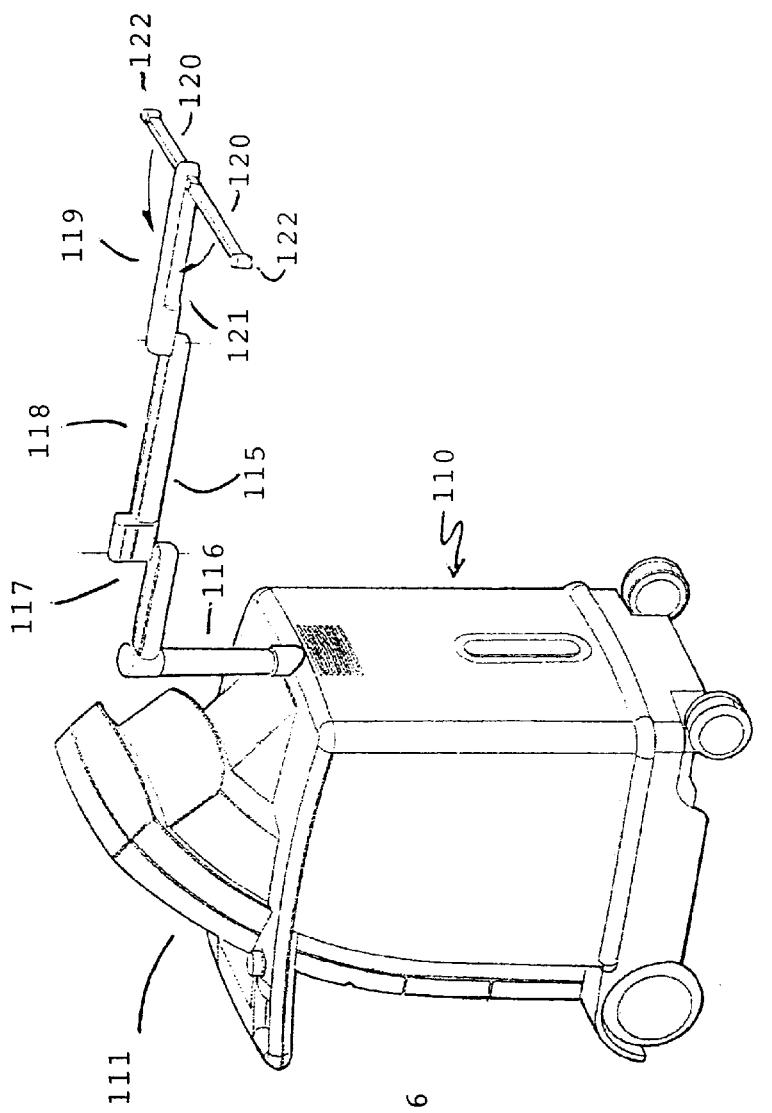
FIG. 2B is a view of the FIG. 2A form of the clinical workstation in which the arm for supporting cameras is shown extended.
Figure 2A:
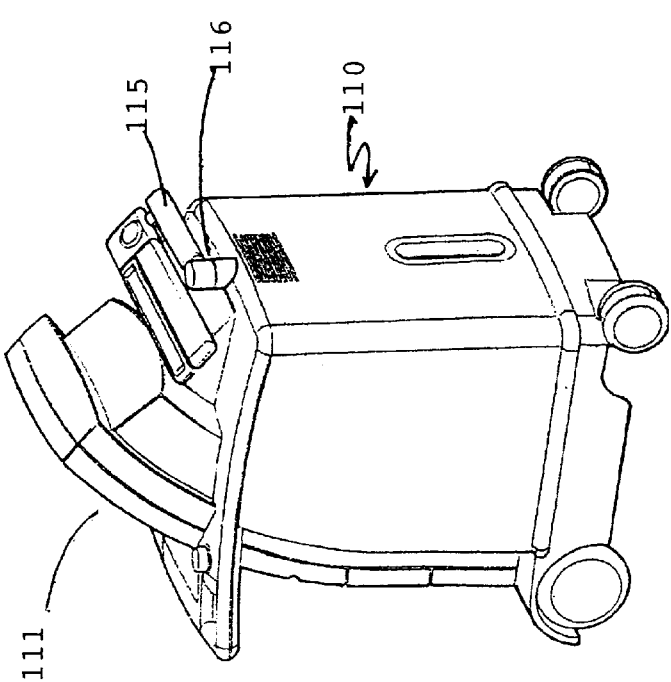
FIG. 2A is a view of a second form of a clinical workstation having a contracted extendable arm support for two cameras to locate sensors by photogrammetry.

FIGS. 2A and 2B are schematics that show a form of the workstation 110 having a fold-away extension arm 115 to support two cameras for the location of sensors by photogrammetry. A support member 116 for the extension arm 115 is stored in the cabinet of the workstation 110 when the arm is not extended. The extendable arm 115 includes three elements 117, 118 and 119. Element 117 is pivotably connected to the support 116 at one end and to the element 118 at the other end. The terminal element 119 is pivotably connected at the distal end to the element 118.

The element 119 has arms 120 foldable into recess 121 in the element 119. Each of the distal ends of the foldable arms 120 includes means 122 for the attachment of cameras to permit photogrammetric determination of sensor positions.

2. The Sensors and Sensor Arrays

The acoustic imaging system processes signals transmitted by a plurality of acoustic sensors positioned in an array on or adjacent a patient's body surface to detect or localize abnormal blood flow.

The sensors measure body surface response to abnormal blood flow sound signals. An electrical signal of broad frequency response, high sensitivity, and high signal to noise ratio (S/N) is provided. An ECG monitor signal may also be included to provide a reference for the cardiac cycle.

The sensors may be charge or voltage mode accelerometers or piezo film transducers. Sensors having substantially the performance characteristics set forth in Table 1 are preferred. However, other suitable sensors may be used.

TABLE 1

| | |
|---|---|
| Sensitivity | 5 V/g |
| Acceleration Range | 1 g (peak) |
| Amplitude Nonlinearity | 1% |
| Frequency Response | 20 Hz.–2,000 Hz. |
| Dynamic Range | 120 dB |
| Power Requirement | |
| Current Mode | 18–30 VDC, 4–10 mA |
| Voltage Mode | ±12 VDC, 4–10 mA |
| Electrical Noise | |
| Broadband | <1 micro 9 |
| Spectral (20 Hz) | −150 dB re. g/$\sqrt{Hz}$ |
| Spectral (100 Hz) | −158 dB re. g/$\sqrt{Hz}$ |
| Spectral (1000 Hz) | −163 dB re. g/$\sqrt{Hz}$ |
| Physical Dimensions | |
| Diameter | <1.6 cm |
| Height | <1.9 cm |
| Connector - Type: 4 Pins | |

Preferred individual sensors comprise a stretched piezoelectric film transducer. Typically, the transducer is a stretched polyvinylidene fluoride film.

Figure 3:
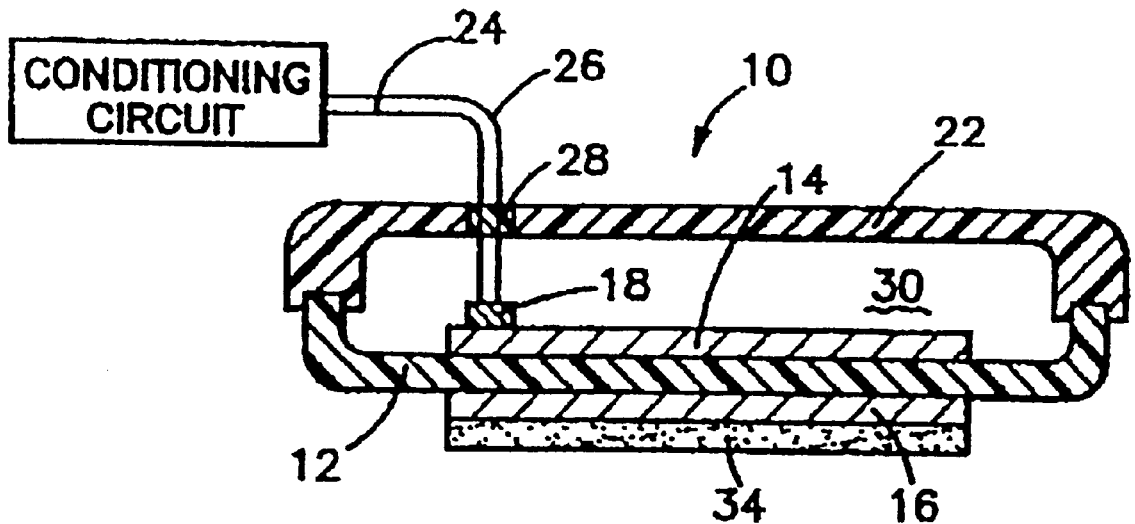
FIG. 3 is a schematic that depicts one form of a prior art piezoelectric film sensor useful in the invention.
Figure 4:
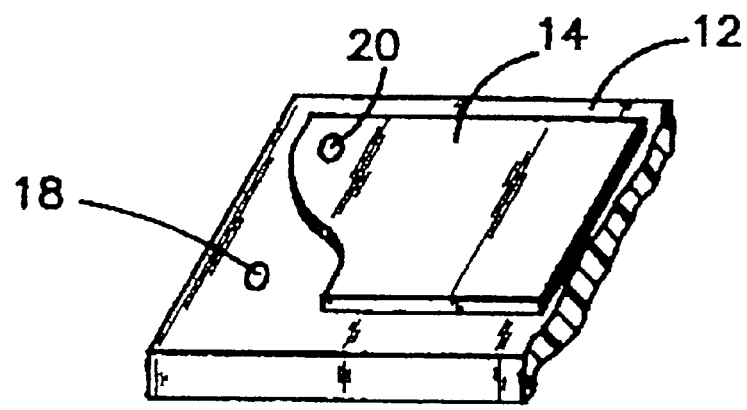
FIG. 4 illustrates a portion of the top surface of the sensor diaphragm of the FIG. 3 sensor.

One sensor of that type is illustrated by FIGS. 3 and 4 which are reproductions of FIGS. 1 and 2 of U.S. Pat. No. 5,365,937 with the associated element numerals. In the best mode embodiment of the invention, the sensor dimension width is less than one-half wavelength for the wavelengths (frequencies) of interest. This requirement provides a sensor dimension of less than one (1.0) centimeter in the direction of interest. The best mode includes contact pressure on the face of the sensor effective to cause a static deflection of the film of about one millimeter. The best mode further entails use of multiples of such sensors in an array configuration of nine or more elements or use of a preferred array configuration to enhance performance, the configuration including: (i) no three elements are along the same straight line (non-colinear); (ii) all elements are along the same straight line (colinear); or (iii) use of sub-arrays, in which the total number of sensors in an array is made up by use of a plurality of smaller arrays or pods.

Figure 5:
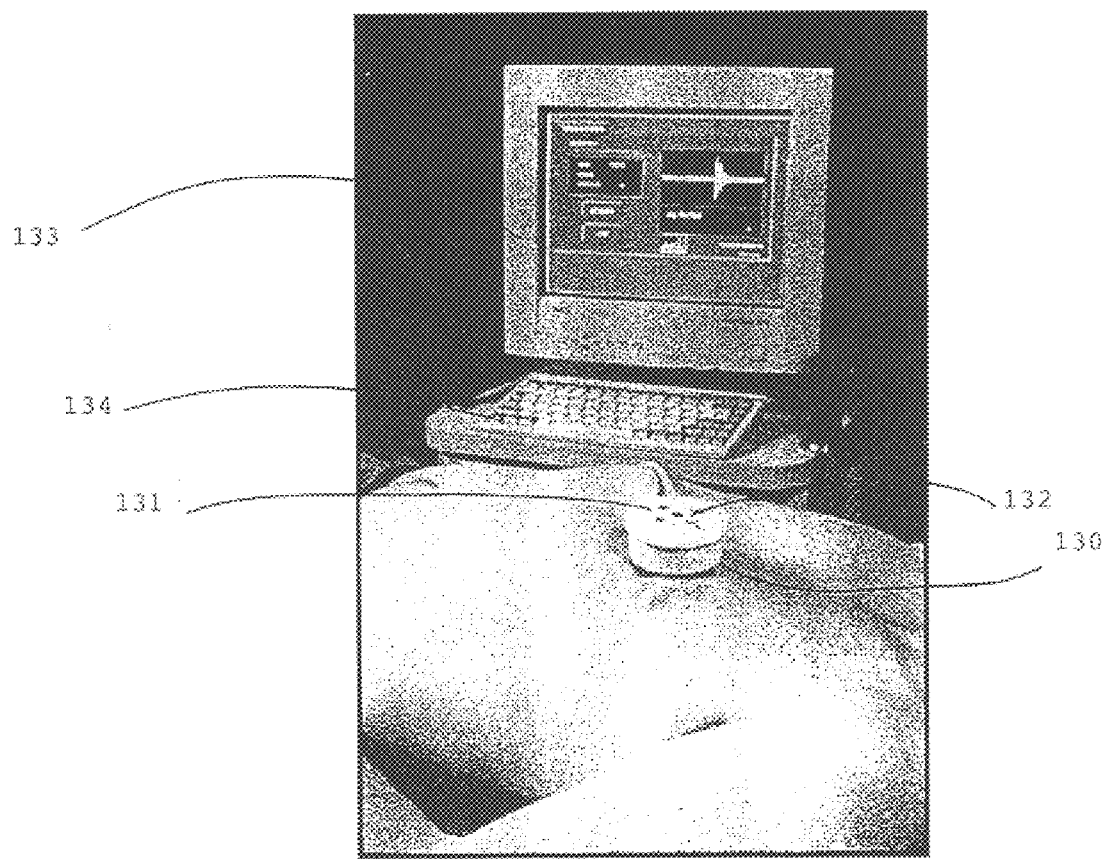
FIG. 5 depicts a five element preselected sensor array fixed in a device or pod positioned on the chest of a patient.

FIG. 5 illustrates a device 130 in which five sensors 131 (one of five sensors) are fixed in a preselected array in a device placed on the chest of the patient. The array includes a centrally positioned sensor 132 and four sensors illustrated generally by the single sensor 131 spaced from the central sensor 132. As shown in FIG. 5, the device 130 is operatively connected to a prototype acoustic imaging system of the invention including a computer monitor 133 and keyboard 134.

Figure 6:
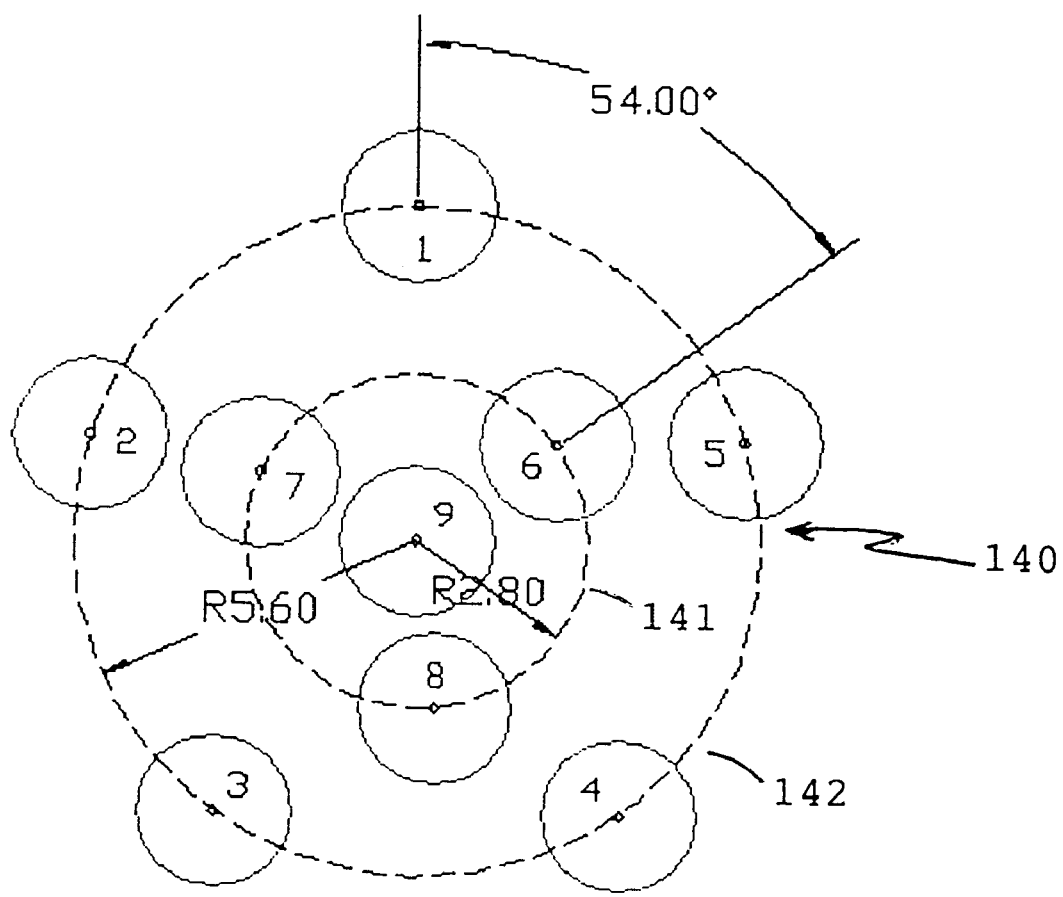
FIG. 6 illustrates a prior art nine sensor array with sensors positioned in two concentric circles. Sensors 1–5 are positioned in an outer circle, sensors 6–8 are positioned in a second circle and sensor 9 is positioned in the center of both circles.

Another useful prior art nine sensor array 140 as shown by FIG. 6 comprises eight equally spaced sensors in concentric circles 141, 142 having prime numbers of sensors in each circle. Specifically, five sensors are shown in circle 141 and three sensors are shown in circle 142. A ninth sensor is at the center of the circles. In FIG. 6 "R" means the radius of the relevant circle. Alternatively, the sensors may be positioned in a linear array.

3. The Acoustic Imaging System

An embodiment of the invention is a clinical workstation having an acoustic imaging system. The acoustic imaging system may amplify the signals from the sensors, convert the sensor data from analog to digital format and may store the information and process the data to enhance vascular sounds and display the information to the operator.

Figure 7:
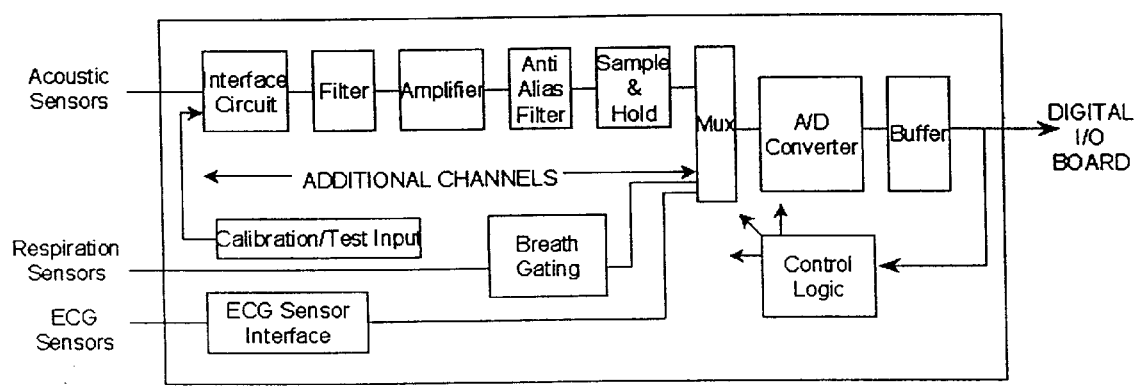
FIG. 7 is a schematic block diagram that depicts an arrangement of the components of one form of the acoustic imaging system of the invention.
Figure 8:
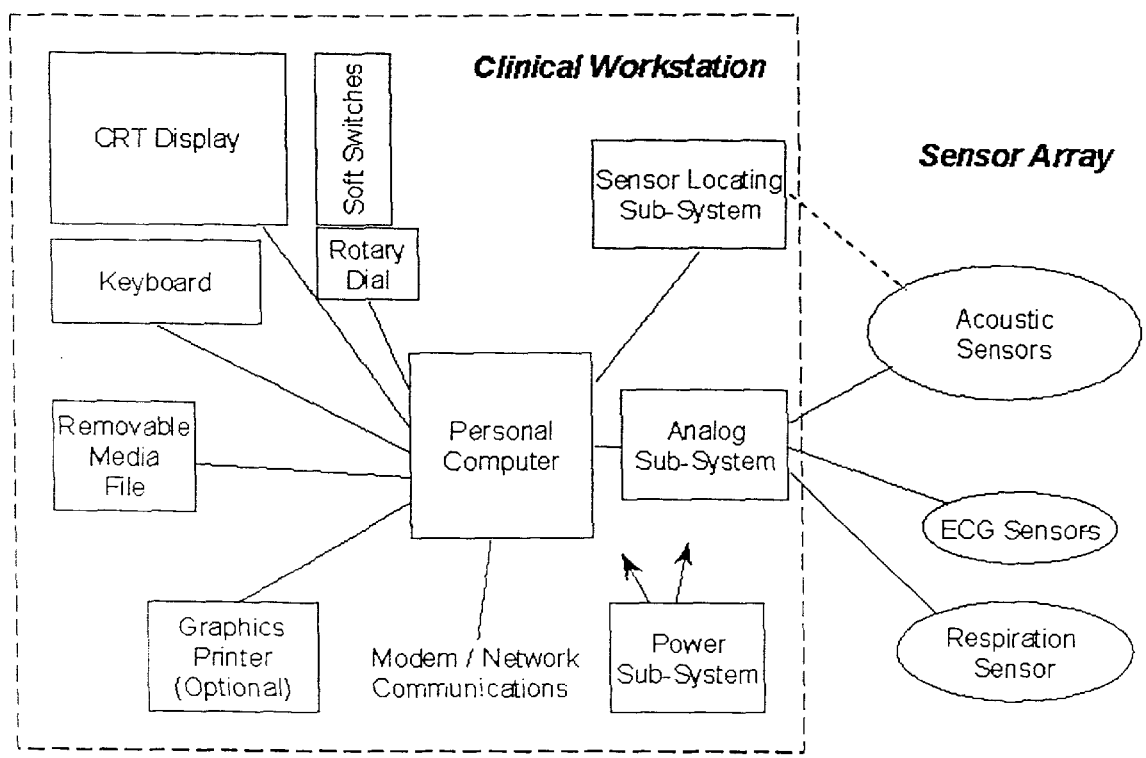
FIG. 8 is schematic block diagram that depicts an arrangement of the components of the clinical workstation of the invention.
Figure 9:
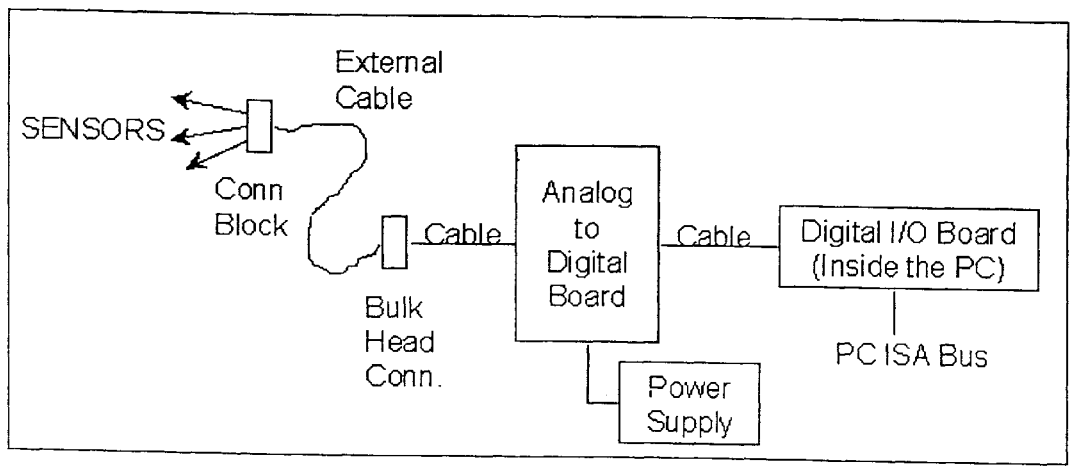
FIG. 9 is a schematic block diagram that depicts elements of the analog sub-system block of FIG. 8.

One configuration of the acoustic imaging system and the manner in which it is interfaced with the clinical workstation is illustrated in the block diagram FIGS. 7, 8 and 9, which show only those specific details that are pertinent to the present invention. The block diagrams are used to avoid obscuring the disclosure with details readily apparent to those skilled in the art. The block diagram illustrations and the image processing diagrams of the figures are primarily intended to illustrate the major components of the system in a convenient functional grouping.

Referring to FIG. 7, a conventional interface circuit and conventional filters, amplifiers, anti-alias filters, sample and hold and calibration/test input components are represented. The MUX box may include a standard channel to channel multiplexer. The ECG sensor interface may be an analog interface circuit suitable for the industry standard ECG sensor (three sensor inputs: plus, minus, ground) with one output. The output of the ECG sensor interface is provided as a channel input to the multiplexer such that when selected, the ECG sensor output may be converted by the analog to digital converter from an analog signal to a digital signal. As is further illustrated in FIG. 7, respiration sensor input is provided to a breath gating circuit which may be used to synchronize acquisition of acoustic and ECG data.

The control logic may include circuitry for (i) gain control (four stages), (ii) filter control (four stages), and (iii) calibration control (on/off). As is also illustrated in FIG. 7, additional channels may be provided to the multiplexer for input such as background noise or other analog inputs.

As seen in FIG. 7, an analog interface circuit selectively receives input from the acoustic sensors and from a calibration test input. The interface circuit provides the information to a filter which may be multiple pole high pass filter such as a Butterworth or other suitable filter. The output of the filter is amplified by amplifier and provided to an anti-alias filter which provides its output to a sample and hold circuit. The output of the sample and hold circuit is then provided to a channel to channel multiplexer the output of which is provided to an analog to digital converter. The output of the analog to digital converter is buffered and provided to a digital I/O board resident in the computer so as to allow for transmission of the digital data from the analog sub-system to the computer.

The FIG. 8 sensor locating sub-system supplies data to the computer to locate the center point of each of the acoustic sensors preferably to within ±1 mm in x, y, and z axes relative to one of the sensors designated as a reference point. This is preferably done automatically after the sensors have been placed on the patient's body surface and just before data acquisition. This sub-system may provide 16-bit A/D readings to the system. The reading will represent the acoustical and any ambient sensors (not shown) as well as feed back from the ECG leads. The software interface of this sub-system may be through low level device drivers (not shown) that communicate directly with the acoustic imaging device.

The workstation of FIG. 8 also includes an analog sub-system which receives the output of the acoustic sensors, the ECG sensors and the respiration sensor. The analog sub-system may process this information in analog format and provide the results to the personal computer or other data processing system.

The analog sub-system shown in FIG. 8 includes a digital I/O interface on the board to reduce noise. The digital I/O board may be a PC-DIO-24 board available from National Instruments Corporation, 6504 Bridge Point Parkway, Austin, Tex. 78730 or the STUDI/O board available from Sonorus, 111 East 12th Street, New York, N.Y. 10003.

The power sub-system illustrated in FIG. 8 may provide power to each of the components of the workstation. Also shown in FIG. 8 are a CRT display and optional printer for providing output to a user. Input devices such as a keyboard, rotary dial and soft switches may also be provided for receiving input from a user. A removable media file or other storage device may be utilized by the personal computer to store data as well as transfer data to other workstations.

The FIG. 8 power sub-system may be industry standard. Appropriate input power characteristics are:

Voltage −15 to +15 DC

Current 4 to 6 amps

Appropriate output power characteristics are:

Voltage 18 to 30 V

Current 2 Ma to 10 Ma

Ripple Less than one MV

The computer, including the CRT display and keyboard, preferably is an industry standard, e.g., IBM PC 365, Dell Optiplex GX Pro, Compaq, Desk Pro 6000.

FIG. 9 illustrates the interconnection of the external sensors, the analog subsystem, the power supply for the analog subsystem and the digital I/O board. As seen in FIG. 9, the sensors may be connected to the analog subsystem by a an external cable. Similarly, the analog sub-system, which may output digital data representative of the analog information presented to the analog sub-system, may be separate from the computer system and may be connected by an external cable to the digital I/O board in the computer which provides access to the data by the processor of the computer.

Alternatively, the analog sub-system may be incorporated in a computer or processing system utilized in a workstation according to the present invention.

The analog to digital board shown in FIG. 9 preferably has the characteristics set forth in Table 2:

TABLE 2

| Analog Inputs | | |
|---|---|---|
| Acoustic Channels | 31 | |
| ECG Channels | 1 (3 inputs) | |
| Digital Inputs (24 Bits) | Max | Min |
| Input logic high voltage | | |
| Input logic low voltage | | |
| Input Current | | |
| Digital Outputs (24 Bits) | Max | Min |
| Output high voltage (Iout = −2.5 mA) | | |
| Output low voltage (Iout = +2.5 mA) | | |
| Output current (Vol = 0.5 V) | | |
| Output current (Voh = 2.7 V) | | |
| Power | | |
| Typical | | |
| Maximum | | |
| Physical | | |
| Size | | |
| Construction | 2 signal layers | |
| | Power plane | |
| | Ground plane | |

Figure 10:
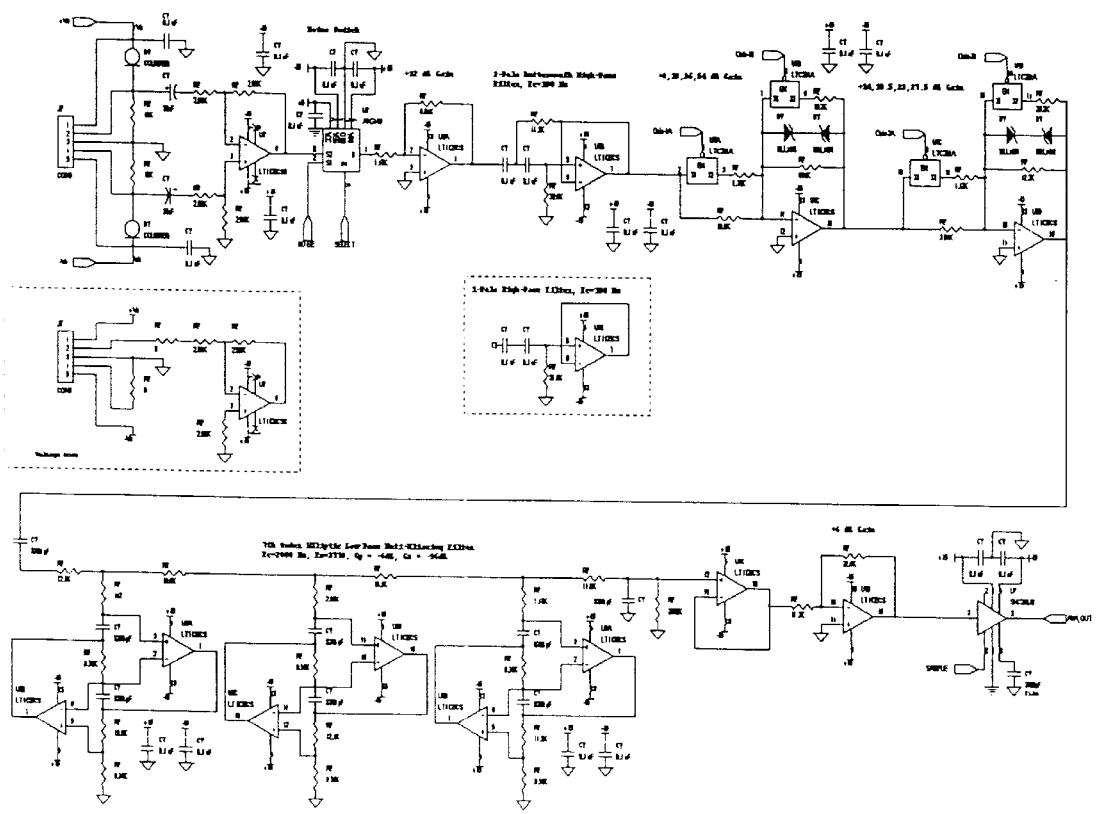
FIGS. 10 and 11 are circuit diagrams for the digital I/O Board shown in FIG. 9.
Figure 11:
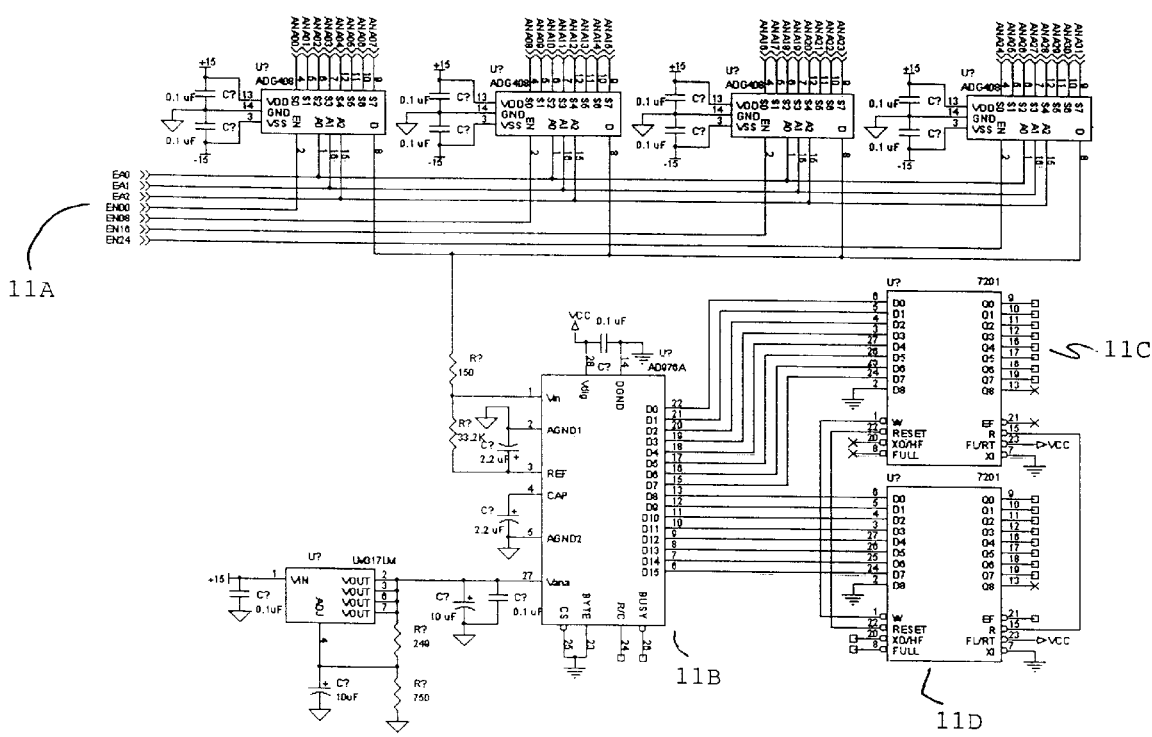

FIGS. 10 and 11 are circuit diagrams for the digital I/O Board shown in FIGS. 8 and 9.

FIG. 10 depicts one of the 32 analog channels that condition the array signals prior to digital conversion. FIG. 11 shows the termination of each of these analog channels as input along the top of the figure as 'ANAxx', into sample-and-hold buffers. Along the left side of FIG. 11 are the seven digital input "data request" lines 11A from the FIG. 8 computer.

Upon request from the PC, the analog data from each channel is routed from the sample-and-hold buffer to the analog-to-digital converter (A/D Converter of ADC), which is the large chip 113 at the bottom center of FIG. 11.

The final two chips 11C and 11D at bottom right of FIG. 11 are digital buffers for output to the PC.

4. Procedure for Use of The Clinical Workstation

This section of this specification provides an overview of how the acoustic imaging system may be used. Although these steps may not always be performed according to the stated sequence, this order is presently preferred.
(a) Power on the System The power switch (not shown) is located on the front of the Clinical Workstation along with a light (color as required by standards) to indicate that the unit is turned on. The power switch turns on/off the entire system. It may be covered or recessed to prevent inadvertent operation. The system may execute a self-test each time it is powered on. The self-test sequence completes with an indication that the system is ready to use.
(b) User Controls User controls may include a computer keyboard, rotary dial with push button action and "soft keys" that can be "labeled" by information on the display screen. The user access may be limited to only the menus and modes of operation that are part of the acoustic imaging system operation. Except in special modes that are restricted to authorized persons, the operator may not be able to access the operating system, alter system files or perform any other computer operations.
(c) Enter Patient Information Patient information, such as name, ID number, date of birth, study number, referring physician's name and user's name, is entered. Additionally, a fixed length comment can be provided. All of the entered information appears on the screen to be verified by the user. The acoustic imaging system software may provide a template to guide the operator through the process of entering patient information. These templates may be field adjustable for each institution.
(d) Patient Preparation This step requires positioning the patient, preparing the chest or other body surface, placing the sensor array and connecting the ECG leads, and verifying the signals. The patient may be instructed on protocols for breathing during the test, including exhaling and holding their breath in cooperation with the operator.
(e) Acquire Patient Test Data The operator may have the capability to enter an acquisition comment such as the reason for the test (pre-intervention, post-intervention, office exam, etc.). The system may record the time and date of each acquisition automatically.

The instrument may provide feedback to guide the operator in each step, such as determining sensor array placement, indicators for sensor contact, and gain settings. Preferred embodiments may provide real-time feedback for the operator during the data acquisition interval to ensure proper system function.

The instrument may store acquired data over a defined interval, e.g., a 30-second to 15-minute interval. Any aberrant system condition is also stored. The data stored may contain a record which can be mapped to the system's time base. The instrument preferably includes means to internally retain patient records.

In addition to the patient data, the system may maintain a master log of summary information (date, time, patient identification, operator identification of all tests run and all error conditions) in a file that is password protected and can be accessed, copied and deleted only by authorized persons.
(f) Display Pre-Processed Data Prior to releasing the patient and immediately after data acquisition, the workstation may apply a fast executing (less than three minutes) algorithm which demonstrates the integrity of the collected signal.
(g) Process Data The system may automatically process patient data in the order collected unless prioritized by the operator. The workstation may execute the analysis based on a predefined protocol, providing a graphical progress (completion time) indicator while the processing is underway. At the conclusion of the processing, a copy of the patient's record may be archived to a removable storage medium by the operator, and the software may mark that record as archived. The system may indicate if the storage medium is full and also warn the operator of an attempt to delete a record that has not been previously archived.
(h) Display Output The workstation may provide the capacity to display and interact with the data in the following ways, among others:
  Display 2-D sliced views through the data volume with a goal to display 3-D volumetric rendering with sectional planes
  Display 3-D volumetric data rendered using an alpha-curves to control voxel translucency
  Zoom a slice (reprocess the data to gain better spatial resolution)

Annotate the images

Display raw sensor and ECG data

Display phonocardiographic data

Select a specific interval/frame

Change the color map

Select a frequency-domain filter (band selection)

Save the generated image plus the accompanying analysis

Print the images including patient information (system option).

4. Data Acquisition and Processing Beamformers

Near field conventional beamformers may be used in the practice of the invention. However, the invention includes a novel adjustable gain/resolution beamformer to provide a more focused beam steering angle.

(a) Near Field Conventional Beamformer

Vector formulation and matrix formulation are the two main types of procedures applicable to image flows using conventional beamformers in visco-elastic media. Both types of procedures may be used to implement a Bartlett beamformer. Vector formulation may also be used to implement a simple advance and sum beamformer.

1. Vector Formulation:

A matrix with as many columns as channels and as many rows as there are frequency bins within the desired frequency range is provided by ensemble averaging the sensor signals in the frequency domain with the spectra truncated to contain only the frequencies of interest. This matrix is shown by Equation 1:

$$FFT_v = \begin{bmatrix} B_{start\_freq\_bin,1} & \cdots & B_{start\_freq\_bin,num\_receivers} \\ \vdots & \ddots & \vdots \\ B_{end\_freq\_bin,1} & \cdots & B_{end\_freq\_bin,num\_receivers} \end{bmatrix}$$

Equation 1

Next, for every point on a three dimensional grid, the given dispersion relation (frequency/velocity relationship) and the array geometry are used to compute a set of inverse path models at each location in three dimensional space. The origin and orientation of the coordinate system used is arbitrary. Typically, the coordinate system is normalized to be a right handed coordinate system with the location of the receiver closest to the center of the array used as the origin and with the positive x axis in the direction of the patients head and the positive z axis into the body. The inverse path model matrix (IPM) is shown by Equation 2:

$$IPM(\vec{x}) = \begin{bmatrix} I_{start\_freq\_bin,1}(\vec{x}, \omega) & \cdots & I_{start\_freq\_bin,num\_receivers}(\vec{x}, \omega) \\ \vdots & \ddots & \vdots \\ I_{end\_freq\_bin,1}(\vec{x}, \omega) & \cdots & I_{end\_freq\_bin,num\_receivers}(\vec{x}, \omega) \end{bmatrix}$$

where:

$$I_{bin,rec}(\vec{x}, \omega) = \cos\left(\frac{|\vec{x} - \vec{r}_{rec}| \cdot \omega}{c(\omega)}\right) + i \cdot \sin\left(\frac{|\vec{x} - \vec{r}_{rec}| \cdot \omega}{c(\omega)}\right)$$

and $C(\omega)$ is the dispersion relationship, and $\vec{r}_{rec}$ is the position of a particular receiver.

Equation 2

Finally, the beamformer output is computed by summing the scalar product of the ensemble averaged receiver signals matrix and the inverse path model matrix across channels thereby producing a row vector with as many complex elements as there were frequency bins. The complex magnitude of the elements is then summed across frequency bins yielding the beamformer output at the specified location. This is shown by Equation 4. First compute the scalar product of the inverse path model and the signal matrix:

$$M(\vec{x}) = FFT_v \cdot IPM(\vec{x})$$

Equation 3

Now compute the beamformer output:

$$B_{output}(\vec{x}) = \sum_{bin=start\_freq\_bin}^{end\_freq\_bin} \left| \sum_{rec=1}^{num\_receivers} M_{bin,rec}(\vec{x}) \right|$$

Equation 4

Using the conventional beamformer in four dimensions with the fourth dimension being speed, c, is exactly the same except that the c is no longer assumed to simply have a known functional relationship to frequency. Hence, IPM in Equation 2 becomes a function of both position and speed. In four dimensions, IPM is a function of speed as well as position:

$$M(\vec{x}, c) = FFT_v \cdot IPM(\vec{x}, c)$$

Equation 5

This functional relationship propagates through the equations as shown by Equation 6. Now compute the beamformer output:

$$B_{output}(\vec{x}, c) = \sum_{bin=start\_freq\_bin}^{end\_freq\_bin} \left| \sum_{rec=1}^{num\_receivers} M_{bin,rec}(\vec{x}, c) \right|$$

Equation 6

2. Matrix Formulation:

For the matrix formulation of the conventional beamformer the receiver signals are first ensembled to form an R matrix at each frequency. The R matrix may be the cross spectral density matrix. Alternatively, interchannel phase difference matrices may be produced. No matter which method is used to form the matrices, the beamforming process remains the same. As with the vector formulation, these matrices are only formed at the frequencies of interest. The general form of the set of R matrices is given by Equation 7:

$$R_M(\omega) = \begin{bmatrix} B_{1,1} & \cdots & B_{1,num\_receivers} \\ \vdots & \ddots & \vdots \\ B_{num\_receivers,1} & \cdots & B_{num\_receivers,num\_receivers} \end{bmatrix}$$

Equation 7

Just as in the vector formulation, to beamform, the matrix formulated must have inverse path model information. For the matrix formulation, the inverse path model information is contained in steering vectors. Steering vectors are computed for each frequency and position in three dimensional space just as the inverse path models were in the vector formulation. However, steering vectors are computed across channels whereas the inverse path models in the vector formulation were computed across frequencies. The difference is merely a matter of when the values are computed and how they are organized. The actual value for any given position, array geometry, speed, and frequency are the same in either formulation. Equation 8 shows this different arrangement:

$$S(\vec{x},\omega)=[I_1(\vec{x},\omega) \ldots I_{num\_receivers}(\vec{x},\omega)]$$

where:

$$I_n(\vec{x}, \omega) = \cos\left(\frac{|\vec{x}-\vec{r}_n|\cdot\omega}{c(\omega)}\right) + i \cdot \sin\left(\frac{|\vec{x}-\vec{r}_n|\cdot\omega}{c(\omega)}\right)$$

and where $C(\omega)$ is the dispersion relationship and $\vec{r}_n$ is the location of the nth receiver.

Equation 8

Once the R matrices and the steering vectors have been computed, the beamformer output can be computed. This is the sum across all of the frequencies of interest of the beamformer output for the given position in three dimensional space. This is shown by Equation 9:

$$B_{output}(\vec{x}) = \sum_{bin=start\_freq\_bin}^{end\_freq\_bin} \frac{S(\vec{x}, \omega_{bin})^H R_M(\omega_{bin}) S(\vec{x}, \omega_{bin})}{S(\vec{x}, \omega_{bin})^H S(\vec{x}, \omega_{bin})}$$

Equation 9

Following the exact same logic used in vector formulation, moving to four dimension in the matrix formulation means that no particular functional relationship between speed and frequency is assumed. Thus, speed (c) becomes fourth dimensional as shown below by Equation 10:

$$B_{output}(\vec{x}, c) = \sum_{bin=start\_freq\_bin}^{end\_freq\_bin} \frac{S(\vec{x}, \omega_{bin}, c)^H R_M(\omega_{bin}) S(\vec{x}, \omega_{bin}, c)}{S(\vec{x}, \omega_{bin}, c)^H S(\vec{x}, \omega_{bin}, c)}$$

Equation 10

3. Summary Regarding Vector and Matrix Formulation:

Either vector or matrix formulation beamforming may be used according to the present invention. Vector formulation requires fewer operations and is preferred. To compute the same frequency in using the matrix formulation requires one hundred ninety nine floating point operations (FLOPS). For the vector formulation, the FLOPS go up linearly with the number of array elements. For the matrix case, the number of FLOPS goes up as the square of the number of array elements.

Figure 12:
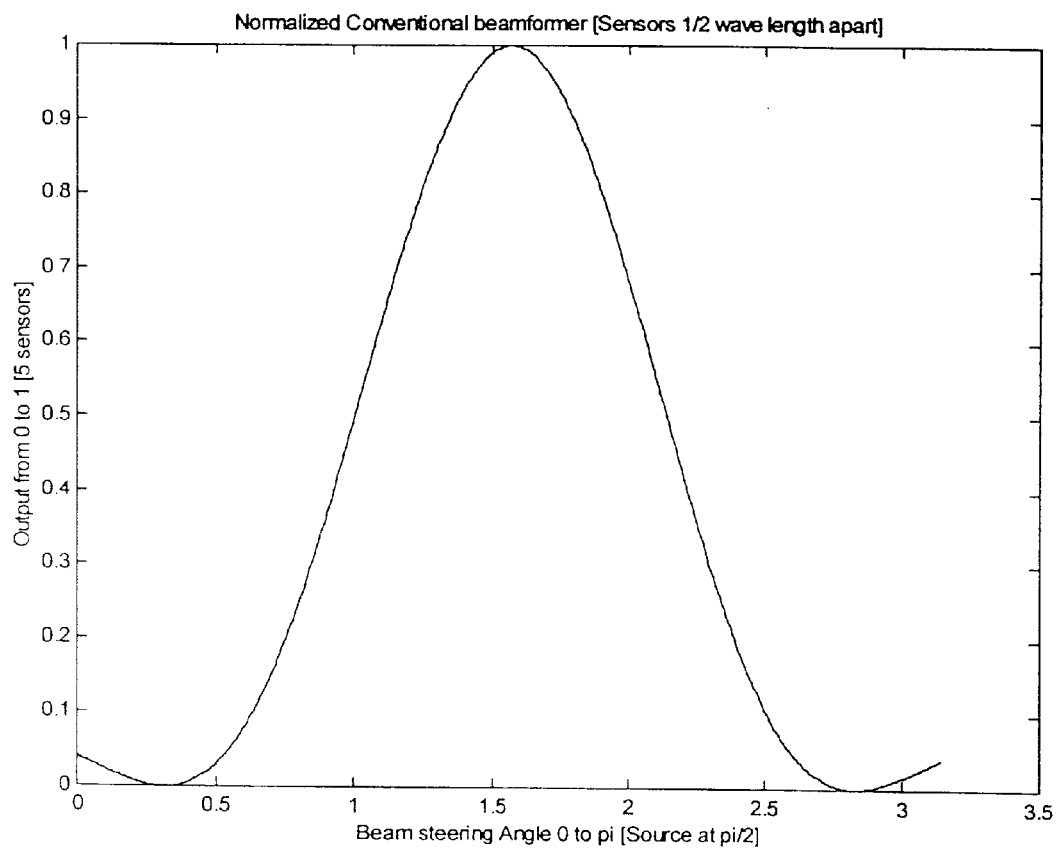
FIG. 12 is a plot of the beam steering angle 0 to $\pi$ of a normalized conventional beamformer, no null steer as a function of output 0 to 1 from 5 sensors one-half wave length apart. Source at $\pi/2$.
Figure 13:
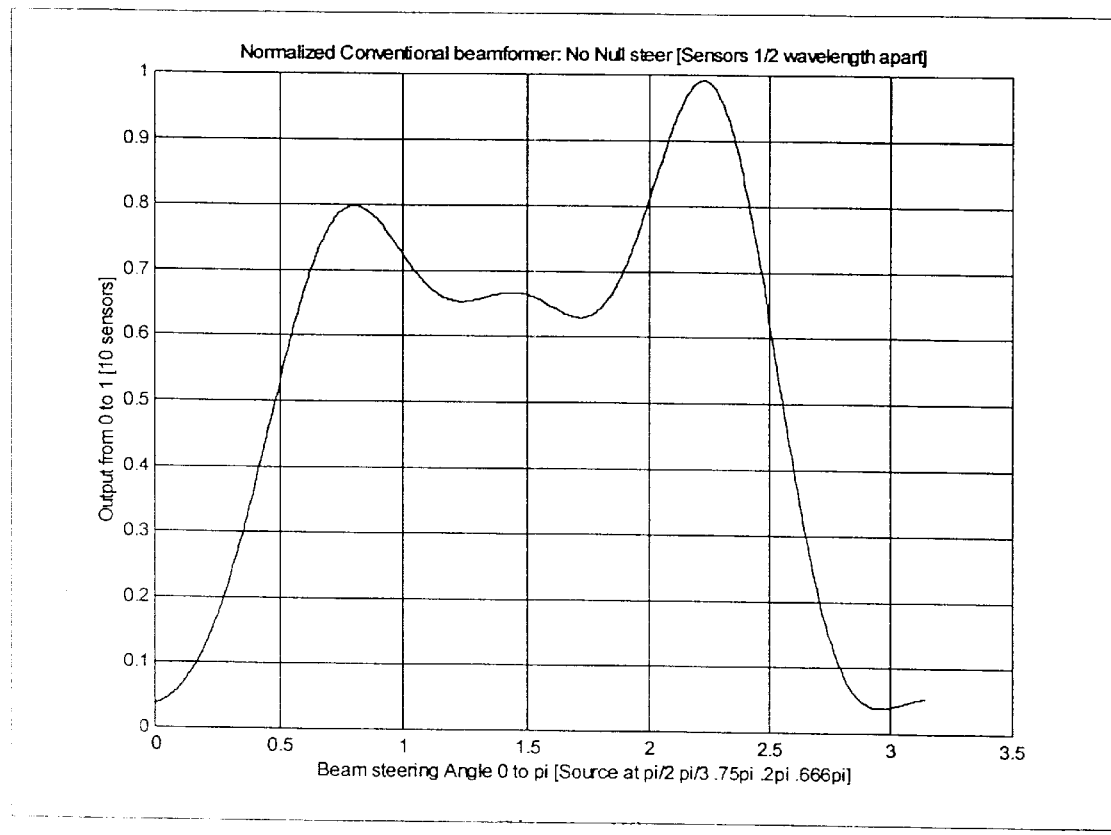
FIG. 13 is a plot of the beam steering angle 0 to $\pi$ of a normalized conventional beamformer, no null steer as a function of output 0 to 1 from 10 sensors one-half wavelength apart. Source at $\pi/2$; $\pi/3$, $0.75\pi$, $0.2\pi$, and $0.666\pi$.

FIGS. 12 and 13 are plots of a normalized conventional beamformer steering angle, at indicated source locations, as a function of the output from 0 to 1 of five (FIG. 12) and 10 (FIG. 13) sensors spaced one-half wave length apart. As FIGS. 12 and 13 indicate, conventional beamformers provide a relatively wide beam or broadly focused steering angle.

(b) Adjustable Gain/Resolution Null Space Beamformer

Figure 14:
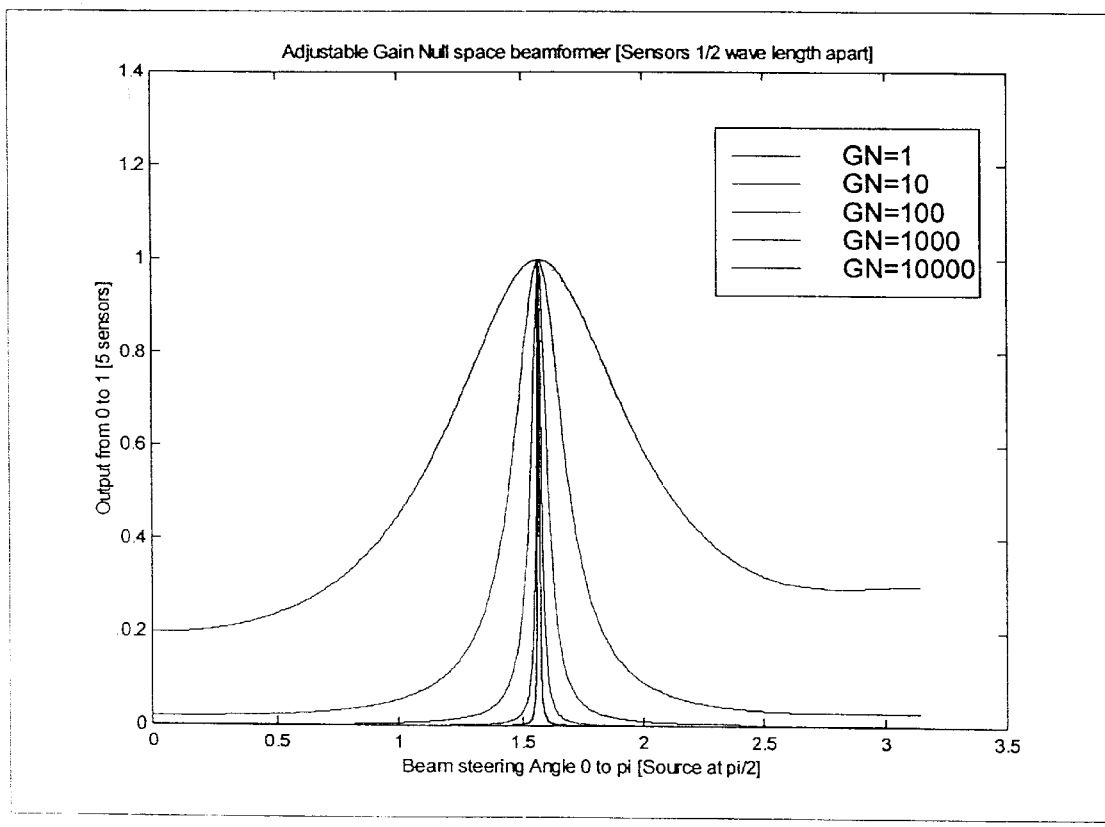
FIG. 14 is a plot of the beam steering angle 0 to $\pi$ of an adjustable null space beamformer as a function of output from 0 to 1 from five sensors spaced one-half wavelength apart. GN (gain) 1, 10,100, 1000 and 10,000. Source at $\pi/2$.
Figure 15:
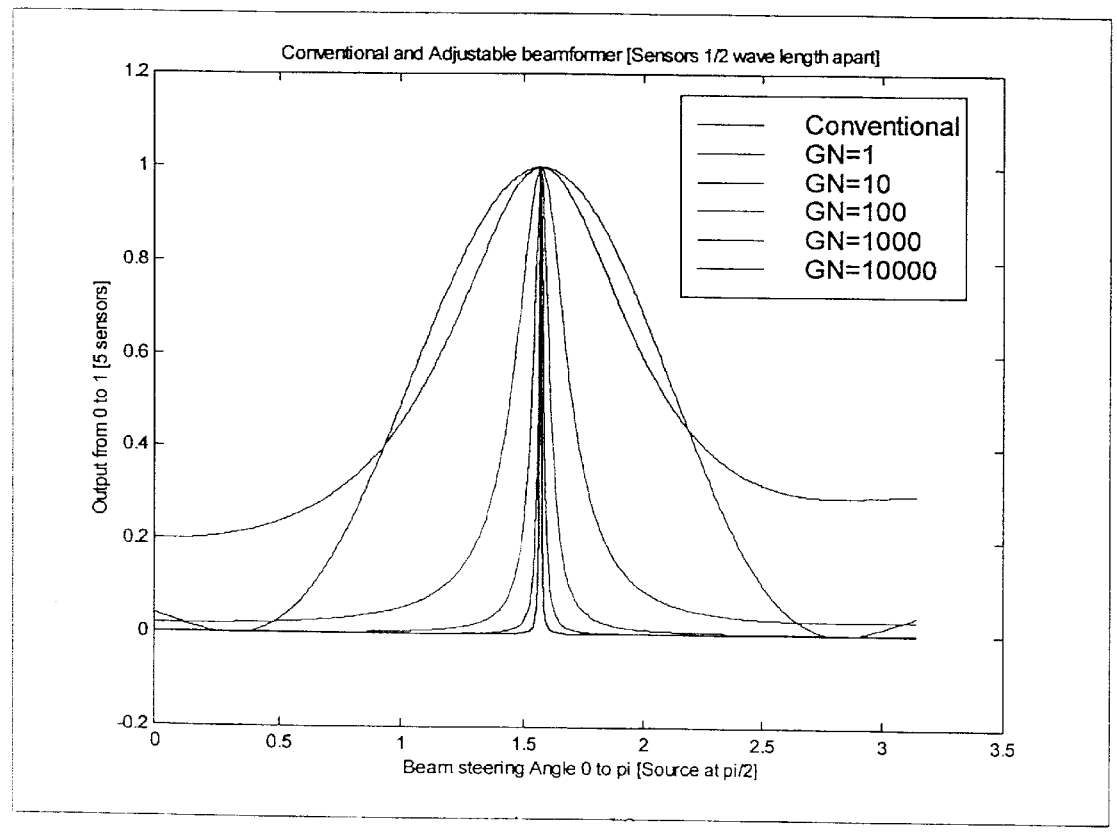
FIG. 15 is a plot comparing the beam steering angles of a conventional and an adjustable null space beamformer as a function of output from 0 to 1 from five sensors spaced one-half wavelengths apart at GN 1, 10, 106, 1000 and 10,000.

Adjustable gain resolution null space beamformer beam steering angles are more focused or acute. See the FIG. 14 plot of the beam steering angle of an adjustable null space beamformer and the FIG. 15 comparison of the beam steering angle of a conventional and adjustable beamformer.

One set of operations using an adjustable gain/resolution null space beamformer to acquire and process abnormal blood flow noise and image turbulent blood flow may include:

(1) Positioning an array of sensors on an area above a volume of space in a patient's body which may include a stenosis.

(2) Generating a three dimensional (x,y,z) grid as defined above of potential stenosis locations in the volume of the patient's body space below the sensor array.

The uniformly spaced three dimensional grid is generated by evenly dividing a three dimensional region of space into Nx, Ny, and Nz points along and perpendicular to the Cartesian axes X, Y and Z respectively. This space has dimensions in X, Y and Z of delx, dely, and delz, respectively and is offset below the array by a vector O. By varying O, delx, dely and delz, the size, shape and location of the volume of interest and the density of points in physical space can be adjusted.

(3) Determining the location on the x,y,z grid of the centers of contact on the patient's body of each of the sensors in the array. The location of the x, y z grid of the centers of contact on the patient's body for each of the sensors may be determined using stereo photogrammetry. See Horn, Berthold, Klaus, Paul, *Robot Vision*, Cambridge, Mass., MIT Press, 1986, pp. 311, 312. See, e.g., FIGS. 2A and 2B which depict means 120 and 122 for mounting two charge coupled device (CCD) cameras. Preferably the cameras are rigidly mounted 18 inches apart with a convergence angle of 45 degrees. The spacing of the cameras and the convergence angle may be varied by the operator. Images of the sensor array are simultaneously acquired by each camera, processed, and analyzed to provide an n-by-3 matrix of sensor positions on the patient's chest.

Retro-reflective tape is affixed to the sensor tops and illuminated with infrared (IR) light emitting diodes (LEDs) mounted around each camera's lens. To facilitate segmentation by increasing the image contrast, an infrared filter is mounted in front of the camera lens. The filter allows the reflected IR light to pass through to the camera sensor while reducing the amount of visible light entering the lens.

After segmentation, features corresponding to sensors in each image are analyzed using a connected component labeling algorithm. See Connected Component Labeling", Haralick, Robert M. and Shapiro, Linda G., *Computer and Robot Vision*, Addison-Wesley Publishing Co., New York, N.Y., pp. 31–40. From the labeled image, the area, first moments, and second moments are derived for each connected component. Sensor feature area and first moments are used to determine location. The sensor feature area and second moments are used to determine orientation. After the position of each sensor feature has been determined, correspondence between said features in each image is established. Then using the coordinates of each sensor feature in both the left and right images, the x, y, z positions of the sensor tops are calculated with respect to the left camera with the following equations 11 and 12:

$$z_1 = \frac{-b\left(\frac{x'_r}{f_r}\sin\theta + \cos\theta\right)}{\left(\frac{x'_r}{f_r} - \frac{x'_l}{f_l}\right)\cos\phi - \left(1 + \frac{x'_r x'_l}{f_r f_l}\sin\phi\right)}$$

Equation 11

$$\begin{bmatrix} x_1 \\ y_1 \\ z_1 \end{bmatrix} = z_1 \begin{bmatrix} \frac{x'_1}{f_1} \\ \frac{y'_1}{f_1} \\ \frac{f_1}{f_1} \\ 1 \end{bmatrix}$$

where:

$X'_l$ is the x-coordinate in the left image, $x'_r$ is the x-coordinate in the right image, $y'_l$ is the x-coordinate in the left image, $y'_r$ is the y-coordinate in the right image, $X_t$ is the x-coordinate of the sensor, $y_t$ is the y-coordinate of the sensor, $f_l$ is the left focal length, $f_r$ is the right focal length, b is the distance between cameras θ is the convergence angle, and φ is θ/2.

Equation 12

Because each sensor top is assumed to be circular, the image of each sensor is an ellipse. Using the position of the ellipse, the orientation and the area, sensor positions on the patient's body surface are determined.

(4) Determining the distance to each location point on said grid from the center of contact of each sensor on the body surface of the patient. The distances are determined by computing the Pythagorean distances from each sensor location to each grid location. The resulting distances are stored in a matrix with as many rows as there are grid locations (Nx+Ny+Nz) and as many columns as there are sensor elements. The equation is given below:

$$D_{g,r} = \sqrt{(x_g - x_t)^2 + (y_g - y_t)^2 + (z_g - z_t)^2}$$

where:

g={1,2,3, . . . (Number of Grid Points)}
r={1,2,3, . . . (Number of Sensors)}

Equation 13

(5) Concurrently acquiring data in one pass from the positioned sensors and from ECG over several heart beats. Specifically:

(i) first pass broad band low gain for S1 and S2 heart sounds;

(ii) second pass high pass filtered high gain data for turbulent blood flow signals.

(6) Parsing the concurrently acquired step (5) data into three time periods, i.e., S1 and S2 heart sounds and a quiet interval where blood flow through the artery is at its peak.

(7) Determining the shear wave phase angle shift from each sensor contact center to each location on the three dimensional grid of step (2).

The phase angle shift may be determined from a priori knowledge of shear wave speed in the body as a function of the frequency. See, Verburg, J., Transmission of Vibrations of the Heart to the Chest Wall. Advanced Cardiovascular Physics, Vol. 5 (Part III), pp. 84–103 (1983).

Alternatively, the phase angle shift may be determined de novo by methods such as those described in Oestreicher, H. L., Field and timpedance of an Oscillating Sphere in a Viscoelastic Medium with an Application to Biophysics, *J. Acoust. Soc. Am.* (1951) 23:707–714; von Glerke, H., et al., Physics of Vibrations in Living Tissues, *J. Appld. Physiology* (1952), 886–900.

(8) Determining an inverse path model (as one steering vector parameter) from each sensor contact center to each location point on the three dimensional grid. Given the distance from the center of contact for each sensor to each grid location and the shear wave speed in the medium, an inverse path model can be computed from each sensor to each grid point. The equation describing this inverse path model is given below:

$$\tilde{p}_{g,r}^{-1}(\omega) = \cos\left(\frac{D_{g,r}\omega}{c(\omega)}\right) + i\sin\left(\frac{D_{g,r}\omega}{c(\omega)}\right)$$

where:

g={1,2,3, . . . (Number of Grid Points)}
r={1,2,3, . . . (Number of Receivers)}

Equation 14

The phase angle shift determined in step (7) is assigned a complex weight of magnitude one.

(9) Forming an inverse path model (steering vector) matrix for each frequency of interest and for each location of interest.

The inverse path model matrix comprises a plurality of steering vectors in which (i) each vector is composed of the scalar inverse path models from each sensor to a grid point;

(ii) the length of each vector is the number of sensors in the array; and (iii) the number of vectors in the matrix is the number of interior points on the 3-D grid of step (3).

(10) At each peak arterial blood flow period as determined above (i) taking sliding windows across all sensor data channels; and (ii) taking a FFT of the windowed data in known manner.

(11) Computing an interchannel phase difference matrix (R matrix) for each frequency of interest corresponding to those used when forming the steering vectors in step (9) and for each sliding window of data taken in step (10). These matrices, as computed at each frequency of interest and for each data window from step (10) are averaged to form an ensemble interchannel phase difference matrix for each frequency.

Interchannel phase difference matrices are formed at each frequency by creating a vector v, of the complex FFT outputs across all channels at that particular frequency. Next, instead of forming the outer product as is done when forming the Cross Spectral Density matrices, the entire vector (each element) is divided by the element which is being used as the reference channel, $v_o$. The selection of the reference channel is made easier by choosing the channel which has the highest variance. Choosing the channel with the highest variance and therefore the highest combined signal and noise increases the likelihood that the reference channel is the channel with the highest signal to noise ratio. Once the entire vector has been divided by the reference channel, all phase values represent the interchannel phase difference between each channel and the reference channel. The entire vector is multiplied by the magnitude of the reference channel to form the outer product of the vector which is the interchannel phase difference matrix for that frequency. The relevant Equations 15 and 16 are shown below:

$$v_{icd}(\omega) = |v_{ref}(\omega)| \frac{\overline{v}(\omega)}{v_{ref}(\omega)}$$

Equation 15

$$V_{icd}(\omega) = V_{icd}^* V_{icd}$$

where:

is the interchannel difference vector at this frequency, $V_{ref}(\omega)$ is the scalar complex value of the reference channel FFT, and $V_{icd}(\omega)$ is the interchannel difference matrix at this frequency.

Equation 16

(12) Decomposing the step (11) interchannel phase different R matrix into its eigenvalues and eigenvectors. This step is accomplished in known manner. See, e.g., Galoub and Van Loan, Matrix Computations (1989), Johns Hopkins University Press.

(13) The previous step decomposed the R matrix into its eigenvalues and eigenvectors, which can be expressed as shown below for a 3×3 matrix.

$$R = \begin{vmatrix} v_{11} & v_{12} & v_{13} \\ v_{21} & v_{22} & v_{23} \\ v_{31} & v_{32} & v_{33} \end{vmatrix}^H \begin{vmatrix} \sigma_1 & 0 & 0 \\ 0 & \sigma_2 & 0 \\ 0 & 0 & \sigma_3 \end{vmatrix} \begin{vmatrix} v_{11} & v_{12} & v_{13} \\ v_{21} & v_{22} & v_{23} \\ v_{31} & v_{32} & v_{33} \end{vmatrix}$$

Equation 17

The eigen values of the 3×3 R matrix are: $\sigma_1 \geq \sigma_2 \geq \sigma_3$. Equation 18 associates the eigen values with their respective eigen vectors:

$$ev_1 = \begin{vmatrix} v_{11} \\ v_{21} \\ v_{31} \end{vmatrix}, ev_2 = \begin{vmatrix} v_{12} \\ v_{22} \\ v_{32} \end{vmatrix}, ev_3 = \begin{vmatrix} v_{13} \\ v_{23} \\ v_{33} \end{vmatrix}$$

Equation 18

The classical definition of the inverse R expressed by its eigenvalues and eigenvectors is shown below. Note that the superscript H denotes the conjugate transpose.

$$R^{-1} = \begin{vmatrix} v_{11} & v_{12} & v_{13} \\ v_{21} & v_{22} & v_{23} \\ v_{31} & v_{32} & v_{33} \end{vmatrix} \begin{vmatrix} \frac{1}{\sigma_1} & 0 & 0 \\ 0 & \frac{1}{\sigma_2} & 0 \\ 0 & 0 & \frac{1}{\sigma_3} \end{vmatrix} \begin{vmatrix} v_{11} & v_{12} & v_{13} \\ v_{21} & v_{22} & v_{23} \\ v_{31} & v_{32} & v_{33} \end{vmatrix}^H$$

Equation 19

A problem may arise if any of the eigenvalues are equal to or close to zero because this causes the corresponding diagonal elements to go to infinity. The usual solution is not to include that eigenvector and eigenvalue in the R inverse formulation. This creates another problem if R inverse is used in a reciprocated form such as a beamformer because beamformer has the form:

$$B_{Output\ in\ power} = \frac{1}{S^H R^{-1} S},$$

Equation 20

Thus, if the steering vector S to the desired location is identical to one of the deleted eigenvectors, then the beamformer output goes to infinity. This is not the right answer.

One method to avoid these problems is to partition the R inverse into two parts. One part uses the dominant eigenvalues and eigenvectors the other part represents the null space of the matrix R. As an example, for the 3×3 R matrix with one dominant eigenvalue, the following would be an estimate to the inverse:

$$R^{-1} = \begin{vmatrix} v_{11} \\ v_{21} \\ v_{31} \end{vmatrix} \begin{vmatrix} \frac{1}{\sigma_1} \end{vmatrix} \begin{vmatrix} v_{11} \\ v_{21} \\ v_{31} \end{vmatrix}^H + GN \begin{vmatrix} V_{12} & v_{13} \\ v_{22} & v_{23} \\ v_{32} & v_{33} \end{vmatrix} \begin{vmatrix} 1 & 0 \\ 0 & 1 \end{vmatrix} \begin{vmatrix} V_{12} & v_{13} \\ v_{22} & v_{23} \\ v_{32} & v_{33} \end{vmatrix}^H$$

Equation 21

GN is an arbitrary number that controls the effect of the null space on the inverse. In general, the two parts to the inverse can be defined for a N×N matrix with k dominant eigenvalues. See equations 22 and 23.

$$R_S = |ev_1 \ \Lambda \ ev_k| \begin{vmatrix} \frac{1}{\sigma_1} & 0 & 0 \\ 0 & O & 0 \\ 0 & 0 & \frac{1}{\sigma_3} \end{vmatrix} |ev_1 \ \Lambda \ ev_k|^H$$

Equation 22

$$R_N = |ev_{k+1} \ \Lambda \ ev_n| \begin{vmatrix} 1 & 0 & 0 \\ 0 & O & 0 \\ 0 & 0 & 1 \end{vmatrix} |ev_{k+1} \ \Lambda \ ev_n|^H$$

Equation 23

So the inverse can be expressed as:

$$R^{-1} = R_S + GN \cdot R_N$$

Equation 24

(14) By using the inverse developed above the beamformer output can be written as:

$$B_{Output\ in\ power} = \frac{1}{S^H R_S S + GN \cdot S^H R_N S}$$

Equation 25 where S is the steering vector and GN is the gain on the null space of the beamformer output. Low GN widens the beam width. High GN narrows the beam width.

(15) The value of the step (14) beamformer output is associated with the 3-D location and the results displayed with a volumetric imager.

Any commercially available volumetric imager may be used.

(16) Inspecting the step (15) image to determine the need for compression energy suppression. Absent such need, the image is complete.

6. Compression Energy Suppression Beamformers

The formation of acoustic images of turbulent blood flow signals may be enhanced by elimination or reduction of the effects of compressional waves relative to shear waves or any other waves arriving at the sensor array. Compression energy may be suppressed by velocity filtering which does not require a priori knowledge of shear to compression energy ratio or by steering a null at the compression wave component of the signal detected by the sensor array which does require such a priori knowledge.

(a) Velocity Filtering

Velocity filtering exploits the differences in apparent wave speeds between the compression waves and other waves including shear waves moving more slowly across the array sensors. Velocity filtering does so by filtering the signals so that waves of very high apparent wave speeds are eliminated by the filter and slower moving waves are allowed to pass through.

(i) Linear Arrays—Uniform Sensor Spacing

One velocity filter algorithm applicable to data from a linear array of equally spaced sensors is summarized below:

1. Compute the two-dimensional discrete Fourier transform of the sensor data, F(u,v) defined in Equation 26, infra. This is a two-dimensional function of temporal frequency and spatial frequency or wavenumber.
2. Window the data in the f-k plane (frequency-wavenumber) by computing W(u,v)F(u,v) where the window function W(u,v) is designed to eliminate features with unwanted velocities and pass others.
3. Compute the inverse two-dimensional Fourier transform to get the velocity filtered time series. See Equation 28, infra. Alternately, if the data are to be processed in the frequency domain, then compute the one-dimensional inverse Fourier transform in the spatial frequency dimension.

The algorithm derives from the fact that with a linear array, the acoustic field is sampled in both time and space. The resulting sensor data are treated as a two-dimensional discrete function (f(n,m)) where n and m are the discrete variables for time and distance from the source. A straightforward implementation of a velocity filter for linear arrays starts with the two-variable discrete Fourier transform of the sensor data:

$$F(u, v) = \sum_{n=0}^{N-1}\sum_{m=0}^{M-1} f(n, m)e^{-i2\pi(un/N + vm/M)}$$

Equation 26

The forward transform has a unique inverse that is given by:

$$f(n, m) = \frac{1}{MN}\sum_{u=0}^{N-1}\sum_{v=0}^{M-1} F(u, v)e^{-i2\pi(un/N + vm/M)}$$

Equation 27

This makes it possible to compute F(u,v), manipulate the data in the transform domain and then compute the inverse transform to get back a filtered version of f(n,m). The forward transform can be obtained by two successive one-dimensional Fourier transforms. First compute the Fourier transform of f(n,m) in the time domain separately for every channel. This yields a complex intermediate function F(u, m). The sensor measurements are real (not complex), and F(u,m) has conjugate symmetry about f=0 in the temporal frequency dimension. Then compute the Fourier transform of F(u,m) in the spatial dimension across all channels for every frequency bin. The final function, F(u,v) does not necessarily have conjugate symmetry about k=0 in the spatial frequency dimension.

Figure 16:
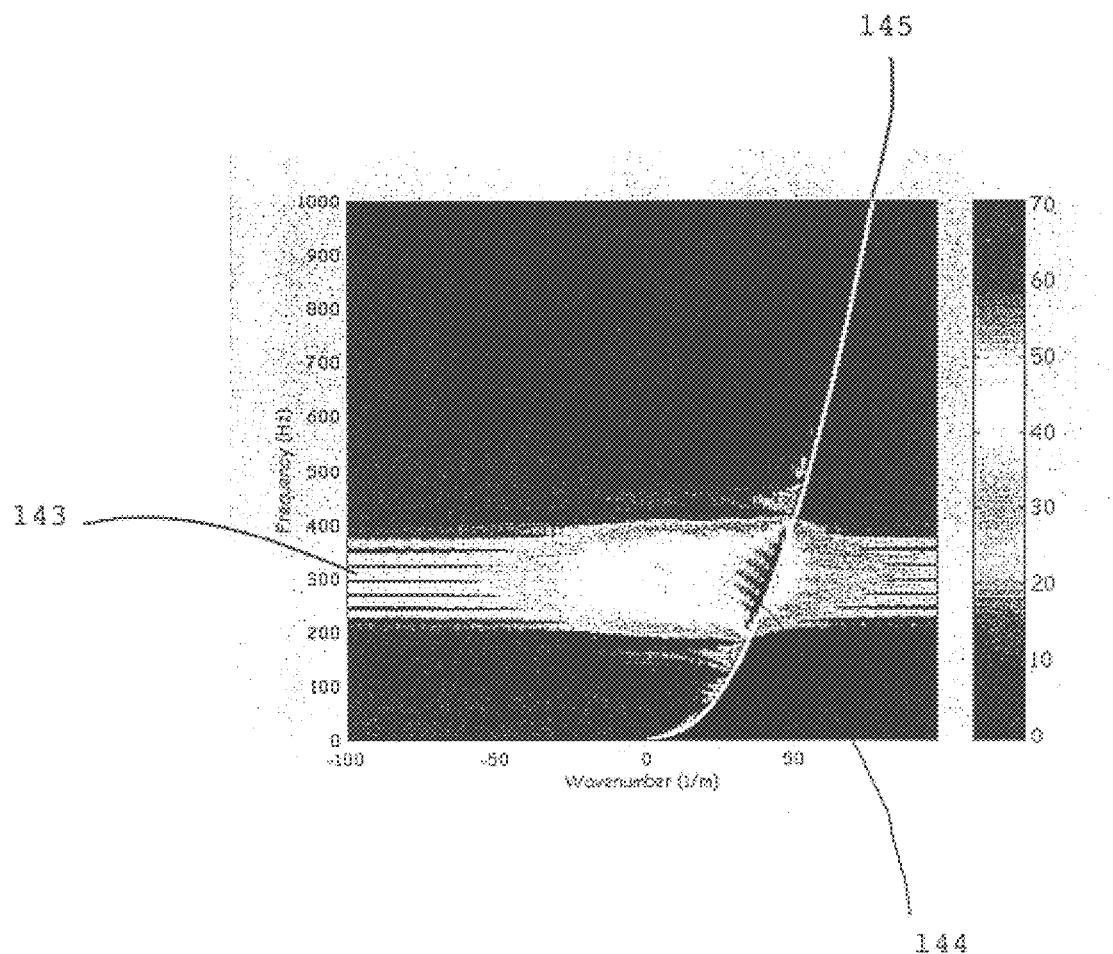
FIG. 16 illustrates a frequency number decomposition with only shear waves present in the form of a 2-D transform F(f,k)
Figure 17:
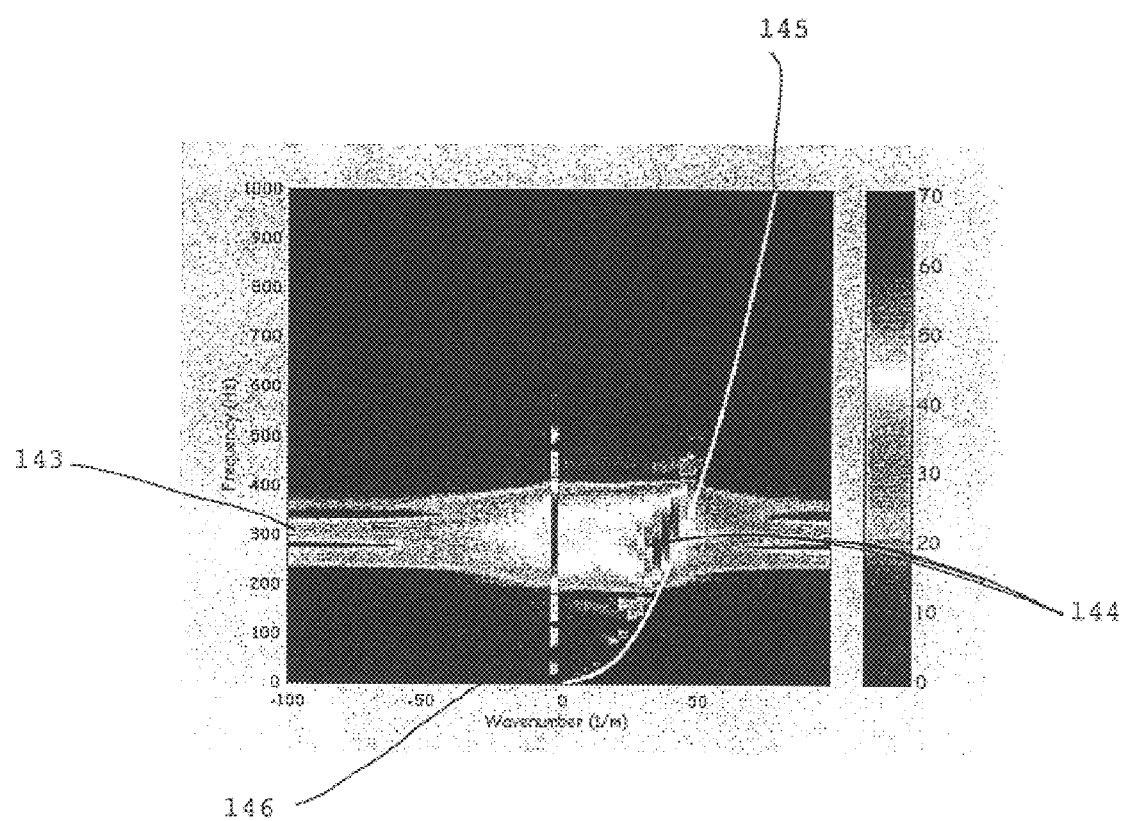
FIG. 17 illustrates a frequency number decomposition with compressional and shear waves present in the form of a 2-D transform F(f,k).

The FIGS. 16 and 17 magnitude plots of the function $10\log_{10}(|F(u,v)|^2)$ show another important property of the transformed data. The dispersion relations that govern the propagation of compressional and shear waves appear as different features of the f-k plane. More specifically, FIG. 16 illustrates frequency-wave number decomposition with only shear waves present. FIG. 17 illustrates frequency-wave number decomposition with compressional and shear waves. A band of energy 143 received at an array is shown. The function f(n,m) used to generate the FIG. 16 image is synthesized by propagating an artificial source to the elements of a linear array. The artificial source contains only a shear component. Shear wave dispersion is illustrated at 144.

The FIG. 16 f(n,m) function used to generate the FIG. 17 image is synthesized using an artificial source with shear and compressional waves. Superimposed on both images (FIGS. 16 and 17) is the dispersion curve 145 for shear waves predicted by Verburg, J.: *Transmission of Vibrations of the Heat to the Chest Wall*. Advanced Cardiovascular Physics, (1983) 5(Part III):84–103.

As FIGS. 16 and 17 show, the different waves produce distinct linear features in the f-k plane. The slope of a line in the f-k plane has dimensions of velocity. The steeper the slope, the higher the wave speed. Curved lines correspond to dispersive waves since the velocity changes with frequency. Note that the shear wave speed increases with frequency as predicted by Verburg's curve. The compressional wave dispersion feature is illustrated at 146 (FIG. 17). This feature is vertical, corresponding to a nearly infinite apparent wave speed across the array. This is the energy to be filtered out.

To implement the velocity filtering, apply a two-dimensional window, W(u,v) to F(u,v), designed to remove the vertical feature near k=0 and then compute the inverse transform as follows:

$$\tilde{f}(n, m) = \frac{1}{MN}\sum_{u=0}^{N-1}\sum_{v=0}^{M-1} W(u, v) \cdot F(u, v)e^{i2\pi(un/N + vm/M)}$$

Equation 28

An example window function is a two-dimensional boxcar that is zero for P wavenumber bins on either side of k=0 and all frequency bins, and one for all other values of f and k.

$$W(u, v) = \begin{cases} 0 & \text{for } v \in \left[\frac{M-1}{2} - P, \frac{M-1}{2} + P\right], \forall u \\ 1 & \text{otherwise} \end{cases}$$

Equation 29

Figure 18:
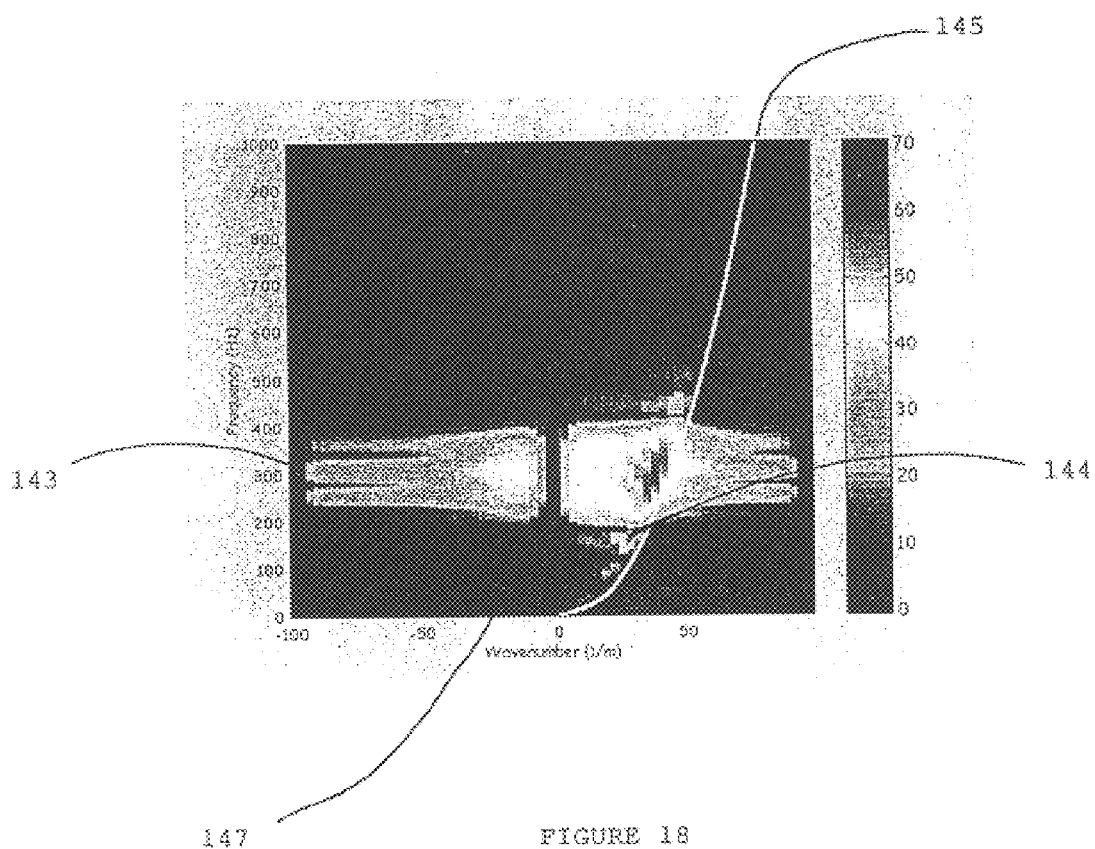
FIG. 18 illustrates a windowed 2-D transform W(f,k) F(f,k) frequency number decomposition for shear and compressional waves.

FIG. 18 illustrates frequency-wave number decomposition with window applied as an example of the product W(u,v)F(u,v) for shear and compressional waves. Here the window function has a 12% cosine taper that provides a more gentle roll-off near k=0. The vertical feature 147 near k=0 from the compressional wave has been eliminated by the window function.

Figure 19:
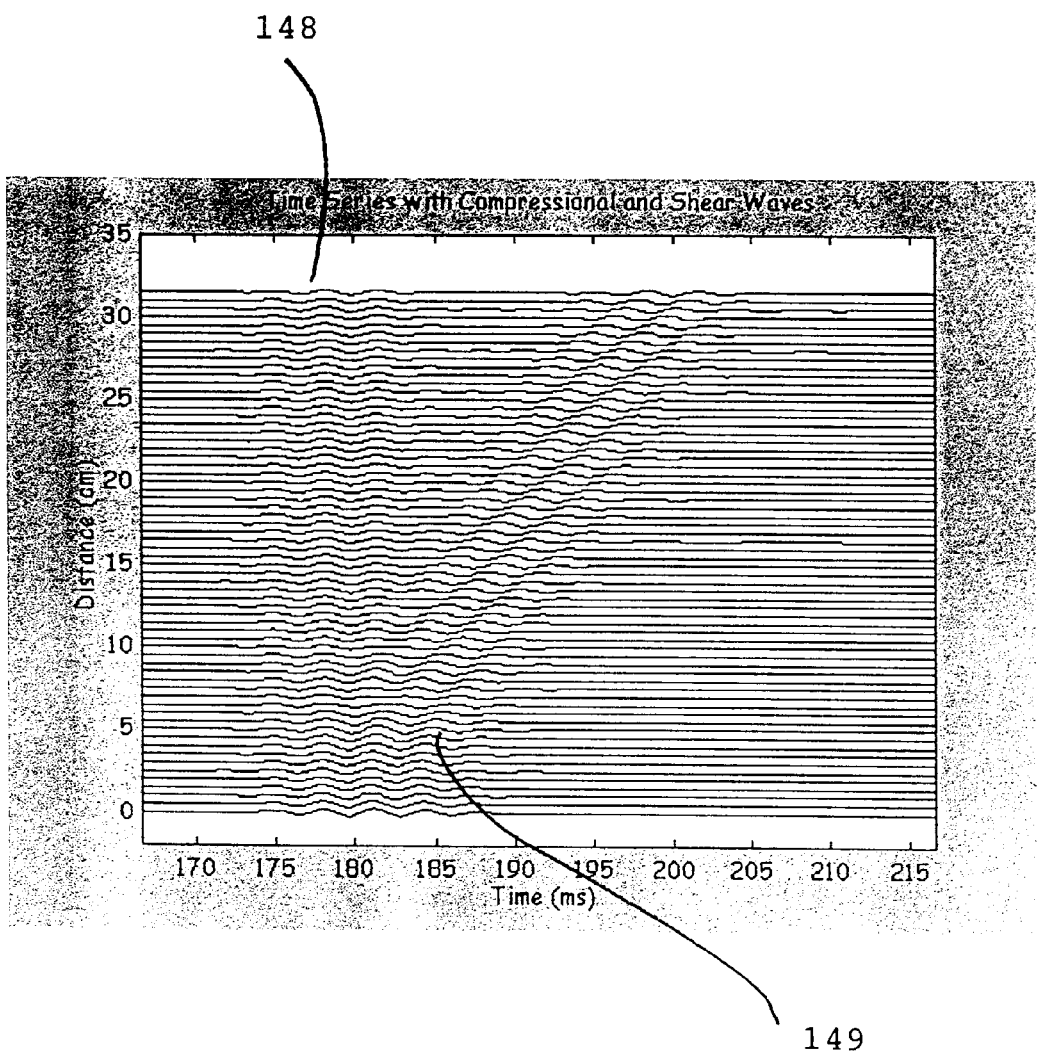
FIG. 19 is a stacked plot that depicts synthetic waveforms at a linear array with compressional and shear wave arrivals.
Figure 20:
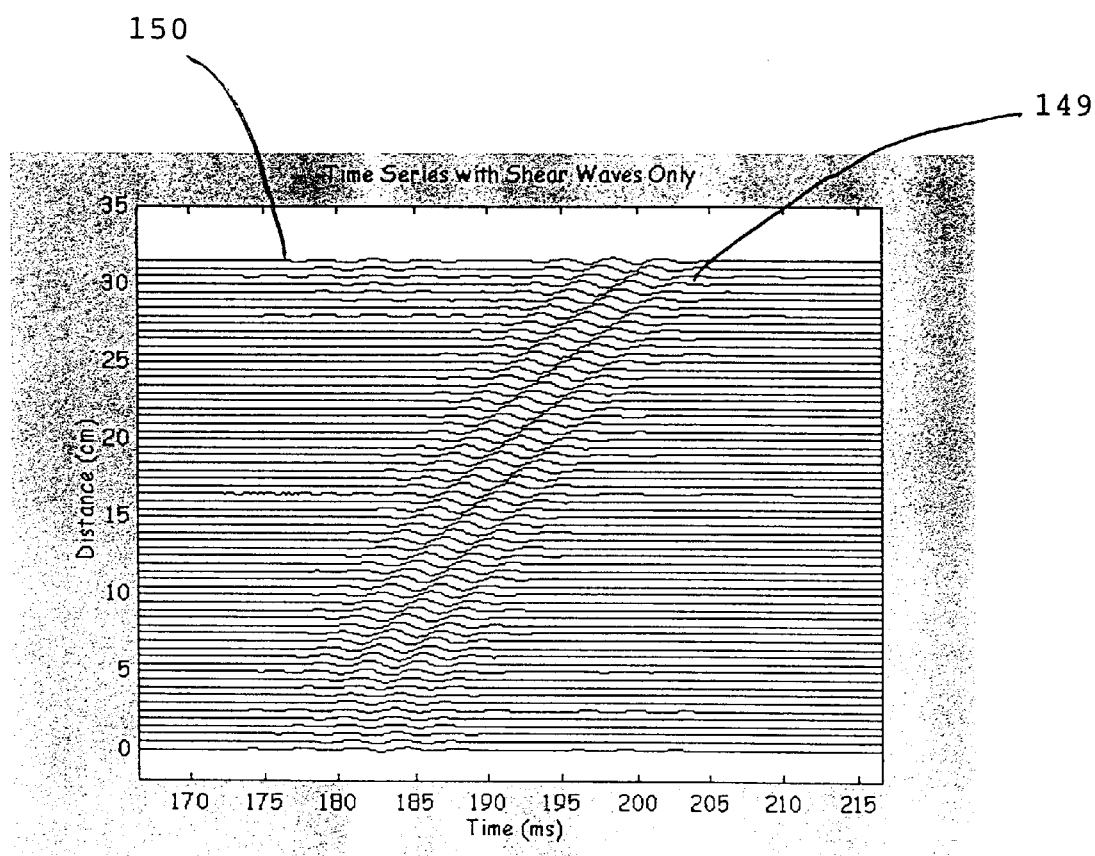
FIG. 20 is a stacked plot that depicts synthetic waveforms at a linear array with compressional and shear wave arrivals after velocity filtering. Comparison with FIG. 19 demonstrates the absence of compressional waves in FIG. 20.

FIGS. 19 and 20 are stack plots of the signals recorded at each sensor position as a function of time and distance along the array and therefore show the effect on the time series of the velocity filtering. In FIG. 19 the compressional arrivals 148 and shear arrivals 149 can be seen clearly. The compressional wave arrives at each sensor on the linear array at virtually the same time. The shear waves are slower and dispersive. FIG. 20 is a stack plot of the signals after velocity filtering. The elimination by velocity filtering of the compressional waves from the time series is shown at 150. FIG. 20 shows that the shear wave arrivals at 151 are not affected by elimination of velocity filter.

(ii) Non-linear Arrays

The discrete Fourier transform requires uniformly spaced samples. Because the sensor data f(n,m), from the array are not uniformly sampled in the spatial dimension, the data are spatially interpolated onto a regularly spaced axis. To accomplish this, advantage is taken of the fact that the two-dimensional discrete Fourier transform may be computed by two one-dimensional transforms. An algorithm for velocity filtering data from other than linear arrays with uniformly spaced sensors follows.

1. Compute the distances from a potential source location (i.e. a point in the volume for beamforming) to each of the array sensors. Sort the receivers in ascending order according to their distance from the potential source. This leads to the two-dimensional function f(n,m) where m are irregularly spaced, increasing distances.

2. Compute the Fourier transform of the sensor data, f(n,m) along the time dimension. This yields the complex function F(u,m), with irregularly spaced samples in m.

3. At each frequency bin, perform a complex interpolation of F(u,m) onto a regularly spaced coordinate axis, $m_i$. This yields the function $F(u,m_i)$ which has uniformly spaced samples in the spatial dimension.

4. Compute the Fourier transform of $F(u,m_i)$ along the spatial dimension. This results in the two-dimensional function F(u,v) where v is a discrete radial wavenumber variable.

5. Window the data in the f-k plane by computing the product W(u,v) F(u,v) where the window function is designed to eliminate features with unwanted wave speeds and pass others.

6. Compute the inverse two-dimensional Fourier transform to get the velocity filtered time series, $f(n,m_i)$. Resample $f(n,m_i)$ at the original sensor distances, to get back the filtered version of f(n,m).

(b) Steering a Null at the Compression Wave

A beamformer null exists when the response at a specific location or angle goes to zero. See FIG. 21 which illustrates four labeled nulls in a conventional beamformer beam steering angle under the conditions identified in FIG. 15. The sensors are in a linear array. Four nulls appear in the response of the beamformer. There are potentially nine null locations. The five null locations not shown are outside the space spanned by the steering vectors for plane waves. The four nulls that appear in this response are not controlled in their locations but appear spontaneously.

The invention may include a "null steering" operation to place a null at the location or angle where an interfering signal originates.

Figure 21:
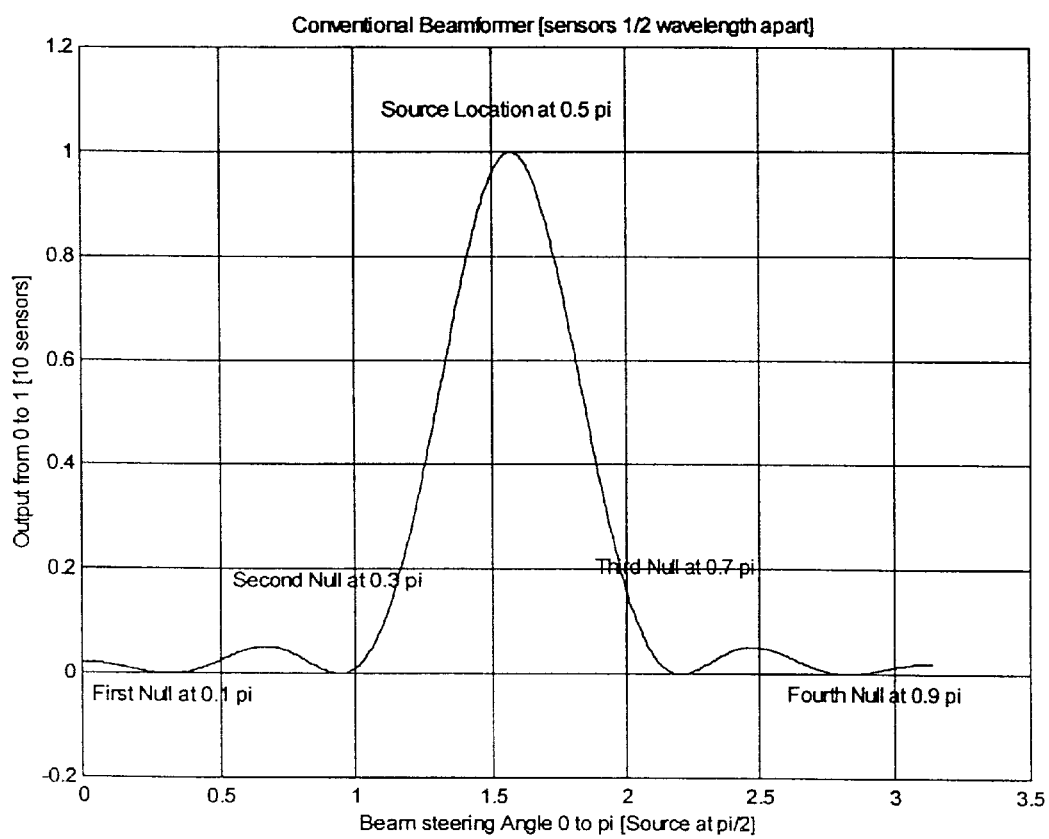
FIG. 21 is a plot of the beam steering angle 0 to n of a conventional beamformer, no null steer as a function of output from 0 to 1 from a linear array of ten sensors one-half wavelength apart. Source at $\pi/2$. First, second, third and fourth nulls at 0.1, 0.3, 0.7 and $0.9\pi$ are shown.
Figure 22:
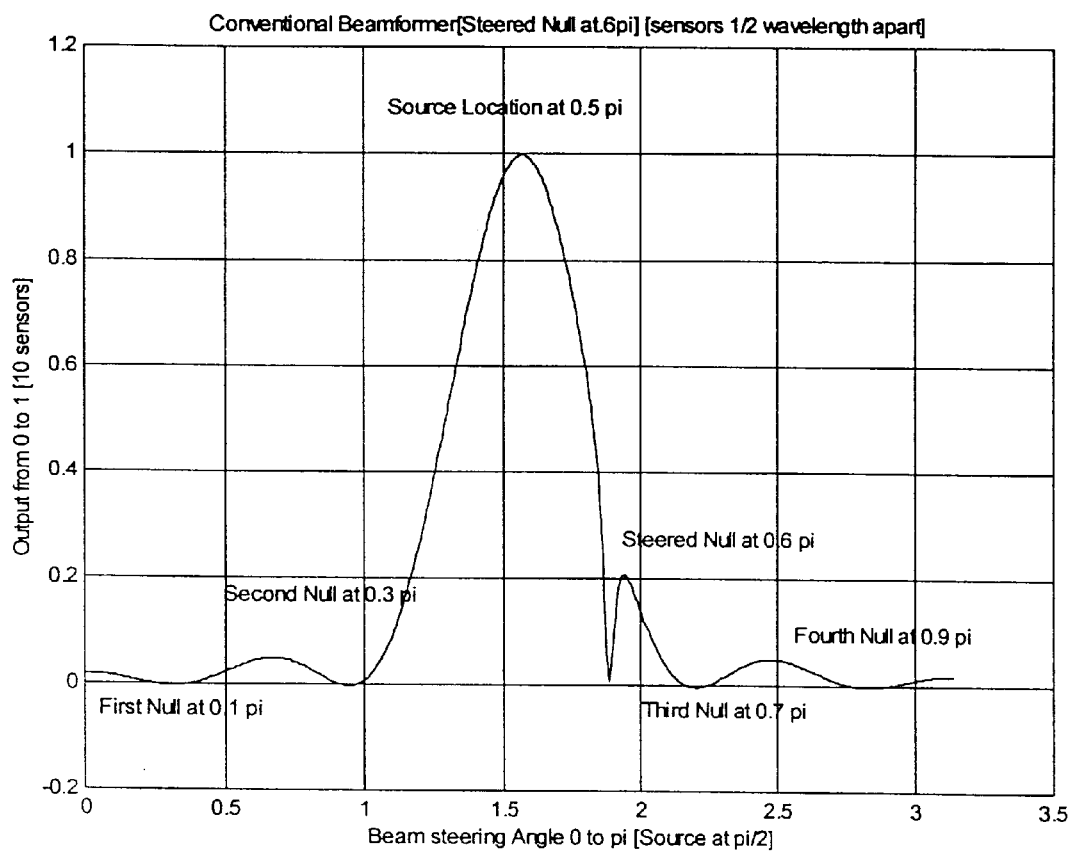
FIG. 22 is similar to FIG. 21 except that a steered null at $0.6\pi$ is shown preceding the third null at $0.7\pi$.

FIG. 22 illustrates a steered null of 0.6 π under the same conditions as described and illustrated by FIG. 21.

Figure 23:
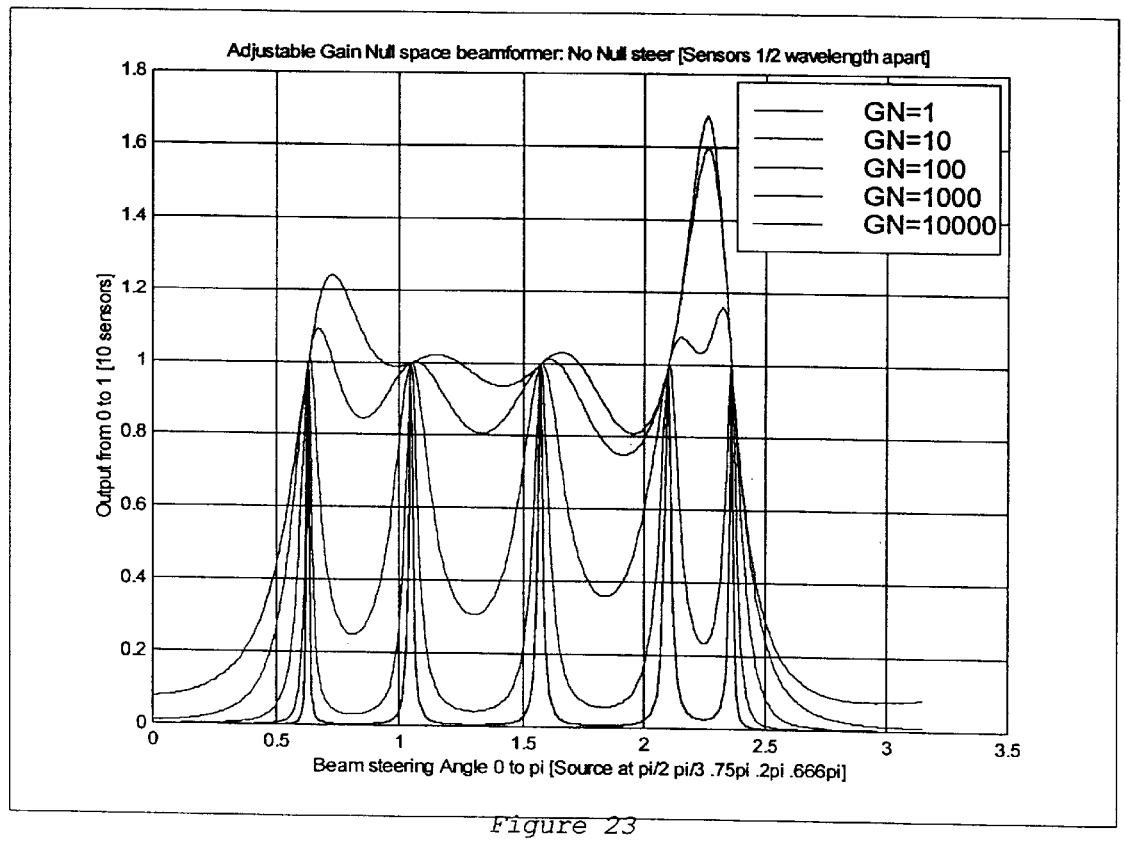
FIG. 23 is a plot of the beam steering angle 0 to $\pi$ of an adjustable gain null space beamformer, no null steer, as a function of output from 0 to 1 from ten sensors spaced one-half wavelength apart at five gain levels. Source at $\pi/2$, $\pi/3$, $0.75\pi$ and $0.666\ \pi$.

FIG. 23 is a plot of the beam steering angle, 0 to π of an adjustable null space beamformer at five gain values as set forth.

Two options are available for steering a null at the compression wave component of the signal detected by the sensor array. The two options require a priori knowledge of the shear to compression energy ratio.

Figure 24:
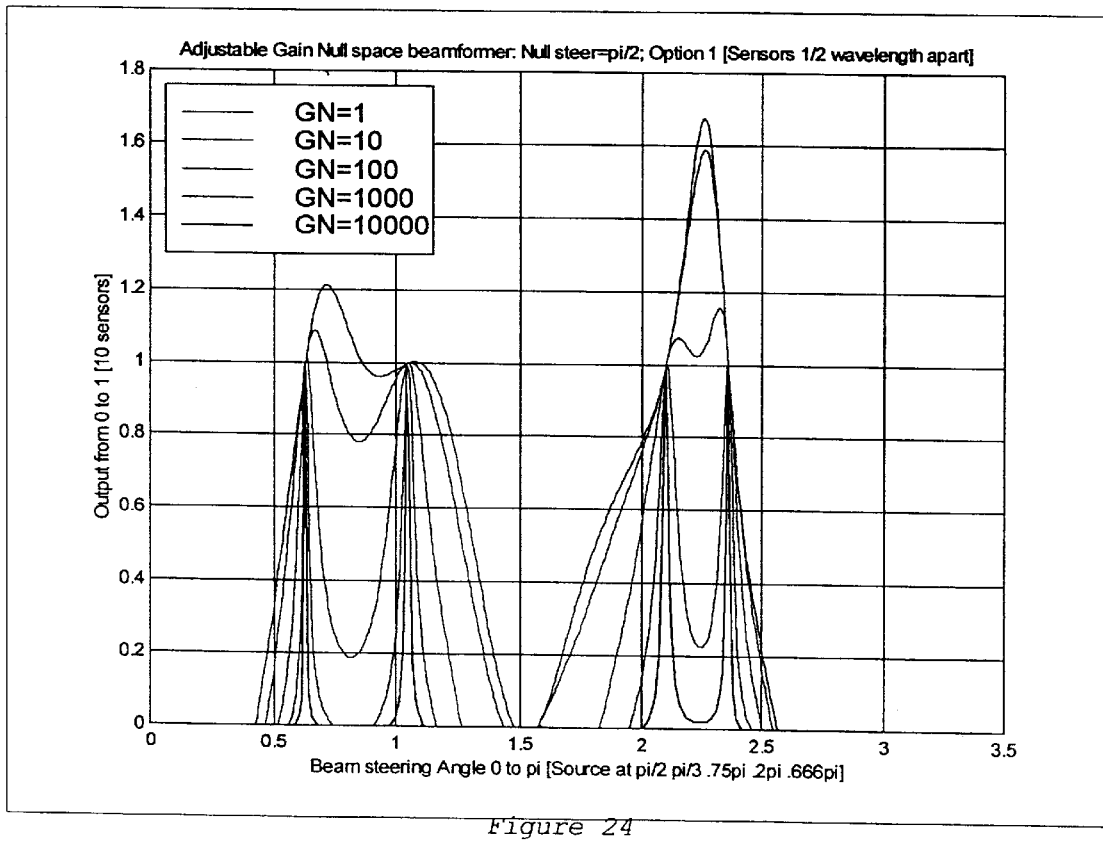
FIG. 24 is similar to FIG. 23 except that a null steer at $\pi/2$ is shown. This figure illustrates "Option 1" discussed at page 74 of this specification.

(i) Option 1—See FIG. 24:

First proceed as in Adjustable Gain Null/Resolution Space Beamformer as described. Then generate a second matrix of steering vectors that represents the phase shifts associated with compression waves from potential source locations. At the frequencies of interest, let $S_{SH}$=Steering vector for shear waves, $S_{COM}$=Steering vector for compression waves, and $P_{SH}P_{COM}$=The ratio of shear to compression power at the source location.

The following variables have the same meaning as before: GN, $R_S$, $R_N$ and $B_{output\ in\ power}$.

Then the beamformer output can be expressed by the relationship below. Only positive values of the output are valid. The beam width is adjustable while the null width is not controlled.

$$B_{Output\ in\ power} = \frac{1}{S_{SH}^H R_S S_{SH} + GN \cdot S_{SH}^H R_N S_{SH}} -$$

$$P_{SH} \frac{P_{COM}[S_{SH}^H R_S S_{COM} \cdot S_{COM}^H R_S S_{SH}]}{[S_{COM}^H R_S S_{COM} + GN \cdot S_{COM}^H R_N S_{COM}]} -$$

$$P_{SH} P_{COM} \frac{GN \cdot [[S_{SH}^H R_N S_{COM} \cdot S_{COM}^H R_S S_{SH}] + [S_{SH}^H R_S S_{COM} \cdot S_{COM}^H R_N S_{SH}]]}{[S_{COM}^H R_S S_{COM} + GN \cdot S_{COM}^H R_N S_{COM}]} -$$

$$P_{SH} P_{COM} GN^2 \cdot \frac{[S_{SH}^H R_N S_{COM} \cdot S_{COM}^H R_N S_{SH}]}{[S_{COM}^H R_S S_{COM} + GN \cdot S_{COM}^H R_N S_{COM}]}$$

Equation 30

The first term of the relationship is the previously described beamformer that has only positive values. The second term has value of zero when the first term approaches 1 and a value of −1 when compressive steering vector is pointing at a compressive source.

Figure 25:
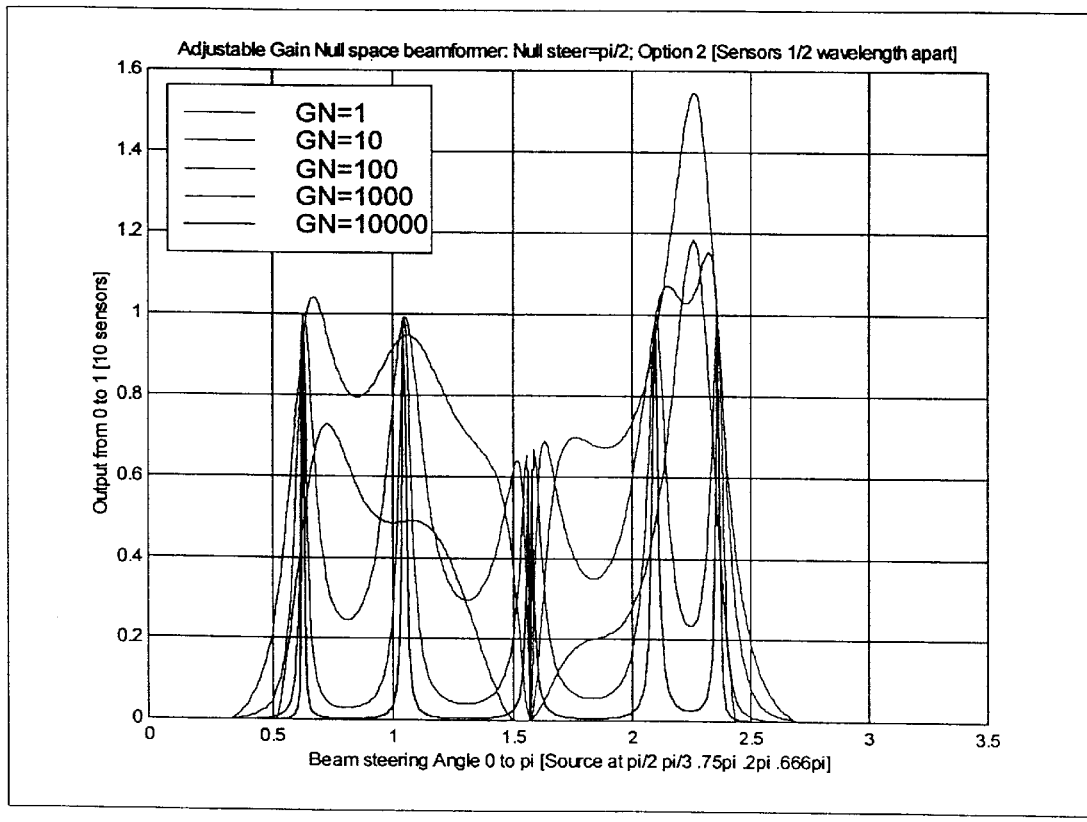
FIG. 25 is similar to FIG. 24, except that it illustrates "Option 2" discussed at page 76 of this specification.

(ii) Option 2—See FIG. 25

The beamformer, described in option 1 is modified by a different second term that produces a null in the response. This different second term does not use the R matrix regardless of how it is generated. Instead, a new second matrix is formed:

$$R_{COM} = S^H_{COM} S_{COM}$$

where:

$S_{COM}$=Steering vector for compression waves, and $R_{COM}$=Correlation matrix for compressive waves.

Equation 31

The inverse of this matrix can be expressed in two parts as before by performing an eigenvalue decomposition of the matrix.

$$R^{-1}_{COM} = R_{CS} + R_{CN}$$

where:

$R_{CS}$=The inverse rank space of $R_{COM}$ which has only one eigenvalue, and $R_{CN}$=The inverse null space of $R_{COM}$.

Equation 32

The beamformer output is now the positive part of the following relationship:

$$B_{Output\ in\ power} = \frac{1}{S_{SH}^H R_S S_{SH} + GN_{SH} \cdot S_{SH}^H R_N S_{SH}} - P_{SH} P_{COM} \frac{1}{S_{COM}^H R_{CS} S_{COM} + GN_{COM} \cdot S_{COM}^H R_{CN} S_{COM}}$$

where:

$GN_{SH}$=Gain Null Space Shear Waves $GN_{COM}$=Gain Null Space Compression Waves Equation 33

Since the $R_{COM}$ matrix has only one non-zero eigenvalue, and all the other eigenvectors are orthogonal to this eigenvector, the eigenvector associated with the non-zero eigenvalue is a scaled version of the original $S_{COM}$ vector. The problem of finding a set of vectors orthogonal to the first vector $S_{COM}$, can be done by the Modified Gram-Schmidt algorithm [Matrix Computations, Goloub and Van Loan Sec. 6.2] which is faster than finding the eigenvalues and eigenvectors of a matrix. This leads to a new version of option 2.

The Modified Gram-Schmidt algorithm is listed in Appendix A. The output of this algorithm is a new matrix and from this and the two parts of the inverse of R, the beamformer output can be found by the second algorithm described in Appendix B.

(c) Beamforming Methods When Wave Speed (c) as a Function of Frequency is Unknown Three useful methods are:

(i) Optimal gridding of space for the rapid determination of the source location in (x y z c) beamforming hyper volume;

(ii) Determination of a source location as a non-linear unconstrained optimization problem; and (iii) Display of source location on a uniformly gridded space (x y z) that has uniform resolution at each point in the space.

(i) Optimal Gridding

Figure 26A:
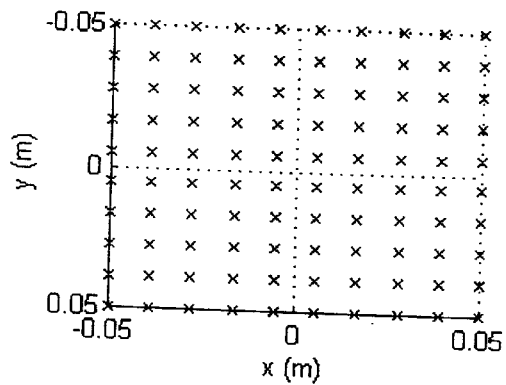
FIG. 26A is an x-y background projection of a regularly spaced 3D grid.
Figure 26B:
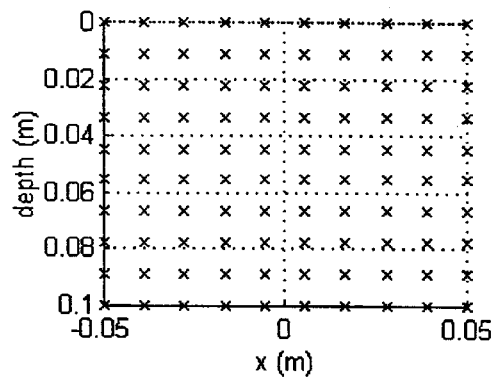
FIG. 26B is an x-z depth projection of a regularly spaced 3D grid.
Figure 26C:
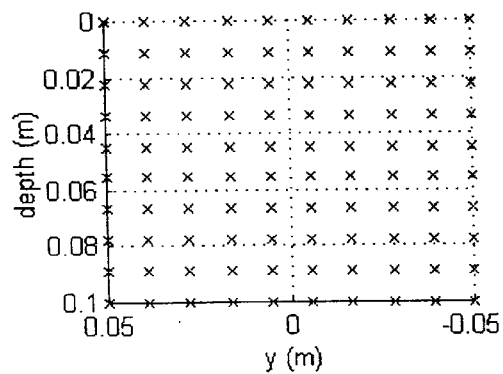
FIG. 26C is a y-z depth projection of a regularly spaced 3D grid.
Figure 27:
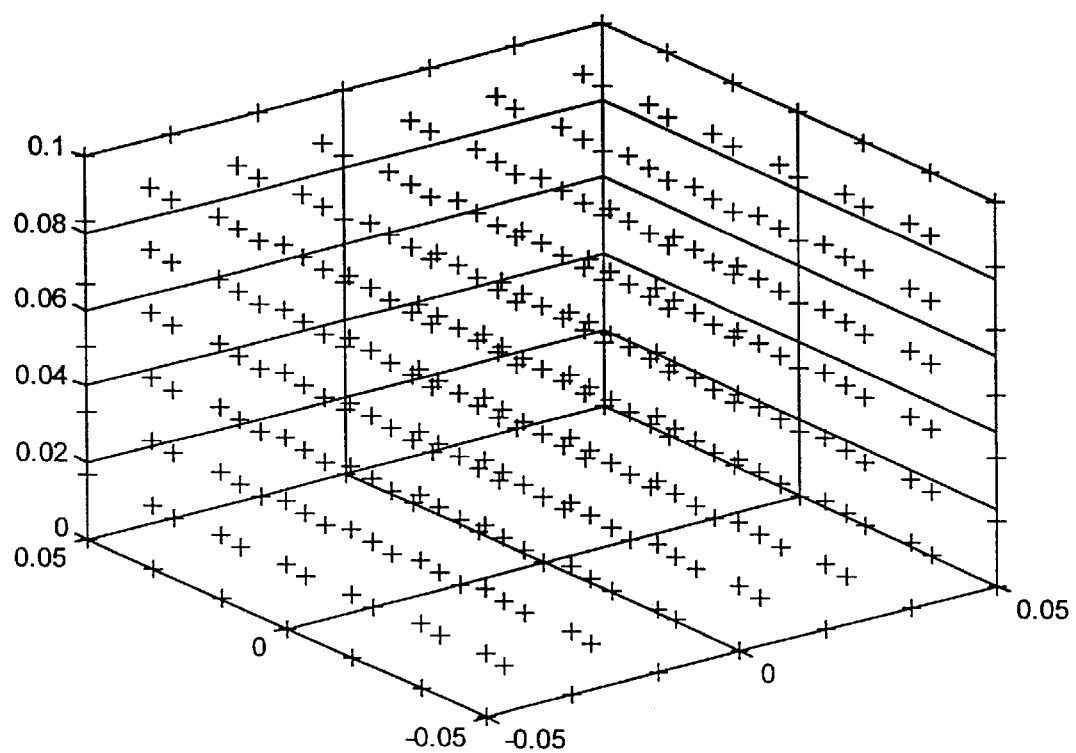
FIG. 27 displays the 3D grid points in three dimensions.

FIGS. 26A, 26B and 26C are the projections of the 3D grid. FIG. 27 displays the grid points in three dimensions.

Figure 28A:
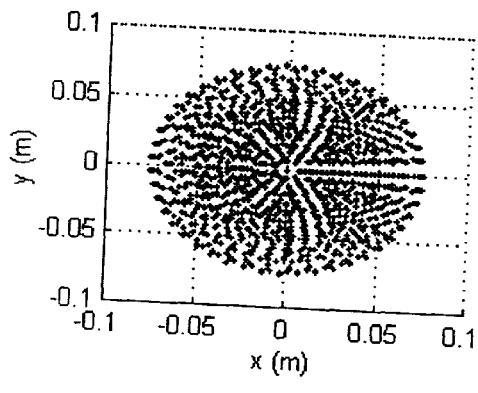
FIG. 28A is an x-y projection of a 4D optimally spaced grid.
Figure 28B:
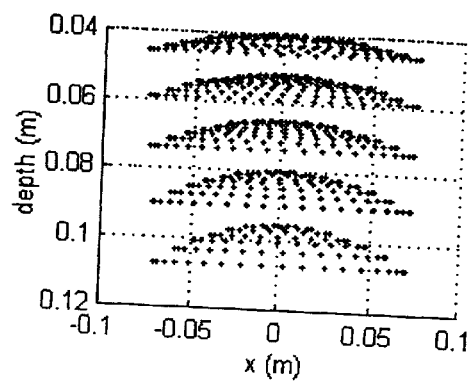
FIG. 28B is an x-z depth projection of a 4D optimally spaced grid.
Figure 28C:
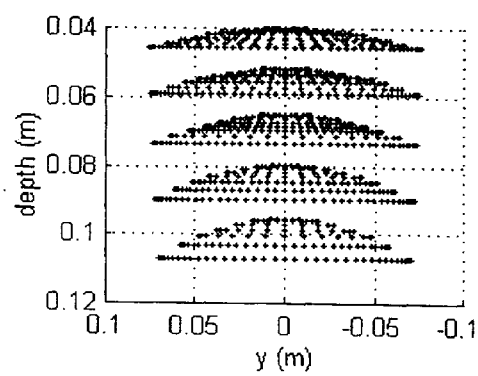
FIG. 28C is a y-z depth projection of a 4D optimally spaced grid.
Figure 29:
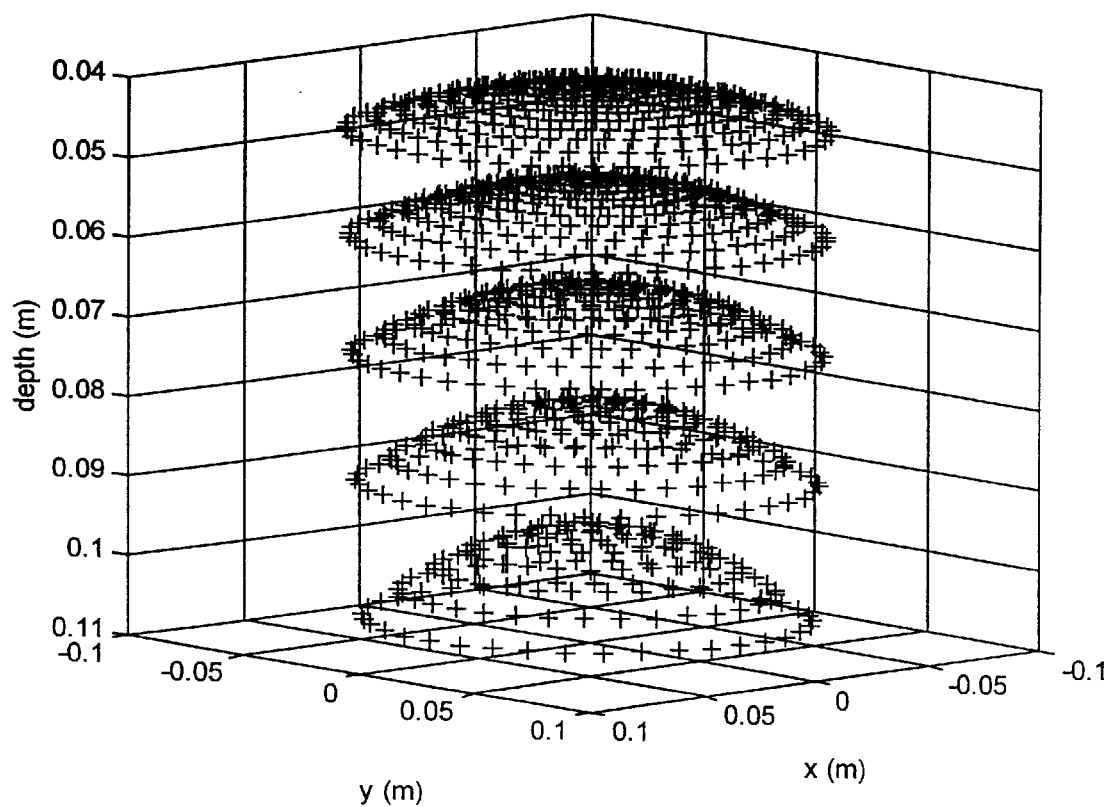
FIG. 29 is a 3D projection of the 4D grid onto three dimensions.

FIG. 28 and FIG. 29 are examples of the 4D optimal grid which maintains constant beamwidth resolution throughout the volume with a minimum number of points and therefore a minimum amount of computational effort. FIGS. 28A, B and C are the set of orthogonal projections and FIG. 29 is the 3D projection of the four dimensional grid onto three dimensions.

Beamforming can be thought of as a search through data space to find the (x, y, z) coordinates that give the maximum output at each frequency. If the velocity of propagation is unknown, it becomes the fourth unknown "c" in the search. To do this search efficiently, an optimal grid having the minimum number of points that need be tested (beamform to) in the volume should be used.

An algorithm useful to generate an optimal grid may include:

(1) Assuming a shear wave speed as a function of frequency.

(2) Generating half-power beam width estimates for each of a high, a low, and a middle frequency.

(3) Generating a synthetic array of sensors.

(4) Generating a three-dimensional grid of potential turbulent flow noise source locations beneath the synthetic sensor array.

(5) Identifying at each potential noise source location on the grid, a synthetic source and propagating waves to the surface from that source.

(6) Determining the beam widths in both plus and minus directions from each synthetic source location by changing the assumed value of x y z and c in sequence for each source location from the correct values until the beam output is one half the correct value, wherein four beam widths are associated with each point in four spaces.

(7) From the information provided by item (5), generating a function that gives beam width in one dimension as a function of the other dimensions.

(8) Constructing a 4-D (x y z c) grid from the information provided by item (6) by:

(a) Generating surfaces of equal Z resolution (beam width).

(b) On these surfaces, generating rings of equal R resolution (beam width).

(c) On these rings, finding points of equal angular resolution (beam width).

(d) On these points in 3 space (cylindrical coordinates), find points in c space that have equal resolution in velocity.

This 4-D grid is the optimum solution for finding a potential source of unknown location where the potential locations of the source are uniformly dispersed throughout the volume. The use of this grid minimizes the computational effort required to find a source and its associated position in 4 space. A true source location will generate maximal output in the beamformer for the correct values of [x y z c]. To speed the search process, a conventional beamformer algorithm as described may be used initially to search the four dimensional space for a source.

(ii) Non-Linear Unconstrained Optimization Problem

To find a source given an estimate of its location in (x y z c), Newton's method can be used. The needed partial derivatives can be estimated with finite differences. The object is to find a point where the gradient is zero and the Hessian matrix of partial derivatives has all negative eigenvalues indicating the location is on a peak.

The gradient of B=Beamformer output in power with respect to the variables x,y,z, and c.

$$\text{Gradient} = \nabla = \begin{vmatrix} \frac{\partial B}{\partial X} \\ \frac{\partial B}{\partial Y} \\ \frac{\partial B}{\partial Z} \\ \frac{\partial B}{\partial C} \end{vmatrix}$$

where:

B=Beamformer output in power,

X=Potential x location of source,
Y=Potentialy y location of source,
Z=Potential z location of source,
C=Shear velocity of media.

Equation 34

The Hessian of B with respect to the variables x, y, z and c is shown below.

$$\text{Hessian} = H = \begin{vmatrix} \frac{\partial^2 B}{\partial X^2} & \frac{\partial^2 B}{\partial X \partial Y} & \frac{\partial^2 B}{\partial X \partial Z} & \frac{\partial^2 B}{\partial X \partial C} \\ \frac{\partial^2 B}{\partial Y \partial X} & \frac{\partial^2 B}{\partial Y^2} & \frac{\partial^2 B}{\partial Y \partial Z} & \frac{\partial^2 B}{\partial X \partial C} \\ \frac{\partial^2 B}{\partial Z \partial X} & \frac{\partial^2 B}{\partial Z \partial Y} & \frac{\partial^2 B}{\partial Z^2} & \frac{\partial^2 B}{\partial Z \partial C} \\ \frac{\partial^2 B}{\partial C \partial X} & \frac{\partial^2 B}{\partial C \partial Y} & \frac{\partial^2 B}{\partial C \partial Z} & \frac{\partial^2 B}{\partial C^2} \end{vmatrix}$$

Equation 35

The update for each new estimate on x, y, z, and c becomes:

$$\begin{vmatrix} X \\ Y \\ Z \\ C \end{vmatrix}_{NEW} = \begin{vmatrix} X \\ Y \\ Z \\ C \end{vmatrix}_{OLD} - H_{OLD}^{-1} \cdot \nabla_{OLD}$$

Equation 36

Force the eigenvalues of the Hessian to be negative at all iterations lest the method converge to a saddle point or a minimum point. Display the results on a uniformly gridded space.

(iii) Display of Source Location

3-D visualization methods are usually designed to work on uniformly gridded data. With the adjustable gain null space beamformer as described, each point and frequency can have nearly the same resolution by changing GN to give the same beam widths at different locations within the grid.

7. Non-Invasive Detection of Change in Coronary Artery Stenosis

Pursuant to the invention, change in CAD status, specifically, the degree of coronary artery stenosis, may be determined by comparison of acoustic images or measurements made at different times.

Figure 30:
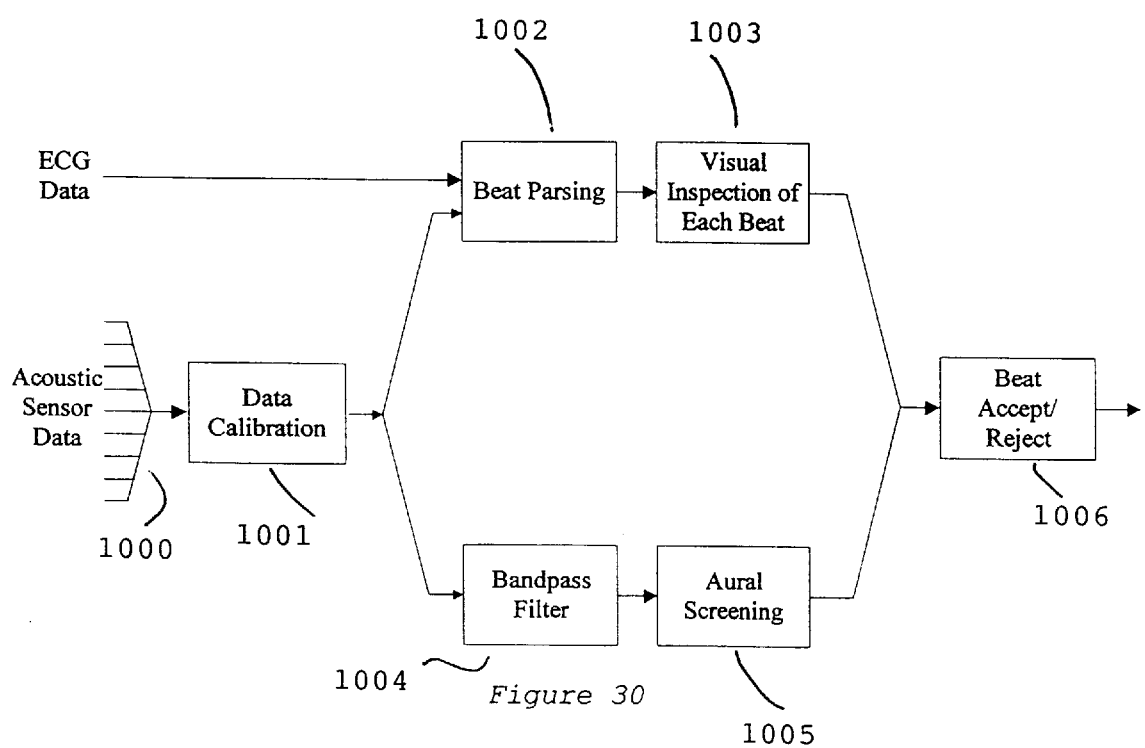
FIG. 30 is the flow diagram or algorithm that illustrates preprocessing of data for use in the detection of change in coronary artery stenosis.
Figure 31:
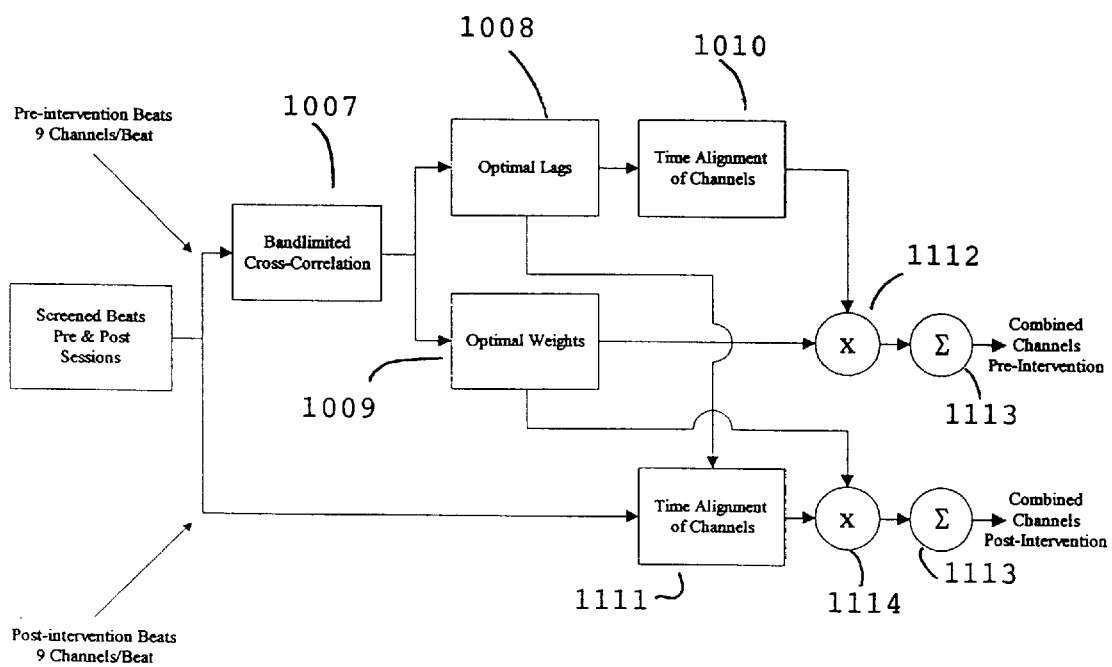
FIG. 31 is a flow diagram that illustrates further processing of the data generated pursuant to FIG. 30.

This aspect of the invention may proceed in three steps in which pre-and post-intervention acoustic data in separate channels from a plurality of sensors, e.g., nine sensors, is preprocessed and quality screened, see FIGS. 30 and 31. The preprocessed channel data undergoes further signal processing to extract and classify pre- and post-intervention energy features, and the extracted and classified features are compared to identify post-intervention change in a stenotic lesion. See FIGS. 31 and 32.

FIG. 30 illustrates a preprocessing phase in which acoustic data is separately generated by an array of acoustic sensors. In the figure, the block 1000 indicates nine channels of data from a nine sensor array as shown by FIG. 6. However, the array may comprise any desired number of sensors. The acoustic sensor data is calibrated at block 1001 and subjected to heart beat parsing concurrently with EGC data at block 1002.

The parsed acoustic sensor data and EGC data is subjected at block 1003 to visual inspection of the signal corresponding to each heart beat to detect abnormalities such as interference from transient noises or breath sounds.

The acoustic sensor data calibrated at block 1001 is also bandpass filtered at block 1004 and subjected to aural screening at block 1005. The visually screened data from block 1003 and the aurally screened data from block 1005 is accepted or rejected on a per beat basis at block 1006 based on the usual inspection and aural screening. The final screening process at block 1006 compares the analysis window for each beat that passed visual inspection at block 1003 with the segments identified by aural inspection at block 1005 as containing interfering noise. If these analysis windows overlap, the analysis window for that beat is rejected from further processing. Typically all channels for a beat will be accepted or rejected together.

If the data passes both the aural screening and the visual inspection, then the data is provided as preliminary processed signals for further evaluation as is seen in FIG. 31.

Referring to FIG. 31, the screened beats produced at block 1006 comprise pre-intervention beats, nine channels per beat and post-intervention beats, nine channels per beat.

The screened, pre-intervention beat data is subjected to band-limited cross-correlation at block 1007. The signal generated at block 1007 is further processed as shown. Specifically, the block 1007 signal is assigned optimal lags at box 1008 and optimal weights at block 1009.

All of the nine pre-intervention signal channels with the optimal lags from box 1008 are time aligned at block 1010 and at block 1111 with the nine channels of post intervention beat data.

The optimally weighted block 1009 pre-intervention beat data is combined at block 1112 (x) with the time aligned data from block 1110 and summed at block 1113.

The data from block 1111 which comprises time aligned optimally lagged pre-intervention data and post-intervention beat data is combined at block 1114 with the optimally weighted block 1009 pre-intervention beat data and summed at block 1115.

Figure 32:
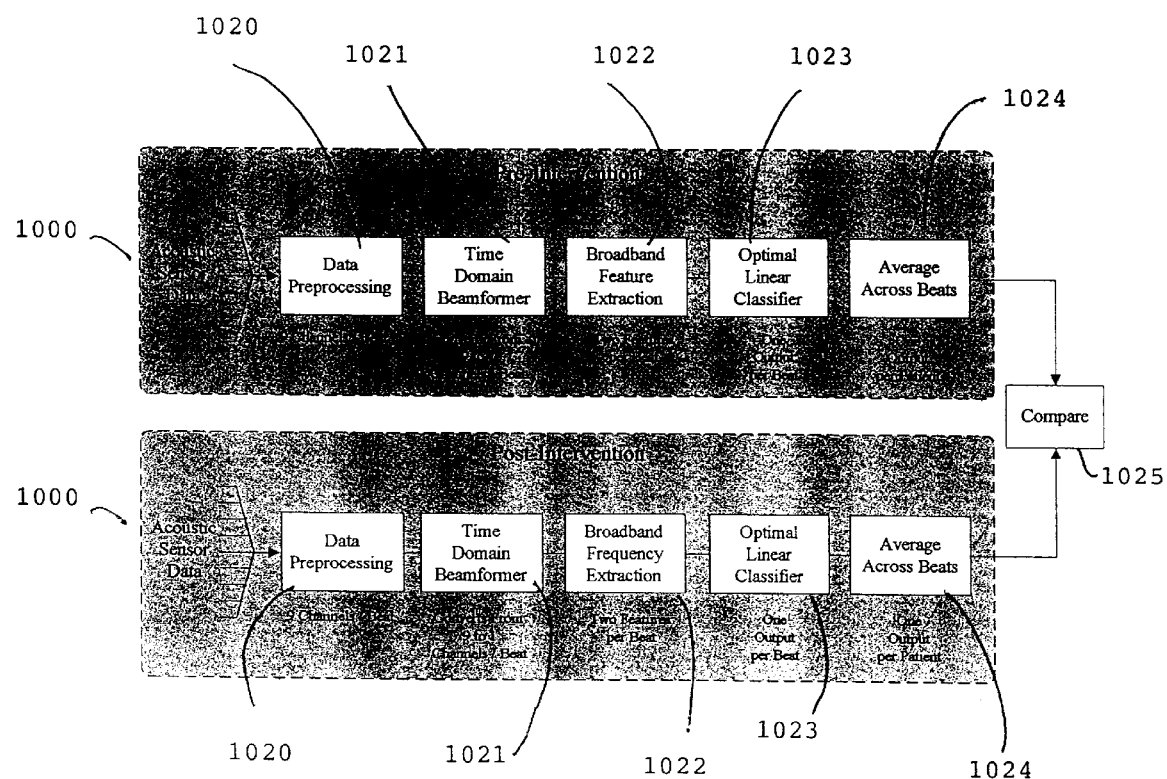
FIG. 32 is a flow diagram that illustrates the steps of combining select frequency band sensor array data from several channels, measured pre- and post-intervention, into a single signal, broadband feature extraction from the single channel data, classification, and comparison of the extracted pre-and post-intervention feature.

FIG. 32 illustrates one method for comparing pre-intervention with post-intervention data features to identify changes in the degree or extent of a coronary artery stentoci lesion.

Referring to FIG. 32, blocks 1000 indicate nine channels of acoustic sensor array data. Blocks 1020 indicate data preprocessing as shown by FIGS. 30 and 31. Block 1021 illustrates use of a time domain beamformer to convert the nine beat channels to one channel.

The single channel per beat output of blocks 1021 is subjected to broadband frequency feature extraction at blocks 1022.

Two energy features are extracted in known manner. One energy feature is extracted at a first low frequency, e.g., 200 to 600 Hz and at a second higher frequency, e.g., 600–1800 Hz.

At blocks 1023 the extracted features are classified per beat into a pre-intervention subclass and a post intervention subclass. Any classifier means may be used. An optimal linear classifier is preferred.

The pre-intervention feature data subclass and the post-intervention feature data subclass are averaged across beats at blocks 1024. The averages are compared at block 1025. Preferably, the comparison is accomplished by plots which separate the number of pre-intervention and post-intervention beats at the high and low frequencies used for feature extraction and by plots of classified pre-and post-intervention beat data. See FIGS. 38 and 39 discussed in Example 6, infra.

A difference between the averaged pre-intervention and post-intervention classifier outputs indicates a stenosis change in a coronary artery of the patient.

Also pursuant to this invention, coronary artery stenosis change may be tracked prior to or post intervention by a comparison of time series of acoustic images produced as described before or after intervention.

Figure 38:
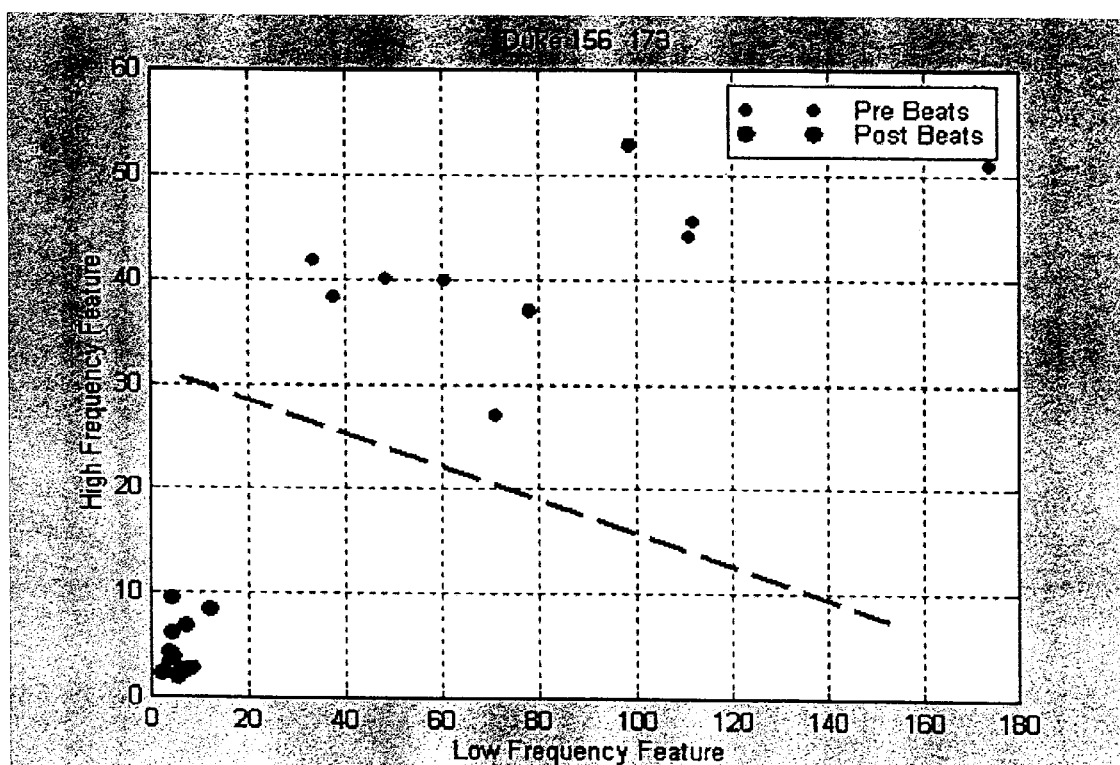
FIG. 38 depicts a comparison of acoustic features indicative of patient heart beats pre and post intervention extracted at high and low frequency bands.
Figure 39:
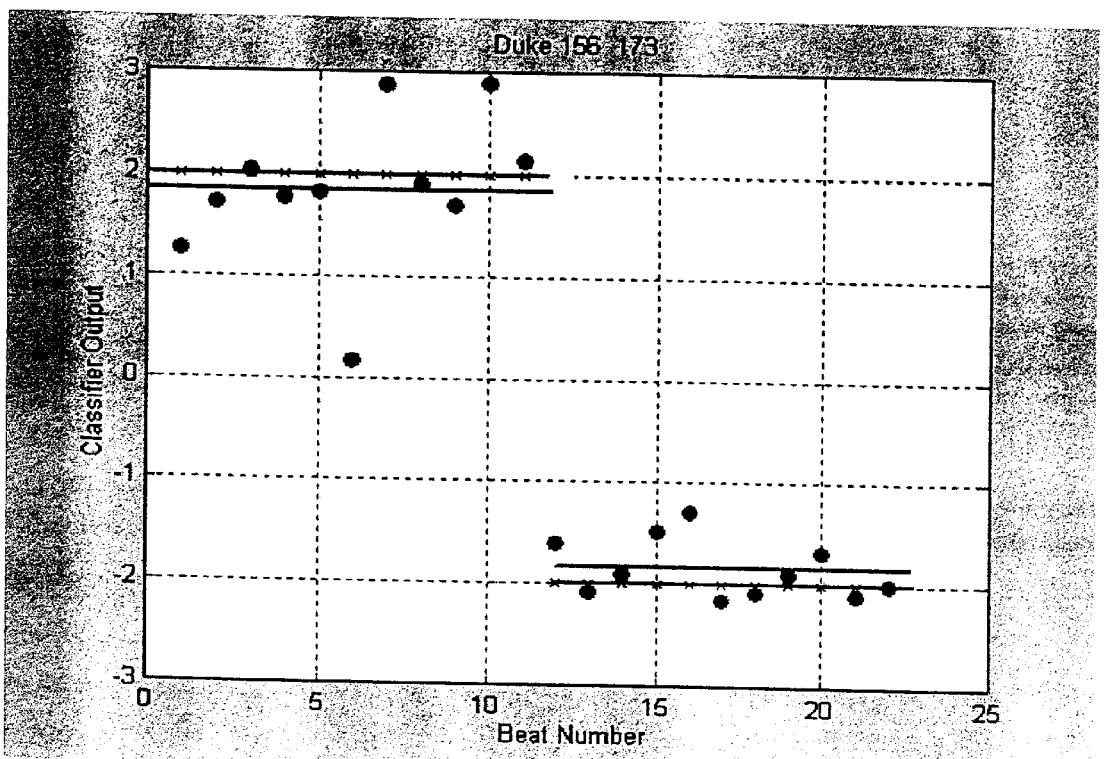
FIG. 39 illustrates the separation and classification of the pre and post intervention beat features extracted at high and low frequency bands as shown in FIG. 38.

The invention also provides standard or a plurality of standard plots typified generally by FIGS. 38 and 39 for use in making diagnostic comparisons of stenotic lesion change with time.

A specific aspect of the invention comprises any plot of the number of beats of a patient's heart at a first time and at a second time against a high frequency feature and a low frequency feature and any plot of a beat classifier output against heart beat numbers before and after percutaneous intervention.

This invention may be used to detect change in coronary artery stenosis after any type of percutaneous revascularization.

Algorithms for data acquisition and preliminary data processing, according to one embodiment of the present invention, shown in FIG. 30 may comprise:
  (i) providing a fixed array of sensors conformable to the chest of a patient;
  (ii) placing said array on the chest of said patient in an area above said patient's heart,
  wherein the patient's heart beat generates $S_1$, $S_2$, $S_3$, $S_4$ and other cardiac sounds;
  (iii) calibrating and converting said sounds into engineering units of acceleration which constitute the signals to be analyzed;
  (iv) segmenting said signals into individual beats of said patient's heart;
  (v) providing for each individual beat of said patient's heart a time window between said $S_2$ and $S_1$ sounds; and
  (vi) providing aural and visual quality inspection of said sounds in each of said time windows;
  (vii) rejecting said sounds which do not pass said quality inspection.

More specifically, with respect to FIG. 30, the data pre-processing may involve calibrating the sensor output for each channel. These calibrated outputs are bandpass filtered and then screened for aural abnormalities, such as the presence of background noise, etc. The calibrated outputs may also be synchronized with ECG data from a patient so as to window the data for the maximum blood flow period. This windowed data may then be visually inspected for each beat to detect abnormalities in the data, such as breath sounds or the like. For example, analysis windows (85 msec in mid-diastole of each beat identified by parsing algorithm) are visually inspected and are accepted unless there exists visually apparent interference from transients, breath sounds or other heart sounds such as S3 or S4. Aural screening of the recorded acoustic data identifies segments of interference from undesired noises including breath sounds, cable noises, bowel sounds, room noises, speech and various transients. Data may be accepted or rejected on a per beat basis based on the aural screening and visual inspection.

A non-invasive method for the detection of changes in CAD using the preliminarily processed signals is diagramed in FIG. 31 and comprises:
  (i) combining multiple signals from array sensors into a single signal as depicted in FIG. 32;
  (ii) providing feature data extracted from a patient before intervention;
  (iii) providing feature data extracted from a patient after intervention;
  (iv) pooling all feature data from all pre-intervention and all post-intervention heart beats of said patient;
  (v) separating said feature data provided in step (iv) using an optimal linear discriminant function or other feature classifier to produce a classifier output for each pre-intervention beat and each post-intervention beat derived from said patient;
  (vi) separately averaging across beats the pre-intervention and post-intervention classifier outputs produced in step (v); and
  (vii) determining the difference between the averaged pre-intervention and post-intervention classifier outputs obtained in step (vi),
  wherein said difference in average output from pre-intervention to post-intervention indicates a change in coronary artery stenosis for this patient.

More specifically, as seen in FIG. 31, the preprocessed data is converted from multiple channels by a beamforming process. Such an operation may also include the enhancements to signal to noise ratio discussed below. After beamforming, the output of the beamformer is converted to the frequency domain for energy feature extraction, preferably, by an FFT method. Alternatively, the beamforming may be carried out in the frequency domain.

In any event, the energy feature extraction is performed over two separate frequency bands by computing the energiews in high frequency band and a low frequency band. These features are assembled into a feature vector of length two. Multiple observation of the feature vector corresponding to different heart beats, are typically assembled into a feature matrix. Each row of the matrix contains a single feature vector and has length two and corresponds to a single observation or beat. The columns of the feature matrix are as long as the number of observations. These energies are then classified by a linear classifier which performs a least squares analysis of the data to linearly combine the two energies for a beat so as to provide a single output for each beat. The respective outputs for pre-intervention and post-intervention are then averaged to provide a single result for pre-intervention and a single result for post-intervention. Finally, these single pre-intervention and post-intervention results are compared to determine if a change has resulted from the intervention. Alternatively, pre-intervention data could be analyzed as described above and this single output could be compared against a standard to determine the presence of CAD in a patient. Thus, the present invention may be utilized for both predicting and tracking CAD in patients.

8. Signal to Noise Ratio Enhancement

One method for enhancing the S/N of a signal comprises:
  (i) providing an array of sensors positioned on the chest of a patient in an area above the patient's heart;
  (ii) performing a band limited cross-correlation of the signals in a specified frequency range;
  wherein two matrices, one of maximum cross-correlation values and one of the associated lags are generated;
  (iii) computing the optimal weights w* for each channel (see Appendix B);
  (iv) realigning said signals in said frequency range;
  (v) linearly combining using the optimal weights said realigned channels in the said frequency range;

wherein the linear combination is formed according to the following equation (see Appendix B):

$$y = \sum_{i=1}^{N} w_i^* x_i$$

where:
  y=single signal is combination of N sensor channels,
  $w_i^*$=weight for the ith channel,
  $x_i$=signal from the ith channel.

Equation 37

EXEMPLIFICATION OF THE INVENTION

EXAMPLE 1

Figure 33:
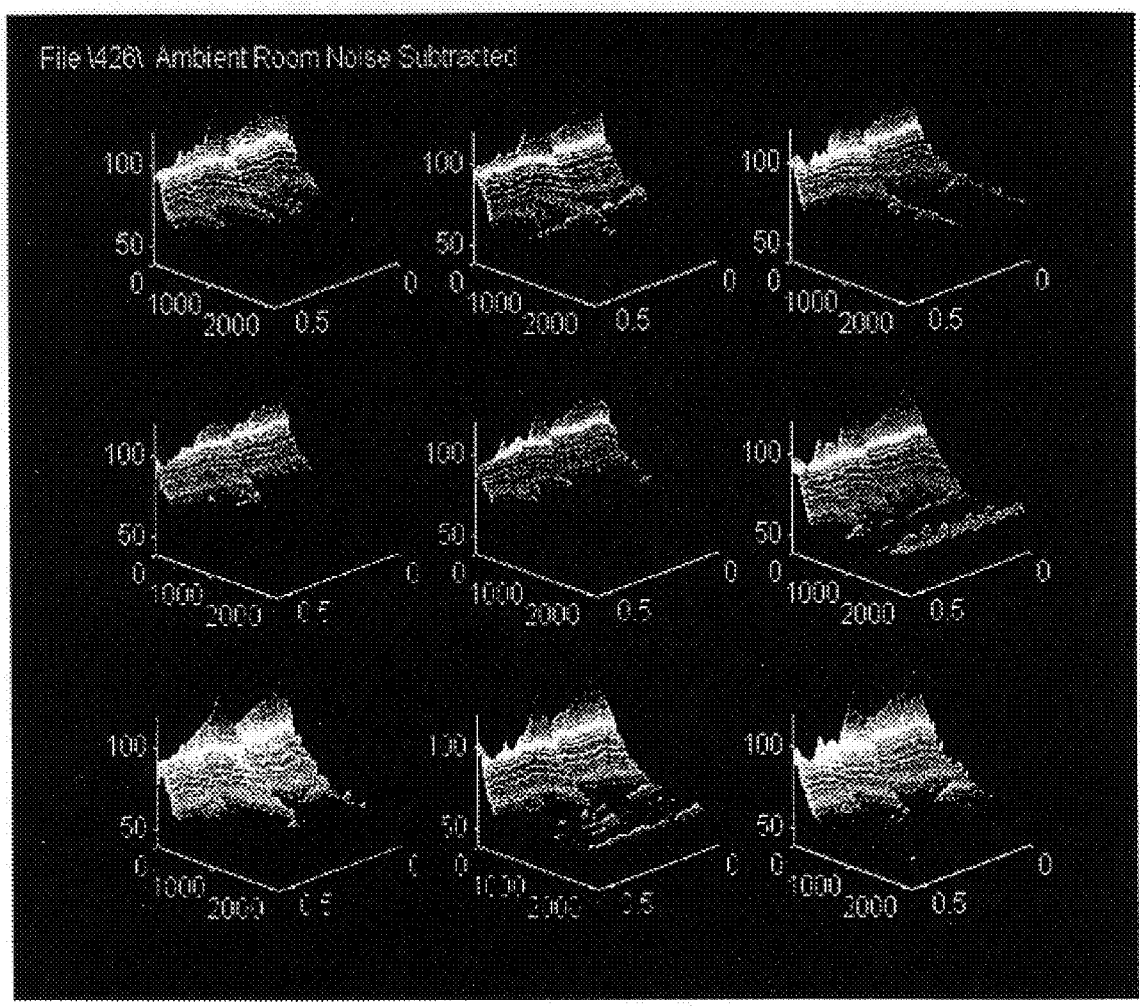
FIG. 33 shows spectrograms ambient room noise subtracted that illustrate the human cardiac cycle generated by each sensor of a nine sensor array as generally indicated by FIG. 6.

FIG. 33 shows spectrograms generated by a nine sensor array as shown in FIG. 6. The array was approximately centered at the third intercostal space at the left sternal border of the patient. The sensors were affixed to the patient's chest with double-sided adhesive pads. A computer-based clinical work station as generally described in the specification was used to digitize and record the acoustic signals from multiple cardiac cycles. The recorded signals of each sensor were described by the workstation signal conditioning circuitry with overlapping time windows and fast Fourier transformed to produce spectrograms of each heart. FIG. 33 displays the results of a single beat for each of the nine sensors.

EXAMPLE 2

Figure 34:
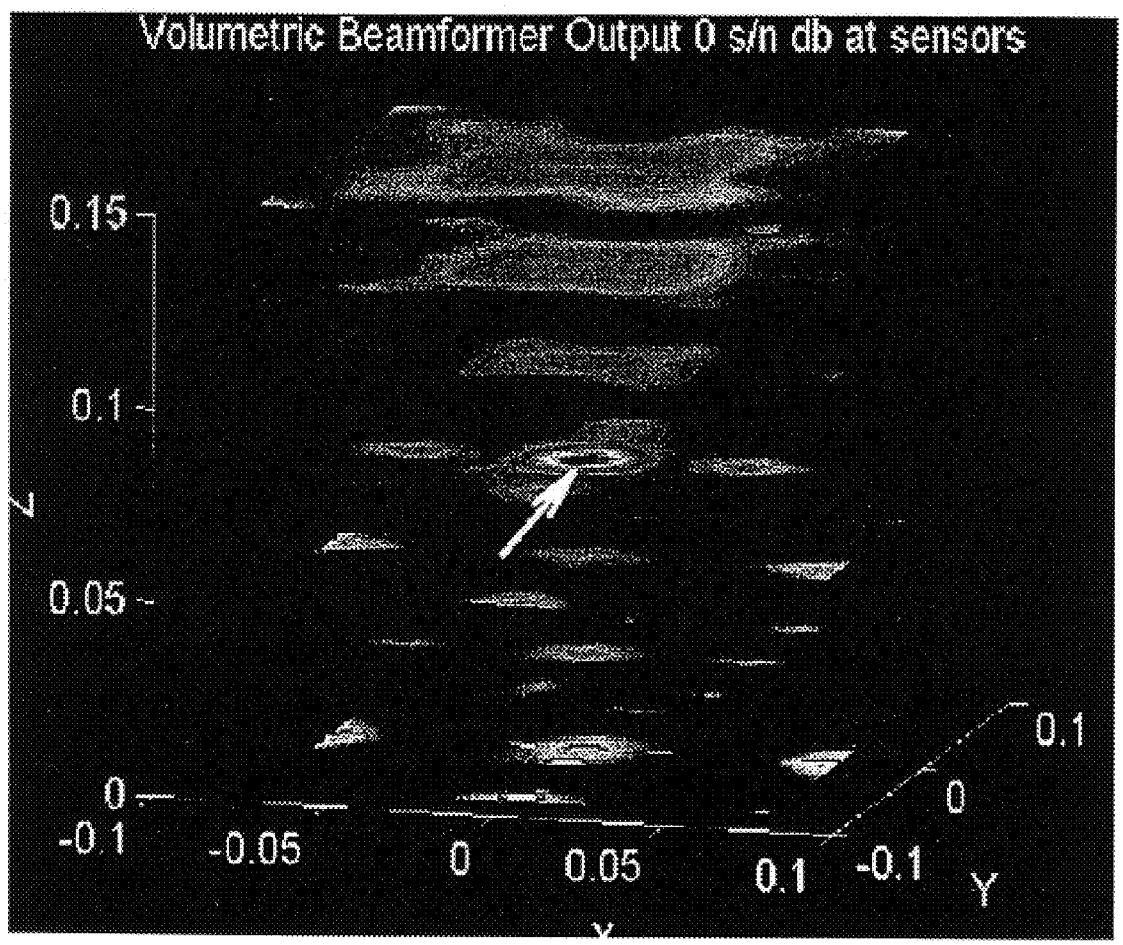
FIG. 34 is a volumetric image of a computer synthesized dispersive data model with added noise illustrating the origin of an acoustic shear wave.

FIG. 34 is a computer-generated illustration of the volumetric beamformer output indicating the origin of an acoustic shear-wave viewed in three dimensions using multiple cutting planes along the Z-axis. The acoustic image is obtained from the inverse path model of a nine-element array of sensors as shown by FIG. 6 using the conventional beamformer as described herein. The shear-wave source is correctly identified by the dense (red) plot located at coordinates X=0, Y=0, Z=7.5 centimeters.

Specifically:
1. Acoustic data for each of the nine sensor locations was generated by delaying the signal from the source location in the volume under the array to each sensor, according to the path length from source to sensor, and the wave speed dispersion as a function of frequency, as known for shear wave propagation in the viscoelastic material having properties of human tissue.
2. Incoherent noise at a level equal to that of the acoustic data signal was added to the signal at each sensor, thus creating a signal-to-noise ratio of 0 dB.
3. The conventional beamformer algorithm was applied to the array signals to produce a value of spatial coherence at each location in the volume beneath the array.
4. The magnitude of coherence was mapped to a color scale along planes arranged in the volume to create a three-dimensional display predicting source location.

EXAMPLE 3

Figure 35:
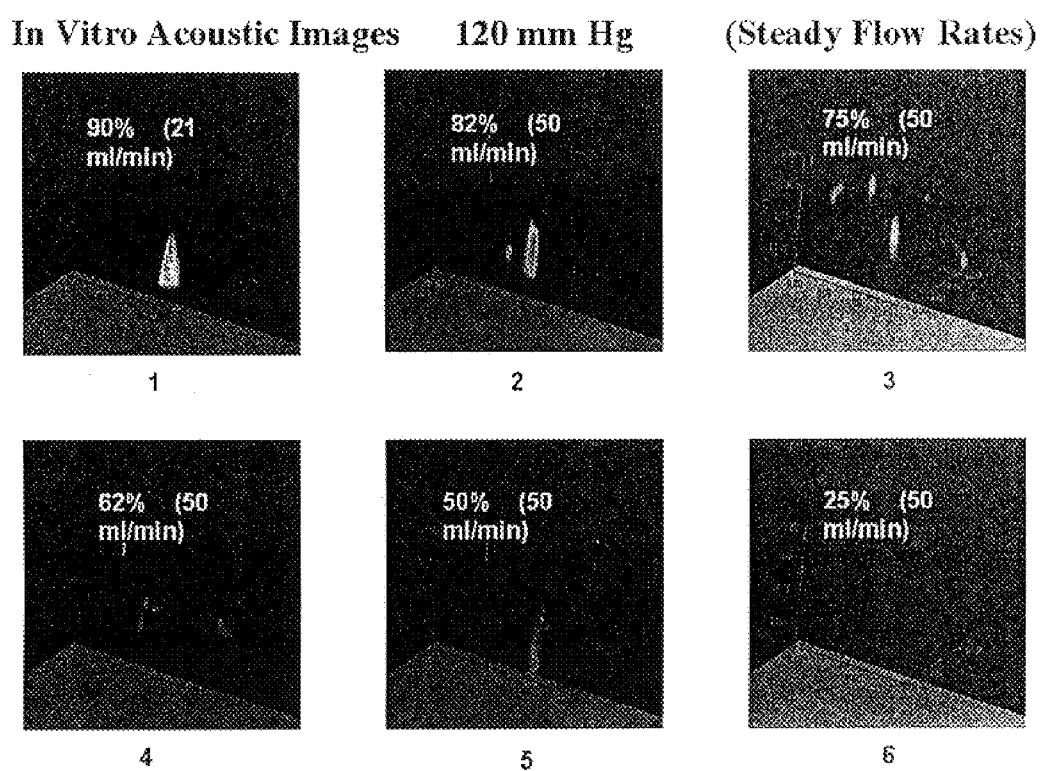
FIG. 35 is a volumetric image of data obtained from an in vitro test in a gelatine chest model with embedded silastic tube at six different tension severities (levels of stenosis), i.e., 25%, 50%, 62%, 76%, 82% and 90%.

FIG. 35 shows volumetric acoustic images of data obtained from in vitro tests in a gelatin volume. The figures illustrate the effect of six different degrees of occlusion, 25% to 90%, at steady anatomical flow. A nine sensor array similar to that shown by FIG. 6 was used.

EXAMPLE 4

Figure 36A:
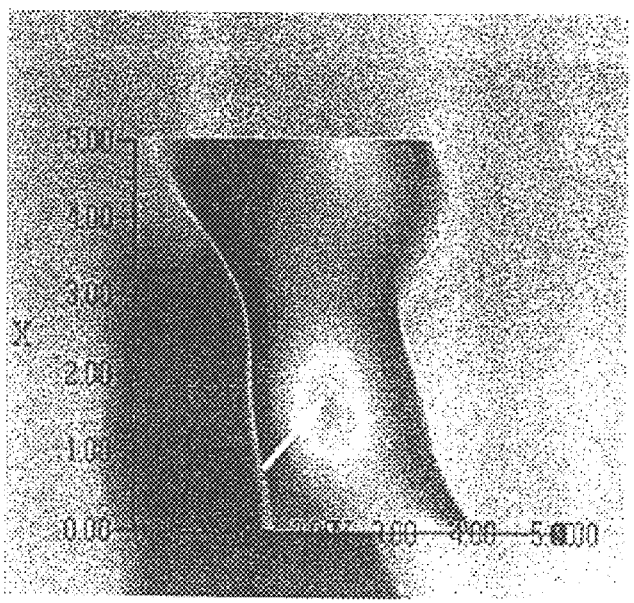
FIGS. 36A and 36B compare a volumetric acoustic image of a patient with 75% stenotic coronary lesion (FIG. 36A) to the angiographic record (FIG. 36B) of the same spatial location. The acoustic image was obtained by use of the non-invasive in vivo technology of this invention.
Figure 36B:
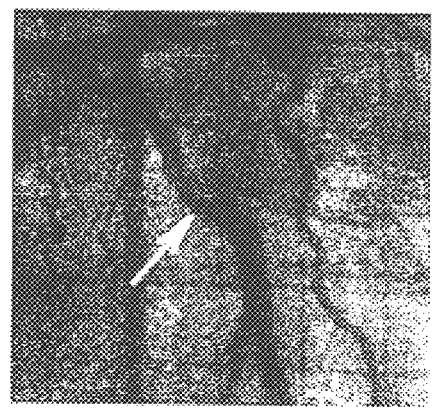

FIGS. 36A and 36B are a side-by-side comparison of the acoustic and radiographic images in the region of a 75% coronary lesion in a patient having coronary artery disease. The non-invasive, in vivo acoustic image, FIG. 36A, was obtained in substantially the same manner as in Example 1. Specifically:
1. The computer-based clinical workstation with appropriate signal conditioning circuitry was used to digitize and record the acoustic signals during an interval of several seconds.
2. The conventional beamformer algorithm was applied to the array signals to produce a value of spatial coherence at each location in the volume beneath the array.
3. The magnitude of coherence was mapped to a color scale along planes arranged in the volume to create a three-dimensional display predicting source location.
4. A radiographic image, FIG. 36B, of the coronary tree of a patient was produced using the known methods of coronary angiography, and aligned to the spatial reference of the acoustic image using radiopaque markers placed at the locations of the nine sensors of the acoustic array.
5. The acoustic image, FIG. 36A, and angiographic image, FIG. 37B, were compared at the location of the lesion.

The radiographic and acoustic images were two-dimensional, anterior-posterior views. The acoustic image correctly indicates the origin of a turbulent shear source just downstream from the 75% coronary occlusion.

EXAMPLE 5

Figure 37A:
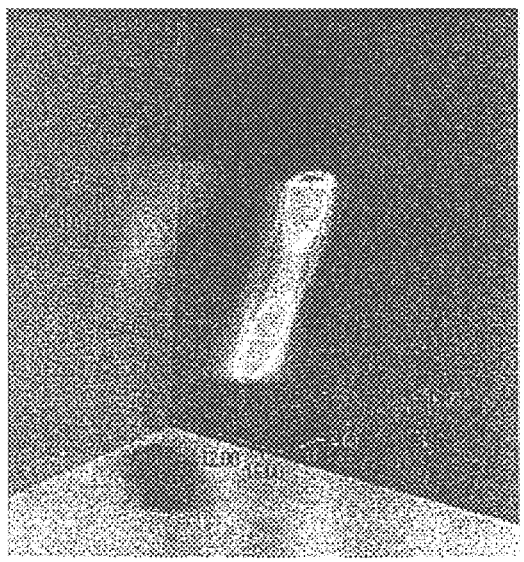
FIGS. 37A and 37B are volumetric images of a patient with 75% stenotic coronary lesion before (FIG. 37A) and after intervention (FIG. 37B).
Figure 37B:
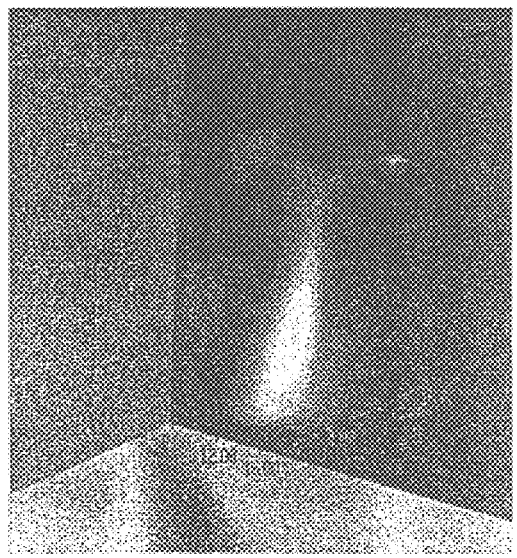

FIGS. 37A and 37B are three-dimensional in vivo volumetric acoustic images at the location of two coronary lesions separated by a few centimeters in the left anterior descending coronary artery of a patient having coronary artery disease. The left image in FIG. 37A is produced in substantially the same manner as in Example 1. An intervention was performed whereby the patient receives treatment by placement of two stents to repair the stenoses. A second volumetric acoustic image, FIG. 37B, produced post-intervention in like manner. The volumetric acoustic images, FIGS. 37A and 37B, were compared.

FIG. 37A shows the turbulent sources prior to surgical intervention. FIG. 37B shows the same cardiac region seventeen hours after two stents were placed in the artery to correct the stenoses. The images measure five centimeters on each edge of the volumetric cube, and were created using the conventional beamformer described herein.

EXAMPLE 6

FIGS. 38 and 39 illustrate an example of non-invasive, in vivo detection of change in a patient's acoustic features obtained using the nine-element sensor array described in FIG. 6 and time-alignment signal processing, referring to FIG. 38A, acoustic energy at high and low frequencies for a patient having coronary artery stenosis is shown by the points scattered in the upper section of the plot. Following surgical intervention to repair the coronary lesion, the acoustic energy appears clustered at the lower left.

The pre- and post-intervention feature data illustrated by FIG. 38 was classified by beat number. FIG. 39 is a plot of beat number against classifier output. The pre-intervention beats subclass appears in the upper left quadrant of FIG. 39, wherein the post-intervention beats appear in the lower right quadrant of FIG. 39.

Specifically:
1. Patient acoustic signals are acquired as described in Example 3.
2. Patient acoustic signals were acquired using steps 1 and 2 of Example 2.
3. Diastolic interval data from each channel and each beat are extracted.
4. A cross-correlation across channels was performed to obtain optimal weights and time lags. The data of each channel is then weighted in amplitude, shifted in time to align the wave arrivals, and summed.
5. The combined (summed) data from each beat was transformed into the frequency domain using FFT methods.
6. For each beat, the frequency domain data was summed over low and high feature bands for frequency bands of approximately 200 Hz–600 Hz to produce a low frequency estimator, and over frequency bands of approximately 600 Hz to 1,800 Hz to produce a high frequency estimator.
7. The results for pre-intervention and post-intervention low and high frequency estimators were plotted for comparison.

EXAMPLE 7

Non-invasive Detection of CAD Change

The methods for non-invasive detection of changes in CAD as described in the specification were applied to patients taking part in a controlled study conducted at two research hospitals. A passive acoustic sensor array was used to acquire data from 44 patients before (pre) and after (post) percutaneous coronary intervention. Acoustic features were extracted from the mid-diastolic sounds measured from multiple cardiac cycles in each patient. A training sample, using data from half of the cardiac cycles was used in a feature separation algorithm to separate the pre and post acoustic features for each patient. The remaining acoustic features were used to validate the separation algorithm. Non-invasively detected acoustic feature changes after successful percutaneous intervention indicate changes in CAD. Using this technique, the acoustic features differentiated the status of the patient (pre vs. post) in 41 of 44 patients (93%). See Table A.

EXAMPLE 8

Comparative Example to Demonstrate S/N Ratio Enhancement

The Table A data shows that the method of optimally combining the signals from multiple sensors, described previously, ensures the highest performance of the non-invasive methods of detecting changes in coronary artery stenosis as described. Table A also illustrates the method of the invention for enhancing the signal to noise ratio of acoustic abnormal blood flow signals. No single channel produces better results than this method. To demonstrate the benefit of S/N ratio enhancement achieved by optimally combining the sensor data from the array, the technique used for non-invasive detection of stenosis change has been applied to patient data as described in Example 7 using three different approaches. The first approach uses features extracted from the optimally combined channels. The second and third approaches used features extracted from single channel data. In the second approach, the channel with the maximum energy was used. In the third approach, the channel with the minimum energy was used. All other aspects of the method for detecting changes in stenosis were kept the same. The channel with the highest S/N ratio is deemed to have the highest total energy also. The method does not perform as well using the single sensor with the highest S/N ratio compared to the enhancement achieved by optimally combining the signals from the array sensors. Clearly, the performance is much worse for a poorly placed sensor with relatively low S/N ratio.

TABLE A

| METHOD | # OF DETECTIONS/ # OF PATIENTS | % DETECTION |
| --- | --- | --- |
| Optimally Combining Channels | 41/44 | 93.2 |
| Maximum Energy | 39/44 | 88.6 |
| Minimum Energy | 35/44 | 79.5 |

We claim:
1. A non-invasive, in vivo, method for detecting change in coronary artery stenosis which comprises the steps of:
   (i) procuring a plurality of heart sound data sets which are indicative of a stenosis in a patient's coronary artery wherein each of said data sets is procured at a different time,
   (ii) comparing at least two of the data sets to identify selected differences between said sets,
   wherein a difference identified in said comparing step corresponds to a change in the coronary artery stenosis of the patient.
2. The claim 1 method wherein said heart sound data sets is comprised of sets of data generated by an array of acoustic sensors positioned on the chest of said patient.
3. The claim 1 method, wherein said heart sound data sets are sets of heart sound data generated by sensing shear waves.
4. The claim 1 method wherein said heart sound data sets exclude heart sound data generated by compression waves.
5. A method according to claim 1, wherein said procuring step comprises the steps of:
   placing an array of sensors on an area of the body surface of a patient above a volume of said body which may include abnormal blood flow, wherein each of said sensors in said array includes means to receive sounds caused by blood flow in said volume of said patient's body and to generate electrical signals from said sounds, and
   combining said electrical signals generated by a plurality of said sensors in said array for each of said data sets obtained at different times,
   wherein said comparing step includes the step of providing a display of the spatial distribution of phase coherence in said combined electrical signal, and wherein abnormal blood flow in said volume of said patient's body is indicated by non-uniformity in said display of said spatial distribution of said phase coherence.
6. A method according to claim 1, wherein said procuring step comprises the steps of:
   (i) positioning a plurality of sensors in an array on an area of a patient's body above a volume of said patient's body in which abnormal blood flow may be present; and
   (ii) beamforming said plurality of sensors to provide a beamformer output; and wherein said comparing step includes the step of processing said beamformer output to detect said abnormal blood flow, if present, in said vessel of said patient.

7. A method according to claim 6, wherein said beamformer output is provided by a beam steering angle of from 30 to 30° as a function of the number of sensors of when the source of the formed beam is at infinity.

8. The method of claim 6, wherein an adjustable gain/resolution null space beamformer is used to provide said beamformer output.

9. A method according to claim 6, wherein the plurality of sensors comprises sensors having a stretched piezolelectric film transducer.

10. A method according to claim 1, wherein said comparing step detects abnormal blood flow in a vessel of a patient wherein the abnormal blood flow is caused by a partial occlusion of the vessel, wherein the abnormal blood flow produces sounds detectable at the surface of said patient's body, and wherein said procuring step comprises the steps of:
(i) positioning a plurality of sensors in an array on an area of the body surface of the patient above a vessel which may include the partial occlusion,
(ii) detecting sounds from the sensors caused by abnormal blood flow if present in the vessel of the patient;
(iii) generating electrical signals responsive to said detecting step the electrical signals which includes a compression wave component and a shear wave component;
(iv) locating each of said sensors on the surface of the body of said patient; and
(v) isolating said shear wave component, if present therein, from said plurality of electrical signals transmitted by said plurality of sensors; and
wherein said comparing step comprises processing said isolated shear wave component to detect if there is an occlusion present in the vessel of the patient.

11. The method of claim 10, further comprising the step of providing a display indicative of the occlusion if present in the vessel of the patient.

12. The method claim 10, wherein said shear wave component is isolated in step (v) by blocking the compression wave component in said signals transmitted by said sensors.

13. The method of claim 10, wherein said locating step is performed such the physical location on the subject is identified by photogrammetry.

14. The method of claim 10, wherein said compression wave component is blocked by velocity filtering or by steering a null at the source of said compression wave.

15. A method for non-invasively detecting a change in coronary artery stenosis, comprising the steps of:
positioning a first sensor array on the skin of a patient;
obtaining a first set of acoustic data from the sensor array at a first time;
removing the sensor array from the skin of the patient;
positioning a second sensor array on the skin of a patient;
obtaining a second set of acoustic data from the sensor array at a second time, the second time being temporally separate from the first time;
comparing the first and second acoustic data sets; and
determining a change in coronary artery stenosis in the patient based on said comparing step.

16. A method according to claim 15, wherein said comparing step includes identifying high and low energy features associated with the first and second data sets.

17. A method according to claim 15, further comprising the step of obtaining an ECG of the patient, and wherein said comparing step considers the ECG of the patient.

18. A method according to claim 17, wherein said comparing step comprises the step of parsing the first and second acoustic data sets to synchronize the data to the heartbeats of a patient.

19. A method according to claim 18, wherein said comparing step further comprises the steps of:
averaging the parsed data across a plurality of heartbeats of the patient; and
beamforming the averaged data into the time domain.

20. A method according to claim 19, wherein said comparing step comprises the step of extracting selected energy features at two frequencies associated with the first and second data sets, and wherein the extracted energy features of each of the first and second data sets are used in said determining step.

21. A method according to claim 20, wherein said selected energy features include a first energy feature at a first frequency which is between 200–600 Hz and a second energy feature at a second frequency higher than the first frequency, the second frequency being between 600–1800 Hz.

22. A method according to claim 15, wherein the first data set is obtained before and the second data set obtained after an interventional treatment has been performed on the patient.

23. A method according to claim 22, wherein said determining step estimates the change in the size of a stenotic coronary lesion.

24. A method according to claim 15, wherein the acoustic data includes data which corresponds to shear wave data acquired during the second quarter of the diastolic period of a patient.

25. A method according to claim 15, further comprising the step of acquiring ambient noise information which may impact the reliability of the sensed acoustic data.

26. A method according to claim 20, wherein said comparing step further comprises the step of classifying the extracted energy features per beat into a first subclass associated with pre-intervention data and a second subclass associated with post intervention data.

27. A method according to claim 26, further comprising the step of averaging the first and second data subclasses from said classifying step across beats.

28. A method according to claim 27, further comprising the step of plotting the classified subclass data associated with the pre- and post-intervention at the two selected frequencies.

29. A method according to claim 28, wherein said comparing step considers the number of data points at each of the two frequencies for the pre- and post-intervention subclass data in said plotting step.

30. A method according to claim 15, further comprising the step of generating a time series of acoustic images, wherein one said acoustic image is from the first acoustic data set at the first time and another of said acoustic image is from the second acoustic data at the second time.

31. A method according to claim 30, wherein the acoustic images are three-dimensional.

32. A method according to claim 15, wherein the first and second acoustic data is multi-channel data obtained for each heartbeat.

33. A method according to claim 15, wherein the obtaining steps include obtaining multi-channel acoustic data for a plurality of heartbeats, said method further comprising the step of screening each of the first and second acoustic data sets obtained for each heartbeat to select which to include in said comparing step.

34. A method according to claim 33, wherein all channel data corresponding to a particular heartbeat is retained together or rejected together.

35. A method for identifying post-intervention changes in coronary heart stenosis which comprises:
   (i) providing energy feature data indicative of coronary artery stenosis extracted from heartbeats of a patient before intervention;
   (ii) providing energy feature data indicative of coronary artery stenosis extracted from heartbeats of a patient after intervention;
   (iii) pooling all of said feature data from all pre-intervention and all post-intervention data from said heart beats of said patient;
   (iv) classifying said feature data pooled in step (iii) wherein a classifier output is produced for each pre-intervention beat and each post-intervention beat of said patient's heart; and
   (v) separately averaging said pre-intervention and post-intervention classifier output data produced in step
   (iv) across said beats; and (vi) determining the difference between the average of the pre-intervention and the average of the post-intervention classifier outputs obtained in step (v);
      wherein a risk of coronary heart disease may be indicated when said difference in said average output from said post-intervention classifier outputs is equal to or greater than the average of said post-intervention classifier outputs.

36. A non-invasive, in vivo method for detecting coronary artery stenosis change over time which comprises:
   (i) providing an array of acoustic sensors positioned on a patient's chest
      wherein said sensors detect $S_1$, $S_2$ and quiet interval sounds produced by said patient's heart and convert said sounds to an electrical signal and
      wherein said electrical signal includes a heart sound component and a noise component;
   (ii) amplifying particular signal to noise ratio from said electrical signal;
   (iii) subjecting said amplified electrical signal to signal processing to provide a processed signal having an increased signal to noise ratio;
   (iv) isolating the portion of said processed signal of step (iii) which corresponds to the quiet interval in said patient's heart sounds detected by said sensors in step (i);
   (v) subjecting quiet interval signals isolated in step (iv) to visual screening wherein portions of said quiet interval signals attributable to breath sounds or transient noise are rejected and other portions of said signal are accepted;
   (vi) subjecting said quiet interval signals isolated in step (iv) to aural screening wherein a portion of said signal is bandpass filtered from 500 Hz to 1800 Hz wherein regions with noise interference indicative of breathing sounds or cable noises or room noises or speech or bowel sounds are rejected;
   (vii) identifying and correlating portions of the patient's heart sound signal residual after step (vi) with first, second and third beats of said patient's heart with corresponding first, second and third signal channels;
   (viii) providing a time alignment of said first, second and third channels;
   (ix) assigning optimal weights to each of said time aligned signals;
   (x) computing two energy-based features from said time aligned and optimally weighted signals
      wherein a first energy based feature is computed at a low frequency from 200 Hz to 600 Hz and
      wherein a second energy based feature is calculated at a frequency of 600 Hz to 1800 Hz.

37. A method for acquiring and preprocessing data in preparation for signal analysis to detect changes in coronary artery stenosis which comprises:
   (i) providing a fixed array of sensors conformable to the chest of a patient;
      wherein said sensors detect cardiac sounds in said chest of said patient and convert said blood flow sounds to electrical signals;
   (ii) placing said array on the chest of said patient in an area above said patient's heart, wherein the patient's heart beat generates $S_1$, $S_2$, $S_3$, $S_4$ and other cardiac sounds;
   (iii) converting said cardiac sounds into engineering units of acceleration wherein said units of accelerator constitute said signals to be analyzed;
   (iv) segmenting said signals into acceleration units identifying individual beats of said patient's heart;
   (v) providing a real time window between said $S_2$ and $S_1$ sounds of each of said individual beats of said patient's heart; and
   (vi) subjecting said $S_1$ and $S_S$ sounds to quality inspection of said sounds.

* * * * *